(12) United States Patent
Schotten et al.

(10) Patent No.: US 10,357,751 B2
(45) Date of Patent: *Jul. 23, 2019

(54) POLYMER MICELLES CONTAINING NANOPARTICLES IN NON-AQUEOUS SOLUTION, METHODS FOR THEIR PREPARATION AND USE

(71) Applicant: FRAUNHOFER-GESELLSCHAFT ZUR FÖRDERUNG DER ANGEWANDTEN FORSCHUNG E.V., Munich (DE)

(72) Inventors: Theo Schotten, Vierhoefen (DE); Katja Werner, Klein Nordende (DE); Carsten Ott, Bad Segeberg (DE); Jan Steffen Niehaus, Wentorf (DE); Marieke Dieckmann, Hamburg (DE); Horst Weller, Hamburg (DE); Johannes Ostermann, Hamburg (DE); Christoph Hahn, Hamburg (DE)

(73) Assignee: FRAUNHOFER-GESELLSCHAFT ZUR FORDERUNG DER ANGEWANDTEN FORSCHUNG E.V., Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/519,130

(22) PCT Filed: Oct. 13, 2015

(86) PCT No.: PCT/EP2015/073624
§ 371 (c)(1),
(2) Date: Apr. 13, 2017

(87) PCT Pub. No.: WO2016/059019
PCT Pub. Date: Apr. 21, 2016

(65) Prior Publication Data
US 2017/0225141 A1 Aug. 10, 2017

(30) Foreign Application Priority Data
Oct. 13, 2014 (DE) .................. 10 2014 114 834

(51) Int. Cl.
| | | |
|---|---|---|
| *B01J 13/02* | (2006.01) | |
| *C08K 3/08* | (2006.01) | |
| *B01J 13/14* | (2006.01) | |
| *C09B 67/02* | (2006.01) | |
| *G01N 33/543* | (2006.01) | |
| *B82Y 5/00* | (2011.01) | |
| *C09K 11/02* | (2006.01) | |
| *C09K 11/88* | (2006.01) | |

(52) U.S. Cl.
CPC .............. *B01J 13/02* (2013.01); *B01J 13/14* (2013.01); *B82Y 5/00* (2013.01); *C08K 3/08* (2013.01); *C09B 67/0097* (2013.01); *C09K 11/025* (2013.01); *C09K 11/883* (2013.01); *G01N 33/5432* (2013.01); *C08K 2003/085* (2013.01); *C08K 2003/0806* (2013.01); *C08K 2003/0843* (2013.01)

(58) Field of Classification Search
CPC ........... B01J 13/02; B01J 13/14; C09K 11/02; C09K 11/88; C09K 11/025; C09K 11/883; G01N 33/543; G01N 33/5432; B82Y 5/00; C08K 3/08; C08K 2003/0806; C08K 2003/0843; C08K 2003/085; C09B 67/0097
See application file for complete search history.

(56) References Cited

U.S. PATENT DOCUMENTS

| | | |
|---|---|---|
| 2005/0019901 A1 | 1/2005 | Matveeva et al. |
| 2010/0215852 A1 | 8/2010 | Rowe et al. |

FOREIGN PATENT DOCUMENTS

| | | |
|---|---|---|
| WO | 2008030805 A1 | 3/2008 |
| WO | 2010100108 A1 | 9/2010 |
| WO | 2013113328 A1 | 8/2013 |

OTHER PUBLICATIONS

Flory, P., "Thermodynamics of High Polymer Solutions," Journal of Chemical Physics, vol. 10, No. 51, Jan. 1942, 11 pages.
Huggins, M., "Thermodynamic Properties of Solutions of Long-Chain Compounds," Annals of the New York Academy of Sciences, vol. 43, No. 1, Mar. 30, 1942, 32 pages.
Kim, B. et al., "Magnetomicelles: Composite Nanostructures from Magnetic Nanoparticles and Cross-Linked Amphiphilic Block Copolymers," Nano Letters, vol. 5, No. 10, Oct. 1, 2005, Available Online Sep. 10, 2005, 5 pages.
Lin, C. et al., "Design of an Amphiphilic Polymer for Nanoparticle Coating and Functionalization," Small, vol. 4, No. 3, Mar. 3, 2008, Available Online Feb. 13, 2008, 8 pages.
Pöselt, E. et al., "Highly Stable Biocompatible Inorganic Nanoparticles by Self-Assembly of Triblock-Copolymer Ligands," Langmuir, vol. 25, No. 24, Dec. 15, 2009, Available Online Aug. 11, 2009, 8 pages.
Pöselt, E. et al., "Tailor-Made Quantum Dot and Iron Oxide Based Contrast Agents for in Vitro and in Vivo Tumor Imaging," ACS Nano, vol. 6, No. 4, Apr. 24, 2012, Available Online Mar. 30, 2012, 10 pages.
Schmidtke, C. et al., "Amphiphilic, cross-linkable diblock copolymers for multifunctionalized nanoparticles as biological probes," Nanoscale, vol. 5, No. 16, Aug. 21, 2013, Available Online Jun. 11, 2013, 12 pages.
Schmidtke, C. et al., "Polymer-Assisted Self-Assembly of Superparamagnetic Iron Oxide Nanoparticles into Well-Defined Clusters: Controlling the Collective Magnetic Properties," Langmuir, vol. 30, No. 37, Sep. 23, 2014, Available Online Aug. 25, 2014, 7 pages.
ISA European Patent Office, International Search Report Issued in Application No. PCT/EP2015/073626, dated Apr. 18, 2016, WIPO, 5 pages.
ISA European Patent Office, International Search Report Issued in Application No. PCT/EP2015/073624, dated May 2, 2016, WIPO, 5 pages.
Schotten, T. et al., "Polymer Micelles Containing Nanoparticles in Non-Aqueous Solution, Methods for their Preparation and Use," U.S. Appl. No. 15/519,120, filed Apr. 13, 2017, 88 pages.

*Primary Examiner* — Irina S Zemel
(74) *Attorney, Agent, or Firm* — McCoy Russell LLP

(57) ABSTRACT

The present invention relates to a composition, comprising at least one micelle in non-aqueous solution, wherein the micelle encapsules one or more nanoparticle(s) and wherein the micelle comprises a cross-linked hydrophilic shell. Furthermore, the present invention relates to the use of such a composition and to methods for providing such a composition.

15 Claims, 31 Drawing Sheets

POLYMER MICELLES CONTAINING NANOPARTICLES IN NON-AQUEOUS SOLUTION, METHODS FOR THEIR PREPARATION AND USE

CROSS-REFERENCE TO RELATED APPLICATIONS

The present application is a U.S. National Phase of International Patent Application Serial No. PCT/EP2015/073624 entitled "POLYMER MICELLES CONTAINING NANOPARTICLES IN NON-AQUEOUS SOLUTION, METHODS FOR THEIR PREPARATION AND USE," filed on Oct. 13, 2015. International Patent Application Serial No. PCT/EP2015/073624 claims priority to German Patent Application No. 10 2014 114 834.7, filed on Oct. 13, 2014. The entire contents of each of the above-referenced applications are hereby incorporated by reference for all purposes.

TECHNICAL FIELD

The present invention relates to a composition comprising micelles, which encapsulate nanoparticles. Furthermore, the present invention relates to the use of such a composition and to methods for providing such a composition.

BACKGROUND

Nanoparticles have been a subject of great interest, promising extensive applications including display devices, information storage, biological tagging materials, diagnostic imaging, drug delivery, theranostics, photovoltaics, sensors and catalysts. Nanoparticles having small diameters can have properties intermediate between molecular and bulk forms of matter. For example, nanoparticles based on semiconductor materials having small diameters can exhibit quantum confinement of both the electron and hole in all three dimensions, which leads to an increase in the effective band gap of the material with decreasing crystallite size. Moreover, the magnetic properties of matter change dramatically depending on the particle size. Likewise, the plasmon-related absorption of nanoparticles, e.g. gold nanoparticles largely depends on the size and the shape of said particles. Biological effects of nanoparticles, e.g. permeability through biological barriers, like membranes, skin etc. or toxicity show distinct size-related dependencies. Most nanoparticles consist of an inorganic core that is surrounded by a layer of organic ligands. This organic ligand shell is critical to the nanoparticles for controlled growth, stability, prevention of agglomeration, processing, modification, and incorporation into various substrates. Originally, this organic ligand shell around a nanoparticle is formed in situ after nucleation and growth of the nanoparticle in its growth solution. For most applications, nanoparticles must be processed outside of their growth solution and transferred into various chemical environments. However, nanoparticles often lose their specific physical and chemical properties, e.g. high fluorescence, or become irreversibly aggregated when removed from their growth solution. Commonly, nanoparticles of defined shape, size and physico-chemical properties are synthesized in high boiling hydrophobic solvents, e.g. diphenyl ether, squalene and the like, containing hydrophobic ligands, e.g. trialkyl phosphines or phosphine oxides, e.g. trioctyl phosphine (TOP) or its corresponding phosphine oxide (TOPO), long chain aliphatic or unsaturated fatty acids or amines, e.g. oleic acid (OA) or hexadecyl amine (HDA) and the like, which—albeit indispensable for the synthesis-restrict the use of nanoparticles in diverse technical fields mentioned above. Different methods have been described for the transfer of nanoparticles into various chemical environments, e.g. ligand exchange or encapsulation into polymer micelles or polymersomes.

A micelle comprises of a plurality of amphiphilic molecules, each consisting of a hydrophilic "head" region and a hydrophobic "tail" region in the same molecule. Said amphiphilic molecule may be a small molecule with a low molecular weight, typically below 1000 Dalton, e.g. sodium dodecyl sulfate, salts of long chain fatty acids, phospholipids, and the like, or an amphiphilic block copolymer. Hence, it should be noted that in the context of the invention, the amphiphilic subunits a micelle is comprised of are termed as "unimers", regardless of the molecular weight or the amphiphilic chemical structure. Thus the terms "unimer" or "unimers" will be applied to amphiphilic block polymers as well, if molecules of said polymers account for the amphiphilic subunits of a micelle.

In general, micellization, i.e. micelle formation of amphiphilic molecules takes place either in solvents like water or in unpolar organic solvents, e.g. hydrocarbons, e.g. hexane, toluene and the like. In the first case a normal micelle, in the latter an inverse (or reverse) micelle is formed. The terms "reverse micelle" and "inverse micelle" are used synonymously within the scope of the invention. This self-assembly process relies on a thermodynamic equilibrium. In an aqueous environment solvation of the hydrophobic tail is entropically unfavorable. Nonetheless, at very low concentrations the unimers are still completely dissolved, i.e. in a disordered highly entropic condition. With increasing concentrations of the unimer the hydrophobic tails sequester away from the water phase by micelle formation, i.e. forming ordered, mostly—but not exclusively-spherical arrangements comprised of a hydrophobic core and a hydrophilic shell, namely a normal micelle. The entropy gained from the release of water molecules from the solvation shell of the hydrophobic tails outweighs the loss of entropy caused by micelle formation. The minimum concentration of unimers at which micelle formation starts to happen is the so-called critical micelle concentration (CMC)

Reversely, in a non-polar organic solvent, an inverse micelle is formed, wherein the hydrophilic head groups of the amphiphilic unimers aggregate to a hydrophilic core, shielded from the non-polar solvent by a shell of hydrophobic tails.

Accordingly, a micelle and its corresponding dissolved unimers are in a dynamic equilibrium, thus the stability of micelles depends on the concentration of unimers, salt concentration, temperature etc. This thermodynamic equilibrium can be frozen in favor of the micelle formation, if the unimers of which the micelle is comprised of, are irreversibly cross-linked.

It has been demonstrated that in an aqueous environment hydrophobic nanoparticles, as mentioned above, can be enclosed into the hydrophobic core of a micelle, when mixed with amphiphilic molecules, hence producing an aqueous colloidal solution of said nanoparticles. (E. Pöselt, S. Fischer, S. Förster, H. Weller; Highly Stable Biocompatible Inorganic Nanoparticles by Self-Assembly of Triblock-Copolymer Ligands *Langmuir* 2009, 25, 13906-13913.) (B.-S. Kim, J.-M. Qiu, J.-P. Wang, T. A. Taton; Magnetomicelles: Composite Nanostructures from Magnetic Nanoparticles and Cross-Linked Amphiphilic Block Copolymers *Nano Letters* 2005, 5, 1987-1991.) (E. Pöselt, C. Schmidtke, S. Fischer, K. Peldschus, J. Salamon, H. Kloust, H. Tran, A.

Pietsch, M. Heine, G. Adam, U. Schumacher, C. Wagener, S. Förster, H. Weller; Tailor-Made Quantum Dot and Iron Oxide Based Contrast Agents for in Vitro and in Vivo Tumor Imaging *ACS Nano* 2012, 6, 3346-3355.) (C.-A. J. Lin, R. A. Sperling, J. K. Li, T.-Y. Yang, P.-Y. Li, M. Zanella, W. H. Chang, W. J. Parak, Design of an Amphiphilic Polymer for Nanoparticle Coating and Functionalization *Small* 2008, 3, 334-341.) Said amphiphilic molecules include naturally occurring lipids, e.g. phospholipids like lecithin, cationic, zwitterionic, anionic and non-ionic surfactants, as well as macromolecular amphiphiles like block copolymers, comprised of at least two polymer blocks of different compatibility to a given solvent, according to the Flory-Huggins theory, e.g. Thermodynamic Properties of Solutions of Long-Chain Compounds, Annals of the New York Academy of Sciences, Volume 43, p. 1-32 (1942); Paul J. Flory, Thermodynamics of High Polymer Solutions; The Journal of Chemical Physics 10, 51 (1942).

It has also been demonstrated that hydrophilic nanocrystals can be grown in the interior volume of reverse micelles. However, the quality of the nanocrystals generated by this method is often unsatisfying with respect to their properties.

It is evident that said aqueous colloidal preparation of micellar enclosed nanoparticles determines and restricts the use of this preparation. Albeit eventually suitable for biological or medical applications, said aqueous preparations show a number of shortcomings. Firstly, the transfer of fluorescent semi conductor nanoparticles into water may deteriorate their fluorescence properties by quenching. In another aspect, the coupling chemistry for biofunctionalization, i.e. the conjugation of micellar encapsulated nanoparticles with biofunctional entities, like proteins, peptides, antibodies, carbohydrates, lectins, nucleic acid fragments, DNA, RNA, aptamers etc., often benefits from non-aqueous conditions. The aqueous environment may hamper conjugation of said entities, because the conjugation site is poorly accessible, due to folding and coiling of said entities in an aqueous environment. In contrast, many of said biofunctional entities disentangle under non aqueous conditions, thus making putative coupling sites well amenable to conjugation. Consequently, aqueous compositions of nanoparticles cannot be used under said conditions, or suffer from strongly reduced coupling yields.

Furthermore, regiochemistry of the coupling substrate may be ambiguous, due to a plurality of functionalities of similar reactivity, e.g. multiple lysine residues, hence leading to intractable mixtures of specimens of undefined biological activity. In principle, this drawback can be avoided by employing suitable protective group chemistry, in order to control regiochemistry. However, protection of proteins, peptides, antibodies, carbohydrates, lectins, nucleic acid fragments, DNA, RNA, aptamers etc. frequently renders these molecules sparingly soluble or even insoluble in water, making the coupling conditions incompatible to aqueous compositions of micelle encapsulated nanoparticles.

Moreover, said biofunctionalized nanoparticle conjugates require low storage temperatures in order to prevent decomposition. Unfortunately, the matrix conditions in frozen aqueous solutions at or below 0° C. are often detrimental to the physicochemical properties of nanoparticles, e.g. causing loss of fluorescence or irreversible aggregation after thawing.

Decomposition of said biofunctionalized nanoparticle conjugates may also occur from microbial infestation. Therefore, an addition of microbicides, e.g. sodium azide is frequently required. However, said additives are frequently detrimental to common coupling reactions and furthermore often interfere with or even override the intrinsic biological activities of said biofunctionalized nanoparticle conjugates, thus distorting testing results.

It is therefore an object of the present invention to resolve said shortcomings and to provide an improved composition comprising micelles, which encapsulate nanoparticles and to provide an improved use of such a composition and methods for providing such a composition.

SUMMARY OF THE PRESENT INVENTION

The above object is solved by a composition, the use of a composition and methods for providing such a composition according to the present invention.

In particular, the present invention provides a composition, comprising at least one micelle in non-aqueous solution, wherein the micelle encapsulates one or more nanoparticles and wherein.

Further embodiments of the composition are described hereinafter and are subject-matter of the claims being dependent from claim 1.

According to a further aspect of the invention, the nanoparticle is a luminescent nanoparticle.

According to a further aspect of the invention, the nanoparticle is a semi-conductor nanoparticle.

According to a further aspect of the invention, the nanoparticle is doped by heavy-metal ions like Ag, Cu, Co, or Mn.

According to a further aspect of the invention, the nanoparticle is chosen from a salt-like lattice lanthanide doped nanoparticle.

According to a further aspect of the invention, the nanoparticle is a metal nanoparticle or metal oxide nanoparticle.

According to a further aspect of the invention, the material of the nanoparticle is defined by the formula $M_wN_xA_yB_z$, wherein M and N are independently selected from elements from group 8, 9, 10, 11, 12, 13 or 14 of the periodic table, e.g. but not limited to Fe, Co, Ni, Pt, Cu, Zn, Cd, Al, Ga, In, Ge, Sn or Pb, and A and B are independently selected from elements from group 10, 11, 13, 15 or 16 from the periodic table, e.g. but not limited to Pd, Pt, N, P, As, Sb, Ga, O, S, Se or Te, and wherein w, x, y and z can be independently varied between 0 and 1 and their integral multiples under the proviso that the positive charges of the cationic elements equal the negative charges of the anionic elements.

According to a further aspect of the invention, the nanoparticle comprises at least one shell.

According to a further aspect of the invention, the material of the shell is defined by the formula $O_sC_tD_u$, wherein O can be independently chosen from group 8, 9, 10, 11, 12, 13 or 14 from the periodic table, e.g. but not limited to Fe, Co, Ni, Pt, Cu, Zn, Cd, Al, Ga, In, Ge, Sn or Pb, and C and D can be independently chosen from group 10, 11, 15 or 16 from the periodic table, e.g. but not limited to Pd, Pt, N, P, As, Sb, O, S, Se or Te, and wherein s, t and u can be independently varied between 0 and 1 and their integral multiples under the proviso that the positive charges of the cationic elements equal the negative charges of the anionic elements and under the proviso that the compositions of $M_wN_xA_yB_z$ and $O_sC_tD_u$ are not identical.

According to a further aspect of the invention, the micelle forming elements include block co-polymers, especially amphiphilic block co-polymers.

According to a further aspect of the invention, the block co-polymers comprise at least two different polymer blocks of different compatibility towards solvents.

According to a further aspect of the invention, the amphiphilic block co-polymers are linear or branched or star-shaped or dendritic.

According to a further aspect of the invention, the micelle is formed in the non-aqueous solution and the non-aqueous solution is chosen from at least one of:
- unbranched, branched or cyclic alkanes, optionally bearing one or more halogen atoms, like pentane, hexane, iso-hexanes, cyclopentane, cyclohexane, dichloromethane, chloroform, 1,1-dichloroethane, or 1,2-dichloroethane;
- halogenated alkenes, like 1,1-dichloroethene or all isomers of 1,2-dichloroethene; optionally alkylated aromatic or heteroaromatic solvents, optionally bearing one or more halogen atoms, e.g., benzene, toluene, ethyl benzene, xylenes, chloro benzene, pyridine, collidines or lutidines;
- unbranched, branched or cyclic ethers, like diethyl ether, diisopropyl ether, methyl t-butyl ether, tetrahydrofuran or 1,4-dioxane;
- carbonyl compounds, in particular ketones like acetone, methyl ethyl ketone, cylopentanone or cyclohexanone;
- carboxylic acid esters, e.g. ethyl acetate and the like, unbranched or branched $C_1$-$C_5$ alkanols, like methanol, ethanol, n-propanol, i-propanol, or all isomers of butanol and pentanol;
- polyols, like ethylene glycol, 1,2-propanediol, 1,3-propanediol, glycerol, 1,2-butanediol, 1,3-butanediol, 1,4-butanediol, 1,2,4-butanetriol, diethylene glycol (DEG);
- ethers of polyols, e.g. 2-methoxyethanol, bis-(2-methoxyethyl) ether (diglyme);
- esters of polyols, e.g. diacetoxyethane;
- carboxylic acids, like formic acid, acetic acid, propanoic acid, lactic acid;
- dialkyl sulfoxides, e.g. dimethyl sulfoxide (DMSO);
- carboxylic acid amides, e.g. formamide, acetamide, N-methyl formamide, N-methyl acetamide, N,N-dimethyl formamide (DMF), N,N-dimethyl acetamide (DMA), or N-methyl pyrrolidone (NMP);
- phosphoric acid amides e.g. hexamethyl phosphoric acid triamide (HMPA);
- urea based solvents like 1,3-dimethyl-3,4,5,6-tetrahydro-2(1H)-pyrimidinone (DMPU), 1,3-dimethyl-2-imidazolidinone (DMI), or tetramethyl urea (TEMUR);
- lower alkylnitriles like acetonitrile, propionitrile or butyronitrile;
- ionic liquids, e.g. ammonium-based ionic liquids;
- imidazolium based ionic liquids like 1-allyl-3-methylimidazolium, 1-benzyl-3-methylimidazolium, 1-butyl-2,3-dimethylimidazolium, 1-butyl-3-methylimidazolium, 1-decyl-3-methylimidazolium, 1,3-didecyl-2-methylimidazolium, 1,3-dimethylimidazolium, 1,2-dimethyl-3-propylimidazolium, 1-dodecyl-3-methylimidazolium, 1-ethyl-2,3-dimethylimidazolium, 1-ethyl-3-methylimidazolium, 1-hexadecyl-3-methylimidazolium, 1-hexyl-3-methylimidazolium, 1-(2-hydroxyethyl)-3-methylimidazolium, 1-methyl-3-octadecylimidazolium, 1-methyl-3-octylimidazolium, 1-methyl-3-propylimidazolium salts, preferably with complex anions like e.g. tetrafluoroborate; piperidinium-based ionic liquids, like 1-butyl-1-methylpiperidinium, 1-methyl-1-propylpiperidinium;
- pyridinium-based ionic liquids, 1-alkyl-2-methylpyridinium, 1-alkyl-3-methylpyridinium, 1-alkyl-4-methylpyridinium, 1-butylpyridinium, 1-propylpyridinium, 1-ethylpyridinium, 1-hexylpyridinium salts, preferably with complex anions like e.g. tetrafluoroborate;
- pyrrolidinium-based ionic liquids, e.g. 1-butyl-1-methylpyrrolidinium, 1-ethyl-1-methylpyrrolidinium, 1-methyl-1-propylpyrrolidinium salts, preferably with complex anions, and combinations or combinations of mixtures thereof.

According to a further aspect of the invention, the non-aqueous solution comprises at least partially a water miscible non-aqueous solvent and/or wherein the non-aqueous solution comprises a non-aqueous solvent, which does not form azeotropic phases with water.

According to a further aspect of the invention, the water miscible non-aqueous solvent has a higher boiling point than water.

16. The composition according to claim 14 or claim 15, wherein the micelle is not formed in the non-aqueous solution and the non-aqueous solvent is chosen from at least one of
- dialkyl sulfoxides, e.g. dimethyl sulfoxide (DMSO);
- carboxylic acid amides, e.g. formamide, acetamide, N-methyl formamide, N-methyl acetamide, N,N-dimethyl formamide (DMF), N,N-dimethyl acetamide (DMA), or N-methyl pyrrolidone (NMP);
- phosphoric acid amides e.g. hexamethyl phosphoric acid triamide (HMPA);
- urea based solvents like 1,3-dimethyl-3,4,5,6-tetrahydro-2(1H)-pyrimidinone (DMPU), 1,3-dimethyl-2-imidazolidinone (DMI), or tetramethyl urea (TEMUR);
- 1,4-dioxane; higher alkanols, e.g. 1-butanol;
- polyols, like ethylene glycol, 1,2-propanediol, 1,3-propanediol, glycerol, 1,2-butanediol, 1,3-butanediol, 1,4-butanediol, 1,2,4-butanetriol, diethylene glycol (DEG);
- ethers of polyols, e.g. 2-methoxyethanol, bis-(2-methoxyethyl) ether (diglyme);
- esters of polyols, e.g. diacetoxyethane;
- carboxylic acids, like formic acid, acetic acid, propanoic acid, lactic acid;
- primary, secondary and tertiary amines, diamines or triamines bearing branched, unbranched or cyclic alky groups on the nitrogen atoms and being liquids at ambient temperature;
- cyclic or bicyclic amines, optionally bearing further heteroatoms, selected from N, O, or S in the ring, like piperidine, N-methyl piperidine, morpholine, N-methyl morpholine;
- annelated amidine bases, like 1,5-diazabicyclo(4.3.0)non-5-ene (DBN) or 1,8-diazabicyclo[5.4.0]undec-7-ene (DBU);
- optionally alkylated pyridines, e.g. pyridine, all isomers of picoline, lutidine and collidine;
- C1-2 nitro alkanes; ionic liquids, e.g. ammonium-based ionic liquids;
- imidazolium based ionic liquids like 1-allyl-3-methylimidazolium, 1-benzyl-3-methylimidazolium, 1-butyl-2,3-dimethylimidazolium, 1-butyl-3-methylimidazolium, 1-decyl-3-methylimidazolium, 1,3-didecyl-2-methylimidazolium, 1,3-dimethylimidazolium, 1,2-dimethyl-3-propylimidazolium, 1-dodecyl-3-methylimidazolium, 1-ethyl-2,3-dimethylimidazolium, 1-ethyl-3-methylimidazolium, 1-hexadecyl-3-methylimidazolium, 1-hexyl-3-methylimidazolium, 1-(2-hydroxyethyl)-3-methylimidazolium, 1-methyl-3-octadecylimidazolium, 1-methyl-3-octylimidazolium, 1-methyl-3-propylimidazolium salts, preferably with complex anions like e.g. tetrafluoroborate;
- piperidinium-based ionic liquids, like 1-butyl-1-methylpiperidinium, 1-methyl-1-propylpiperidinium;

pyridinium-based ionic liquids, 1-alkyl-2-methylpyridinium, 1-alkyl-3-methylpyridinium, 1-alkyl-4-methylpyridinium, 1-butylpyridinium, 1-propylpyridinium, 1-ethylpyridinium, 1-hexylpyridinium salts, preferably with complex anions like e.g. tetrafluoroborate;

pyrrolidinium-based ionic liquids, e.g. 1-butyl-1-methylpyrrolidinium, 1-ethyl-1-methylpyrrolidinium, 1-methyl-1-propylpyrrolidinium salts, preferably with complex anions, which in combination with the cation renders the ionic liquid water miscible, like e.g. tetrafluoroborate, or mixtures of said solvents.

According to a further aspect of the invention, at least one of the micelle forming and/or cross-linking elements includes thiol.

Also, the invention relates to a conjugation of a composition to a biomolecule or a plurality of biomolecules.

Additionally, the present invention provides the use of a composition for a biological event or biological application. The composition is a composition as specified above and hereinafter, in particular a composition, comprising at least one micelle in non-aqueous solution, wherein the micelle encapsulates one or more nanoparticles. Also, the use relates to the use of the disclosed embodiments of the composition. All functional and structural features and the advantages thereof, of the composition and its possible embodiments, can be also achieved and realized with the use of the composition.

Moreover, the present invention provides a method for providing a composition comprising at least one micelle in non-aqueous solution, wherein the micelle encapsulates one or more nanoparticles, wherein the micelle encapsulating the one or more nanoparticles is or are formed in the non-aqueous solution. All functional and structural features and the advantages thereof of the composition and its possible embodiments can be also achieved and realized with the method.

Also, the present invention provides a method for providing a composition comprising at least one micelle in non-aqueous solution, wherein the micelle encapsulates one or more nanoparticles, wherein in a first step the micelle encapsulating the one or more nanoparticles is or are formed in a first solution being different from the non-aqueous solution and wherein in a second step the first solution is replaced by the non-aqueous solution. All functional and structural features and the advantages thereof of the composition and its possible embodiments can be also achieved and realized with the method.

DETAILED DESCRIPTION OF THE PRESENT INVENTION

Definitions

Figure 1:
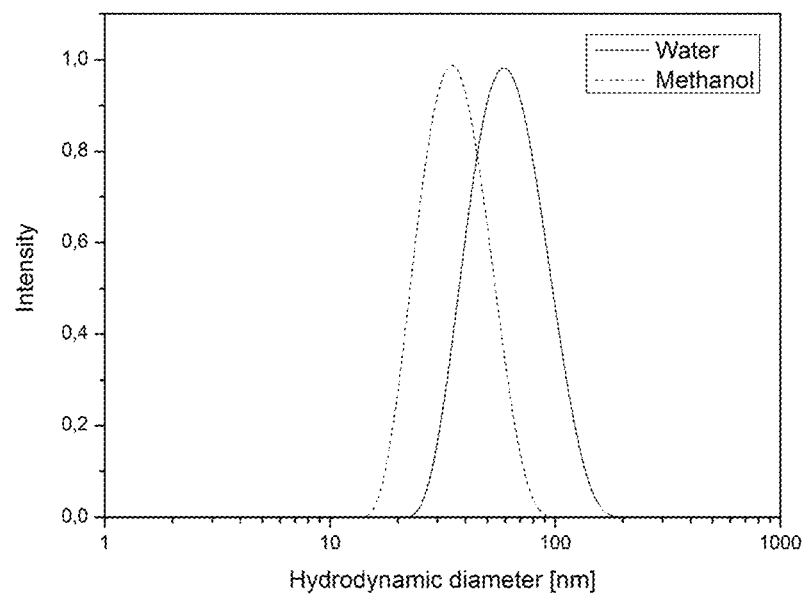
FIG. 1 shows DLS-Data for micellar encapsulated nanoparticles in methanol and water.

In particular, the present invention relates to nanoparticles, possessing superparamagnetic, plasmonic, or fluorescent properties, including semiconductor nanoparticles, metallic nanoparticles, oxidic nanoparticles, or rare earth doped nanoparticles encapsulated in micelles in non-aqueous solutions.

Nanoparticles within the scope of the invention are spatial objects, which have dimensions of 1 to 1000 nm in at least one dimension. Said nanoparticles may occur as solid particles, as well as hollow structures in various shapes, which include, but are not restricted to, spherical, elongated, i.e. rod-like, elliptical, egg-like, dumbbell-shaped, circular or torus-like, cubic or cuboid, prismatic or cylindrical shapes, regularly or irregularly multi-faceted geometrical bodies, polygonal plates of e.g. triangular, square, or hexagonal shapes, leaflets, multi-armed or star-shaped bodies, e.g. tetrapods, or wire-like shapes, and the like. Said nanoparticles may be optionally shielded with at least one shell comprised of a different material than the core.

The term "nanoparticle" is inter alia also covering the term "nano-crystal" or "ultra-small particle".

Before the present invention is described in detail, it is to be understood that this invention is not limited to the particular methodology, devices, or compositions described, as such methods, devices, or compositions can, of course, vary. It is also to be understood that the terminology used herein is for the purpose of describing particular embodiments only, and is not intended to limit the scope of the present invention.

Use of the singular forms "a," "an," and "the" include plural references unless the context clearly dictates otherwise. Thus, for example, reference to "a cell" includes a plurality of cells, reference to "a nanoparticle" includes a plurality of such nanoparticles, reference to "an biomolecule" like i.e. DNA, protein, peptide, carbohydrate or the like includes the plurality of biomolecules, and the like.

Unless defined otherwise or the context clearly dictates otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

All publications mentioned herein are hereby incorporated by reference for the purpose of disclosing and describing the particular materials and methodologies for which the reference was cited. The publications discussed herein are provided solely for their disclosure prior to the filing date of the present application. Nothing herein is to be construed as an admission that the invention is not entitled to antedate such disclosure by virtue of prior invention.

In describing the present invention, the following terms will be employed, and are intended to be defined as indicated below.

The term "nanoparticle" refers to a particle, generally a semiconductor particle, or a nanocrystalline non-semiconductor-based particle, in particular, a lanthanide-doped metal oxide particle or lanthanide-doped salt-like particle, or an oxidic or a metallic particle, having a diameter in the range of about 1 nm to about 1000 nm, preferably in the range of about 2 nm to about 50 nm, more preferably in the range of about 2 nm to about 20 nm (for example about 2, 3, 4, 5, 6, 7, 8, 9, 10, 11, 12, 13, 14, 15, 16, 17, 18, 19, or 20 nm).

The terms "semiconductor nanocrystal" and "quantum dot", "quantum rod", quantum dot rod" or the acronyms QD, QDs, QR, QRs, QDR, QDRs, SCNC or SCNCs are used interchangeably herein to refer to semiconductor nanoparticles composed of an inorganic crystalline material that is luminescent (i.e., they are capable of emitting 'electromagnetic radiation upon excitation), and include an inner core of one or more first semiconductor materials that is optionally contained within an overcoating or "shell" of a second semiconductor material. A semiconductor nanocrystal core surrounded by a semiconductor shell is referred to as a "core/shell" semiconductor nanocrystal.

Semiconductors are especially defined by their electrical conductivity, which lies between the one of a conductor and the one of an insulator. Semiconductors can be luminescent, but this is not mandatory For example, the surrounding shell material may have a band gap energy that is larger than the band gap energy of the core material and may be chosen to have an atomic spacing close to that of the core substrate.

Suitable semiconductor materials for the core and/or shell may include, but not limited to, the following materials comprised of a first element selected from Groups 2 or 12 of the Periodic Table of the Elements and a second element selected from Group 16 (e.g., ZnS, ZnSe, ZnTe, CdS, CdSe, CdTe, HgS, HgSe, HgTe, MgS, MgSe, MgTe, CaS, CaSe, CaTe, SrS, SrSe, SrTe, BaS, BaSe, BaTe, and the like as well as mixtures thereof); materials comprised of a first element selected from Group 13 of the Periodic Table of the Elements and a second element selected from Group 15 (GaN, GaP, GaAs, GaSb, InN, InP, InAs, InSb, and the like as well as mixtures thereof); materials comprised of a Group 14 element (Ge, Si, and the like as well as mixtures thereof); materials such as PbS, PbSe, PbTe and the like as well as mixtures thereof, materials such as CuInS, CuInGaS and the like as well as mixtures thereof; and alloys and mixtures thereof. As used herein, all reference to the Periodic Table of the Elements and groups thereof is to the new IUPAC system for numbering element groups, as set forth in the Handbook of Chemistry and Physics, 81st Edition (CRC Press, 2000).

An SCNC is optionally surrounded by a "coat" of an organic capping agent. The organic capping agent may be any number of materials, but has an affinity for the SCNC surface. In general, the capping agent can be an isolated organic molecule, a polymer (or a monomer for a polymerization reaction), an inorganic complex, or an extended crystalline structure. The coat can be used to convey solubility, e.g., the ability to disperse a coated SCNC homogeneously into a chosen solvent, functionality, binding properties, or the like. In addition, the coat can be used to tailor the optical properties of the SCNC.

Thus, the terms "semiconductor nanocrystal," "SCNC," and "quantum dot" as used herein include a coated SCNC core, as well as a core/shell SCNC.

"Monodisperse particles" include a population of particles wherein at least about 60% of the particles in the population, more preferably about 75 to about 90, or any integer therebetween, percent of the particles in the population fall within a specified particle size range. A population of monodisperse particles deviates less than 10% rms (root-mean-square) in diameter, and preferably deviates less than 5% rms.

The phrase "one or more sizes of SCNCs" is used synonymously with the phrase "one or more particle size distributions of SCNCs." One of ordinary skill in the art will realize that particular sizes of SCNCs are actually obtained as particle size distributions.

By "luminescence" is meant the process of emitting electromagnetic radiation (light) from an object. Luminescence results when a system undergoes a transition from an excited state to a lower energy state with a corresponding release of energy in the form of a photon. These energy states can be electronic, vibrational, rotational, or any combination thereof. The transition responsible for luminescence can be stimulated through the release of energy stored in the system chemically or added to the system from an external source. The external source of energy can be of a variety of types including chemical, thermal, electrical, magnetic, electromagnetic, and physical, or any other type of energy source capable of causing a system to be excited into a state higher in energy than the ground state. For example, a system can be excited by absorbing at least one photon of light, by being placed in an electrical field, or through a chemical oxidation-reduction reaction. The energy of the photons emitted during luminescence can be in a range from low-energy microwave radiation to high-energy x-ray radiation. Typically, luminescence refers to photons in the range from UV to IR radiation.

"Biomolecule" refers to any kind of molecule used in biological applications, including but not limited to, optionally glycosylated proteins, e.g. antibodies, nanobodies, antibody fragments, like single-chain antibodies, fab fragments, viral proteins, lectins, peptides, including polyaminoacids, nucleic acids, including desoxyribonucleic acids (DNA), ribonucleic acids (RNA, siRNA, miRNA), locked nucleic acid (LNA), aptamers, lipids, steroids, messenger substances, prions, carbohydrates, small molecules and the like.

"Complementary" or "substantially complementary" refers to the ability to hybridize or base pair between nucleotides or nucleic acids, such as, for instance, between the two strands of a double stranded DNA molecule or between a polynucleotide primer and a primer binding site on a single stranded nucleic acid to be sequenced or amplified. Complementary nucleotides are, generally, Adenine [A] and Thymine [T], or A and Uracil [U], or Cytosine [C] and Guanine [G]. Two single-stranded RNA or DNA molecules are said to be substantially complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%.

The term "aptamer" (or "nucleic acid antibody") is used herein to refer to a single- or double-stranded polynucleotide that recognizes and binds to a desired target molecule by virtue of its shape (c.f. e.g., PCT Publication Nos. WO 92/14843, WO 91/19813, and WO 92/05285).

According to the invention, the problems described above are solved by the encapsulation of nanoparticles into micelles in non-aqueous solutions.

The term "encapsulation" refers to micellization as well as to cross-linking a previously formed micelle or micelles.

The term "micelle" may be generally understood as an aggregate of colloidal dimensions of surfactant molecules dispersed in a liquid, and the term surfactant as a surface-active substance, lowering the surface tension of liquid, usually organic compounds that are amphiphilic.

The term "transfection" may be generally understood as the deliberate or also undeliberate introduction of material like the micelle-encapsulated nanoparticles into cells.

The term "labeling" may be generally understood as the deliberate or also underliberate attaching of material like the micelle-encapsulated nanoparticles to a cell or a biological molecule or a biological sample. The material may be e.g. attached onto the cell or into the cell.

Transfection and labeling of a cell or a biological molecule or a biological sample are both examples for a biological application.

The term "biological event" can be defined as including an interaction of biological moieties, a biological process, an alteration in the structures of a biological compound or, an alteration in a biological process.

The term "biological sample" can be defined as a sample of tissue or fluid isolated from an individual, including but not limited to, for example, plasma, serum, spinal fluid, semen, lymph fluid, the external sections of the skin, respiratory, intestinal, and genitourinary tracts, tears, saliva, milk, blood cells, tumors, organs, and also samples of in vitro cell culture constituents (including but not limited to conditioned medium resulting from the growth of cells in cell culture medium, putatively virally infected cells, recombinant cells, and cell components).

In particular, by the present invention a composition is provided, comprising at least one micelle in non-aqueous solution, wherein the micelle encapsulates one or more nanoparticle(s).

The nanoparticles can be monodisperse nanoparticles.

Synthesis of nanoparticles in reverse micelles have been described (F. T. Quinlan, J. Kuther, W. Tremel, W. Knoll, S. Risbud, P. Stroeve; Reverse Micelle Synthesis and Characterization of ZnSe Nanoparticles, *Langmuir* 2000, 16, 4049-4051.) (M.-L. Wu, D.-H. Chen, T.-C. Huang; Synthesis of Au/Pd Bimetallic Nanoparticles in Reverse Micelles, *Langmuir* 2001, 17, 3877-3883.) (Dongbai Zhang, Limin Qi, Jiming Ma, Humin Cheng; Formation of crystalline nano-sized titania in reverse micelles at room temperature, *J. Mater. Chem.*, 2002, 12, 3677-3680), (Christopher E. Bunker et al. Formation of Cadmium Sulfide Nanoparticles in Reverse Micelles: Extreme Sensitivity to Preparation Procedure, *Langmuir* 2004, 20, 5642-5644), however the formation of micelles around freely dispersed pre-formed nanoparticles in non-aqueous solvents is novel. Surprisingly, the micellar compositions of said nanoparticles thus obtained, maintain their integrity and properties when transferred into different non-aqueous and aqueous solvents. Furthermore it was found that polymer micelles containing nanoparticles in an aqueous preparation can be transferred into non-aqueous solutions by removing the water, virtually without impairing their properties.

Within the scope of the invention, nanoparticles suitable for the encapsulation in micelles in non-aqueous solutions may bear a hydrophobic surface originating from said growth process.

Said nanoparticles as derived from their growth solution may occur as solid particles, as well as hollow structures in various shapes, which include, but are not restricted to, spherical, rod-like, elliptical, egg-like, circular or torus-like, cubic or cuboid, or cylindrical shapes, regularly or irregularly multi-faceted geometrical bodies, polygonal plates of e.g. triangular, square, or hexagonal shapes, multi-armed or star-shaped bodies, e.g. tetrapods, wire-like shapes, and the like.

Said nanoparticles may exhibit characteristic physicochemical attributes on interacting with their environment, e.g. absorbance of parts of the electromagnetic spectrum and fluorescence emission on excitation with parts of the electromagnetic spectrum, magnetism, paramagnetism, superparamagnetism, plasmon resonance, Raman-Effect enhancement or combinations of said properties.

Nanoparticles within the scope of the invention may include, but are not limited to semiconductor quantum dots or quantum rods, or combinations thereof; salt-like lattices, e.g. phosphates, vanadates, wolframates, fluorides, oxychlorides and the like; metals, including gold and silver, or metal oxides, e.g. iron oxides in various modifications.

Said semiconductor nanoparticles may be e.g. described by the formula $M_wN_xA_yB_z$, wherein M and N are independently selected from elements from group 8, 9, 10, 11, 12, 13 or 14 of the periodic table, e.g. but not limited to Fe, Co, Ni, Pt, Cu, Zn, Cd, Al, Ga, In, Ge, Sn or Pb, and A and B are independently selected from elements from group 10, 11, 13, 15 or 16 from the periodic table, e.g. but not limited to Pd, Pt, N, P, As, Sb, Ga, O, S, Se or Te, and wherein w, x, y and z can be independently varied between 0 and 1 and their integral multiples under the proviso that the positive charges of the cationic elements equal the negative charges of the anionic elements.

Said semiconductor nanoparticles may be optionally shielded by at least one shell comprising the formula $O_sC_tD_u$, wherein O can be independently chosen from group 8, 9, 10, 11, 12, 13 or 14 from the periodic table, e.g. but not limited to Fe, Co, Ni, Pt, Cu, Zn, Cd, Al, Ga, In, Ge, Sn or Pb, and C and D can be independently chosen from group 10, 11, 15 or 16 from the periodic table, e.g. but not limited to Pd, Pt, N, P, As, Sb, O, S, Se or Te, and wherein s, t and u can be independently varied between 0 and 1 and their integral multiples under the proviso that the positive charges of the cationic elements equal the negative charges of the anionic elements and under the provisio that the compositions of $M_wN_xA_yB_z$ and $O_sC_tD_u$ are not identical.

In another embodiment said semiconductor nanoparticles may be e.g. described by the formula $M_xN_{1-x}A_yB_{1-y}$, wherein M and N are independently selected from elements from group 8, 9, 10, 11, 12, 13 or 14 of the periodic table, e.g. but not limited to Fe, Co, Ni, Pt, Cu, Zn, Cd, Al, Ga, In, Ge, Sn or Pb, and A and B are independently selected from elements from group 10, 11, 15 or 16 from the periodic table, e.g. but not limited to Pd, Pt, N, P, As, Sb, O, S, Se or Te, and wherein x and y can be independently varied between 0 and 1.

Said semiconductor nanoparticles may be optionally shielded by at least one shell comprising the formula $O_1C_zD_{1-z}$, wherein O can be independently chosen from group 8, 9, 10, 11, 12, 13 or 14 from the periodic table, e.g. but not limited to Fe, Co, Ni, Pt, Cu, Zn, Cd, Al, Ga, In, Ge, Sn or Pb, and C and D can be independently chosen from group 10, 11, 15 or 16 from the periodic table, e.g. but not limited to Pd, Pt, N, P, As, Sb, O, S, Se or Te, and wherein z may independently assume a value between 0 and 1 under the proviso that the compositions of $M_xN_{1-x}A_yB_{1-y}$ and $O_1C_zD_{1-z}$ are not identical.

Each of the structural components of all embodiments, i.e. core or shells can be optionally doped by heavy-metal ions like Ag, Cu, Co, or Mn, thus comprising at least one said heavy-metal atom per nanoparticle.

Typical compositions may include but are not limited to ZnS, ZnSe, ZnTe, CdS, CdSe, CdTe, HgS, HgSe, HgTe, MgS, MgSe, MgTe, CaS, CaSe, CaTe, SrS, SrTe, BaS, BaSe, BaTe, GaN, GaP, GaAs, GaSb, InN, InP, InAs, InSb, Ge, Si, PbS, Pb Se, PbTe, CuInS, CuInGaS and an alloy or mixture thereof.

Said shells may independently emulate the shape of the core particle, or may be of different shapes. Exemplarily, if the core is spherical, elongated or tripod-, tetrapod-, hexapod-, octapod- or star-shaped, a core/shell particle may be comprised of core(spherical)/shell(spherical), core(elongated)/shell(elongated), core(spherical)/shell(elongated), core(spherical)/shell(tetrapod). Exemplarily, a core/shell/shell nanoparticle may be comprised of core(spherical)/shell(spherical)/shell(spherical), core(spherical)/shell(spherical)/shell(elongated), core(spherical)/shell(spherical)/shell(tetrapod), core(spherical)/shell(elongated)/shell(elongated), core(elongated)/shell(elongated)/shell(elongated). Exemplarily, a core/shell/shell/shell nanoparticle may be comprised of core(spherical)/shell(spherical)/shell(spherical)/shell(spherical), core(spherical)/shell(spherical)/shell(spherical)/shell(elongated), core(spherical)/shell(spherical)/shell(elongated)/shell(elongated), core(spherical)/shell(elongated)/shell(elongated)/shell(elongated), core(elongated)/shell(elongated)/shell(elongated)/shell(elongated).

Said rare earth doped nanoparticles may exhibit optionally luminescent and/or paramagnetic properties.

Said luminescent rare earth doped nanoparticles are particles wherein a core is comprised of a first metal salt or oxide, which—after excitation—is suited to transfer the excitation energy to a second luminescent metal salt, or to a plurality of luminescent metal salts, which emits said excitation energy as luminescence.

Luminescent nanoparticles are comprised of a core and optionally shielded by at least one shell, wherein the core metal and the shell metal are selected from the elements Ce (58), Pr (59), Nd (60), Sm (62), Eu (63), Gd (64), Tb (65), Dy (66), Ho (67), Er (68), Tm (69) or Yb (70).

Specific examples of luminescent shell materials are for instance LiI:Eu; NaI:Tl; CsI:Tl; CsI:Na; LiF:Mg; LiF:Mg, Ti; LiF:Mg,Na; KMgF$_3$: Mn; BaFCl:Eu; BaFCl:Sm; BaFBr:Eu; BaFCl$_{0.5}$Br$_{0.5}$:Sm; BaY$_2$F$_8$:A (A=Pr, Tm, Er, Ce); BaSi$_2$O$_5$:Pb; BaMg$_2$Al$_{16}$O$_{27}$:Eu; BaMgAl$_{14}$O$_{23}$:Eu; BaMgAl$_{10}$O$_{17}$:Eu; BaMgAl$_2$O$_3$:Eu; Ba$_2$P$_2$O$_7$:Ti; (Ba,Zn, Mg)$_3$Si$_2$O$_7$:Pb; Ce(Mg,Ba)Al$_{11}$O$_{19}$; Ce$_{0.65}$Tb$_{0.35}$MgAl$_{11}$O$_{19}$:Ce,Tb; MgAl$_{11}$O$_{19}$:Ce,Tb; MgF$_2$:Mn; MgS:Eu; MgS:Ce; MgS:Sm; MgS:(Sm,Ce); (Mg,Ca)S:Eu; MgSiO$_3$:Mn; 3,5MgO.0,5MgF$_2$.GeO$_2$:Mn; MgWO$_4$:Sm; MgWO$_4$:Pb; 6MgO.As$_2$O$_5$:Mn; (Zn,Mg) F$_2$:Mn; (Zn$_4$Be) SO$_4$:Mn; Zn$_2$SiO$_4$:Mn; Zn$_2$SiO$_4$:Mn,As; Zn$_3$(PO$_4$)$_2$:Mn; CdBO$_4$:Mn; CaF$_2$:Mn; CaF$_2$:Dy; CaS:A (A=Lanthanide, Bi); (Ca,Sr)S:Bi; CaWO$_4$:Pb; CaWO$_4$:Sm; CaSO$_4$:A (A=Mn, lanthanide); 3Ca$_3$(PO$_4$)$_2$.Ca(F,Cl)$_2$:Sb,Mn; CaSiO$_3$:Mn,Pb; Ca$_2$Al$_2$Si$_2$O$_7$:Ce; (Ca,Mg)SiO$_3$:Ce; (Ca, Mg)SiO$_3$:Ti; 2SrO.6(B$_2$O$_3$).SrF$_2$Eu; 3 Sr$_3$(PO$_4$)$_2$.CaCl$_2$:Eu; A$_3$(PO$_4$)$_2$.ACl$_2$:Eu (A=Sr, Ca, Ba); (Sr,Mg)$_2$P$_2$O$_7$:Eu; (Sr, Mg)$_3$(PO$_4$)$_2$:Sn; SrS:Ce; SrS:Sm,Ce; SrS:Sm; SrS:Eu; SrS:Eu,Sm; SrS:Cu,Ag; Sr$_2$P$_2$O$_7$:Sn; Sr$_2$P$_2$O$_7$:Eu; Sr$_4$Al$_{14}$O$_{25}$:Eu; SrGa$_2$S$_4$:A (A=lanthanide, Pb); SrGa$_2$S$_4$:Pb; Sr$_3$Gd$_2$Si$_6$O$_{18}$:Pb, Mn; YF$_3$:Yb, Er; YF$_3$:Ln (Ln=lanthanide); YLiF$_4$:Ln (Ln=lanthanide); Y$_3$Al$_5$O$_{12}$:Ln (Ln=lanthanide); YAl$_{13}$(BO$_4$)$_3$:Nd, Yb; (Y,Ga)BO$_3$:Eu; (Y,Gd)BO$_3$:Eu; Y$_2$Al$_3$Ga$_2$O$_{12}$:Tb; Y$_2$SiO$_5$:Ln (Ln=lanthanide); Y$_2$O$_2$S:Ln (Ln=lanthanide); YVO$_4$:A (A=lanthanide, In); Y(P,V)O$_4$:Eu; YTaO$_4$:Nb; YAlO$_3$:A (A=Pr, Tm, Er, Ce); YOCl:Yb,Er; LnPO$_4$:Ce,Tb (Ln=lanthanide or mixture of lanthanides); LuVO$_4$:Eu; GdVO$_4$:Eu; Gd$_2$O$_2$S:Tb; GdMgB$_5$O$_{10}$:Ce,Tb; LaOBr:Tb; La$_2$O$_2$S:Tb; LaF$_3$:Nd,Ce; BaYb$_2$F$_8$:Eu; NaYF$_4$:Yb,Er; NaYF$_4$:Yb,Tm, NaGdF$_4$:Yb,Er; NaGdF$_4$:Yb,Tm, NaLaF$_4$:Yb,Er; NaLaF$_4$:Yb,Tm, LaF$_3$:Yb,Er,Tm; BaYF$_3$:Yb,Er; GaN:A (A=Pr, Eu, Er, Tm); Bi$_4$Ge$_3$O$_{12}$; LiNbO$_3$:Nd,Yb; LiNbO$_3$:Er; LiCaAlF$_6$:Ce; LiSrAlF$_6$:Ce; LiLuF$_4$:A (A=Pr, Tm, Er, Ce); $Li_2B_4O_7$:Mn, $Y_2O_2S$:Eu, $Y_2SiO_5$:Eu, $CaSiO_3$: Ln, CaS:Ln, wherein Ln=one, two or more lanthanides as well as mixtures thereof.

If classified according to the host lattice type the following preferred embodiments can also be enumerated.

1. Halides: for instance $XY_2$ (X=Mg, Ca, Sr, Ba; Y=F, Cl, I), CaF:Eu (II), BaF:Eu; $BaMgF_4$:Eu; $LiBaF_3$:Eu; $SrF$:Eu; $SrBaF_2$Eu; $CaBr_2$:Eu—$SiO_2$; $CaCl_2$:Eu; $CaCl_2$:Eu—$SiO_2$; $CaCl_2$:Eu,Mn—$SiO_2$; $CaI_2$:Eu; $CaI_2$:Eu, Mn; $KMgF_3$:Eu; $SrF_2$:Eu (II), $BaF_2$:Eu (II), $YF_3$, $NaYF_4$; MgF2:Mn; MgF2: Ln (Ln=lanthanide (s)) as well as mixtures thereof.

2. Earth alkaline sulfates: for instance $XSO_4$ (X=Mg, Ca, Sr, Ba), $SrSO_4$:Eu, $SrSO_4$:Eu,Mn, $BaSO_4$:Eu, $BaSO_4$:Eu, Mn, $CaSO_4$, $CaSO_4$:Eu, $CaSO_4$:Eu,Mn, as well as mixed earth alkaline sulfates, also in combination with magnesium, e.g. $Ca,MgSO_4$:Eu,Mn as well as mixtures thereof.

3. Phosphates and halophosphates: for instance $CaPO_4$:Ce, Mn, $Ca_5(PO_4)_3Cl$:Ce,Mn, $Ca_5(PO_4)_3F$:Ce,Mn, $SrPO_4$:Ce, Mn, $Sr_5(PO_4)_3Cl$:Ce,Mn, $Sr_5(PO_4)_3F$:Ce,Mn, the latter also codoped with Eu (II) or codoped with EU,Mn, $\alpha$-$Ca_3(PO_4)_2$: Eu; $\beta$-$Ca_3(PO_4)_2$:Eu,Mn; $Ca_5(PO_4)_3Cl$:Eu; $Sr_5(PO_4)_3Cl$:Eu; $Ba_{10}(PO_4)_6Cl$:Eu; $Ba_{10}(PO_4)_6Cl$:Eu,Mn, $Ca_2Ba_3(PO_4)_3Cl$: Eu; $Ca_5(PO_4)_3F$:$Eu^{2+}X^{3+}$; $Sr_5(PO_4)_3F$:$Eu^{2+}X^{3+}$ (X=Nd, Er, Ho, Tb); $Ba_5(PO_4)_3Cl$:Eu; $\beta$-$Ca_3(PO_4)_2$:Eu; $CaB_2P_2O_9$:Eu; $Ca_2P_2O_7$:Eu; $Ca_2P_2O_7$:Eu, Mn; $Sr_{10}(PO_4)_6Cl$:Eu; (Sr, Ca, Ba, $Mg)_{10}(PO_4)_6Cl$:Eu; $LaPO_4$:Ce; $CePO_4$; $LaPO_4$:Eu, $LaPO_4$:Ce, $LaPO_4$:Ce,Tb, $CePO_4$:Tb as well as mixtures thereof.

4. Borates: for instance $LaBO_3$; $LaBO_3$:Ce; $ScBO_3$:Ce; $YAlBO_3$:Ce; $YBO_3$:Ce; $Ca_2B_5O_9Cl$:Eu; $xEuO.yNa_2O.zB_2O_3$ as well as mixtures thereof.

5. Vanadates: for instance $YVO_4$, $YVO_4$:Eu, $YVO_4$:Dy, $YVO_4$:Sm; $YVO_4$:Bi; $YVO_4$:Bi,Eu, $YVO_4$:Bi,Dy, $YVO_4$:Bi, Sm; $YVO_4$:Tm, $YVO_4$:Bi,Tm $GdVO_4$, $GdVO_4$:Eu, $GdVO_4$: Dy, $GdVO_4$:Sm $GdVO_4$:Bi; $GdVO_4$:Bi,Eu, $GdVO_4$:Bi,Dy, $GdVO_4$:Bi,Sm; $Gd(PV)O_4$, $Gd(PV)O_4$:Eu, $Gd(PV)O_4$:Dy, $Gd(PV)O_4$:Sm $Gd(PV)O_4$:Bi; $Gd(PV)O_4$:Bi,Eu, $Gd(PV)O_4$: Bi,Dy, $Gd(PV)O_4$:Bi,Sm as well as mixtures thereof.

6. Aluminates: for instance $MgAl_2O_4$:Eu; $CaAl_2O_4$:Eu; $SrAl_2O_4$:Eu; $BaAl_2O_4$:Eu; $LaMgAl_{11}O_{19}$:Eu; $BaMgAl_{10}O_{17}$:Eu; $BaMgAl_{10}O_{17}$:Eu, Mn; $CaAl_{12}O_{19}$:Eu; $SrAl_{12}O_{19}$:Eu; $SrMgAl_{10}O_{17}$:Eu; $Ba(Al_2O_3)_6$:Eu; (Ba, Sr)$MgAl_{10}O_{17}$:Eu,Mn; $CaAl_2O_4$:Eu, Nd; $SrAl_2O_4$:Eu, Dy; $Sr_4Al_{14}O_{25}$:Eu, Dy as well as mixtures thereof.

7. Silicates: for instance $BaSrMgSi_2O_7$:Eu; $Ba_2MgSiO_7$:Eu; $BaMg_2Si_2O_7$:Eu; $CaMgSi_2O_6$:Eu; $SrBaSiO_4$:Eu; $Sr_2Si_3O_8.SrCl_2$:Eu; $Ba_2SiO_4Br_6$:Eu; $Ba_2SiO_4Cl_6$:Eu; $Ca_2MgSi_2O_7$:Eu; $CaAl_2Si_2O_8$:Eu; $Ca_{1.5}Sr_{0.5}MgSi_2O_7$:Eu; $(Ca,Sr)_2MgSi_2O_7$:Eu, $Sr_2LiSiO_4F$:Eu as well as mixtures thereof.

8. Tungstates and molybdates: for instance $X_3WO_6$ (X=Mg, Ca, Sr, Ba); $X_2WO_4$ (X=Li, Na, K, Rb, Cs), $XMoO_4$ (X=Mg, Ca, Sr, Ba) as well as polymolybdates oder polytungstates or the salts of the corresponding hetero- or isopolyacids as well as mixtures thereof.

9. Germanates: e.g. $Zn_2GeO_4$.

10. Moreover the following classes: $ALnO_2$:Yb, Er (A=Li, Na; Ln=Gd, Y, Lu); $LnAO_4$:Yb,Er (Ln=La, Y; A=P, V, As, Nb); $Ca_3Al_2Ge_3O_{12}$:Er; $Gd_2O_2S$:Yb, Er; $La_2SYb$, Er as well as mixtures thereof.

Transferring micelle preparations from an aqueous environment into a non-aqueous environment normally results in a deterioration of structural integrity and physico chemical properties of the micelle, because the entropic gain from the release of water molecules during micelle formation is lost. As an example, aqueous micelle preparations of a surfactant, e.g. sodium dodecyl sulfate (SDS) decompose, when transferred to methanol, or even do not constitute when SDS is mixed with methanol (G. D. Parfitt and J. A. Wood "Light scattering of sodium dodecyl sulphate in methanol-water mixtures", Kolloid-Zeitschrift and Zeitschrift für Polymere, January 1969, Volume 229, Issue 1, pp 55-60).

It has been demonstrated that block copolymers comprised of at least two polymer blocks of different compatibility with respect to a given solvent, may form micellar structures in non-aqueous solvents (S. Hou et al., Langmuir 2003, 19, 2485-2490; B. C. Kumi et al., Journal of Colloid and Interface Science 386 (2012) 212-217; P. Alexandridis, Macromolecules 1998, 31, 6935-6942; ibid. Macromolecules 2000, 33, 3382-3391). However, said preparations of polymer micelles in non-aqueous solution showed a lower aggregation number and higher critical micelle concentration (CMC) compared to the aqueous preparation, and hence showed reduced stability. Most obviously, said polymer micelles did not contain any particles.

Surprisingly, application of the invention described herein, revealed that the physico chemical properties of said nanoparticles exemplarily were much better maintained than in an aqueous preparation, as could be demonstrated by preparation of a stable non-aqueous composition of otherwise highly damageable CdSeTe/CdS nanoparticles. Moreover, said composition in a water miscible solvent could be freely transferred into aqueous solutions without compromising the physico-chemical properties, i.e. fluorescence.

Hence, the present invention describes compositions of micellar enclosed nanoparticles in non-aqueous solvents, methods of preparation and uses, which avoid the shortcomings of aqueous compositions mentioned above.

Furthermore, it was found that micellar encapsulated nanoparticles can be transferred from an aqueous preparation of said nanoparticles into various non-aqueous solvents, completely maintaining structural integrity and physico chemical properties of said nanoparticles, hence fully leveraging on the benefits offered by non-aqueous preparations as pointed out above.

First Aspect of the Present Invention

In a first aspect of the present invention, the micellar encapsulation of hydrophobic nanoparticles may be achieved under completely anhydrous conditions, using combinations of said nanoparticles and said micelle forming unimers in mixtures of intermiscible non-aqueous solvents.

In other words, a method is provided for providing a composition comprising at least one micelle in non-aqueous solution, wherein the micelle encapsulates one or more nanoparticle(s), wherein the micelle encapsulating the one or more nanoparticle(s) is or are formed in the non-aqueous solution.

For instance, nanoparticles, in particular said nanoparticles above, may be co-dissolved with said micelle forming unimers in at least one intermiscible non-aqueous solvent compatible with the hydrophobic domains of said micelle forming unimers and transferred into at least one non-aqueous solvent of reduced compatibility with regard to said unimers.

The micelle forming elements or unimers may include block co-polymers (e.g. amphiphilic block co-polymers), comprised of at least two different polymer blocks of different compatibility towards solvents.

Said selected copolymers may be comprised of the elements selected from C, H, O, N, Si, S, P, X, wherein X represents a halogen selected from the elements F, Cl and Br.

Said block co-polymers may be comprised of about 1 to about 99% by mole fraction of a polymer block incompatible with the other polymer blocks said block co-polymer is comprised of.

An example, which should in no way construed to limit the invention, is a block co-polymer comprised of a block of polystyrene (PS) and polyisoprene (PI), which displays said micelle forming properties, due to the incompatibility of said PS- and PI-block in non-aqueous solvents.

Said block co-polymers may be linear, branched, brush-like, star-shaped or dendritic.

Said block co-polymers may display amphiphilic properties. Furthermore, said amphiphilic block copolymers may be comprised of about 1 to about 99% by mole fraction of hydrophobic segments and about 99 to about 1 mole fraction % of hydrophilic segments.

Hydrophilic segments may be selected from the group consisting of polyethers in particular polyethylene glycol, which is synonymously called polyethylene oxide, polyacetals, polyamides, polylactones, polyimides including poly-2-oxazolines, polyamines, including polyethylene imine and polyallyl amine polylactams, polymaleic acids, polymaleic amides, polymaleic imides, hydrophilic polymaleic esters, polyacrylic acid, polyacrylic amides, hydrophilic polyacrylates, polymethacrylic acid, polymethacrylic amides, hydrophilic polymethacrylates like poly(hydroxyethyl methacrylate), poly-N-vinyl-2-pyrrolidone, poly-N-vinyl-2-piperidone, poly-N-vinyl-2-caprolactam, poly-N-vinyl-3-methyl-2-caprolactam, poly-N-vinyl-3-methyl-2-piperidone, poly-N-vinyl-4-methyl-2-piperidone, poly-N-vinyl-4-methyl-2-caprolactam, poly-N-vinyl-3-ethyl-2-pyrrolidone, and poly-N-vinyl-4,5-dimethyl-2-pyrrolidone, polyvinylimidazole, poly-N—N-dimethylacrylamide, poly-N-vinyl-N-methylacetamide, polyvinyl alcohol, polyurethanes, polyureas, and biopolymers including amino acid polymers like polylysines, polyhistidines, polyglycines, polyglutamic acids, polyaspartic acids and the corresponding esters and amides, polysaccharides e.g. polydextranes, modified polysaccharides e.g. polycarboxydextranes, carboxymethylcelluloses, hydroxyalkylcelluloses, alginates, pectines and combinations and copolymers thereof. Said polymers may optionally contain charged moieties, e.g. anionic, cationic or zwitterionic groups.

Said hydrophobic segments may be selected from the group consisting of polyolefines, e.g. polyethylene, polypropylene, polybutylene, polyisobutylene, polybutadiene, polyisoprene, polystyrene, cross-linked polystyrenes, poly-p-xylylenes, polyvinylchloride, polyvinylidenechloride, polytetrafluorethylene, polyacrylates, polymethacrylates, e.g. poly(meth)alkylacrlyates, polyethers, e.g. polyoxymethylene, polyphenyleneoxide, polyetheretherketone, polyesters, e.g. polyethyleneterephthalate, polybutyleneterephthalate, polylactic acid, polyglycolic acid, polyvinyl acetate, polyamides, e.g. polyamide-6, polyamide-6.6, polyamide-6.10, polyamide-6.12, polyamide-11, polyamide-12, hydrophobic biopolymers, including natural rubbers, polyurethanes, polyureas, polyphosphazenes and polydialkylsiloxanes, e.g. polydimethylsiloxanes, polynorbornenes and polynorbornadienes.

Suitable amphiphilic block co-polymers may include, but are not limited to, polystyrene-block-polyethylene oxide, polystyrene-block-poly-L-lactide, polyglycolide-block-polyethylene oxide, polylactide-glycolide-block-polyethylene oxide, polystyrene-block-polymethacrylic acid, polystyrene-block-polyacrylic acid, poly(butadiene)-block-poly(ethylene oxide) poly(isoprene)-block-poly(2-vinpyridine), poly(isoprene)-block-poly(ethylene oxide), poly(methyl methacrylate)-block-poly(2-hydroxyethyl methacrylate), polystyrene-block-poly(2-vinylpyridine), polystyrene-block-poly(4-vinpyridine), poly(methacrylic acid)-block-poly(butyl acrylate), poly(ethylene glycol) methyl ether-block-poly(D,L lactide), poly(ethylene glycol)-block-poly (D,L lactide), poly(ethylene glycol) methyl ether-block-poly (D,L lactide)-block-decane, poly(ethylene glycol)-block-poly(D,L lactide)-block-decane, poly(ethylene glycol)-block-polylactide methyl ether, poly(L-lactide)-block-poly (ethylene glycol)methyl ether polylactide, poly(ethylene glycol) methyl ether-block-poly(lactide-co-glycolide), poly (ethylene glycol)-block-poly(lactide-co-glycolide), poly (ethylene glycol)-block-poly(ε-caprolactone) methyl ether, poly(ethylene glycol)-block-poly(ε-caprolactone), polyethylene-block-poly(ethylene glycol), polyethylene-block-poly (ethylene glycol) methyl ether, poly(styrene)-block-poly (ethylene glycol), poly(styrene)-block-poly(ethylene glycol) methyl ether, poly(ethylene glycol)-block-polypropylene glycol (Poloxamer), polyoxyethylen(20)-sorbitan-monooleate (TWEEN 80).

Examples of Y-shaped block copolymers, optionally comprised of two optionally different hydrophilic and one hydrophobic polymer chain or vice versa, include, but are not limited to $(PI)_2$-b-PEO, PI-b-$(PEO)_2$, $PS_2$-b-PEO, (polystyrene)$_2$-block-poly(ethylene oxide), (polystyrene)$_2$-block-poly(L-lactide), (polystyrene)$_2$-block-poly(methyl methacrylate), (polystyrene)$_2$-block-poly(tert-butyl methacrylate), polystyrene-block-[poly(tert-butyl acrylate)]$_2$, polystyrene-block-[poly(acrylic acid)]$_2$, polystyrene-block-[poly(ethylene oxide)]$_2$.

Examples of branched block copolymers may include, but are not limited to poly(ethylene oxide)-block-polylactide, 4-arm poly(ethylene oxide), poly(ethylene oxide)-block-polycaprolactone, 4-arm poly(ethylene oxide).

Examples of dendritic amphiphilic block copolymers are given in the literature, e.g. Virgil Percec, et al. Self-Assembly of Janus Dendrimers into Uniform Dendrimersomes and Other Complex Architectures, Science 328, 1009 (2010).

The micellar encapsulated nanoparticles thus obtained can be used directly, but preferably are optionally further processed by cross-linking said micelle forming polymers using processes described in the literature.

Cross-linking includes, but is not limited to radical, anionic, cationic and oxidative induced cross-linking, radiation induced cross-linking, e.g. by light of different wavelengths like x-ray, UV, visible or infrared, thermal cross-linking or chemical cross-linking, e.g. ring opening of multiple epoxide moieties with nucleophiles, e.g. amines. Further, in particular the cross-linking can be performed by amino,—thiol—and/or hydroxy groups. in particular polyamines providing more than one amino group, or vulcanization processes with sulfur containing compounds, e.g. disulfur dichloride and the like. In particular, if the micelle forming polymers contain unsaturated bonds, i.e carbon-carbon double bonds, or carbon-carbon triple bonds cross-linking can be accomplished via various processes as described e.g. in patent application WO 2010/100108 A1.

Cross-linking of micelles comprised of amphiphilic unimers containing unsaturated carbon-carbon bonds, with dithiols in an aqueous composition has been described (Barbara Rupp; Thomas Bauer; Christian Slugovc "Thiol-ene reaction as tool for cross-linking of polynorbornene micelles in the nanoscale", Proceedings of SPIE, Vol. 7393 73930Y-1-9).

However, said micelles described in the literature did not contain nanoparticles. Moreover the cross-linking of said micelles has been performed in aqueous solution and has not been described in non-aqueous solution. Surprisingly, cross-linking of said unsaturated unimers of a micelle encapsulating at least one nanoparticle can be accomplished in non-aqueous solution by compounds containing at least two thiol moieties. Thus, the preparation of micellar encapsulated nanoparticles and cross-linking of the micelle by using thiol-ene click chemistry in non-aqueous solutions is novel. A thiol, sulfanyl or mercaptan is characterized by a —SH moiety. Within the scope of the invention the terms thiol, sulfanyl or mercaptan are interchangeably used. A thiolated compound, thiolated biomolecule etc. refers to a compound bearing at least one thiol moiety. The reaction of a thiol with an unsaturated carbon-carbon bond is well known as thiol-ene chlick chemistry [e.g. Charles E. Hoyle, Christopher N. Bowman "Thiol-Ene Click Chemistry"; Angew. Chem. Int. Ed. 2010, 49, 1540-1573; Charles E. Hoyle, Andrew B. Lowe, Christopher N. Bowman "Thiol-click chemistry: a multifaceted toolbox for small molecule and polymer synthesis"; Chem. Soc. Rev., 2010, 39, 1355-1387; Alessandro Dondoni "The Emergence of Thiol-Ene Coupling as a Click Process for Materials and Bioorganic Chemistry"; Angew. Chem. Int. Ed. 2008, 47, 8995-8997]. The reaction of a thiol with a carbon carbon multiple bond, e.g. a carbon double bond may occur according to different chemical mechanisms, e.g. via radical or ionic intermediates. It is understood that all kinds of reactions of thiols with carbon carbon multiple bonds, e.g. carbon double bonds regardless of their underlying mechanisms are within the scope of the invention. In addition, the cross-linking of micelles can be performed by disulfide bonds established by at least two thiol moieties which can be comprised by the micelles or by an added reactant.

Within the scope of the present invention, thiol-ene click chemistry is optionally used for cross-linking and/or functionalization with a biomolecule of the micellar encapsulated nanoparticles.

Cross-linking is accomplished with compounds containing at least two thiol moieties. Functionalization with a biomolecule is either accomplished by a biomolecule, which originally contains at least one accessible thiol moiety, e.g. peptides, which contain at least one accessible cysteine residue, or by linking a biomolecule to a molecule representing at least one thiol moiety suitable for the subsequent thiol-ene click reaction or building disulfide bonds.

Alternatively, said unsaturated unimers of a micelle encapsulating at least one nanoparticle can be functionalized via heterobifunctional linkers, which contain at least one thiol moiety participating in the thiol-ene click reaction an another functional group suitable for orthogonal conjugation to a biomolecule. Said suitable functional groups for bioconjugation are described in e.g. Greg T. Hermanson "Bioconjugate Techniques (Third Edition)" ISBN: 978-0-12-382239-0.

The cross-linking and functionalization with a biomolecule can be performed sequentially, either performing the cross-linking prior to the biofunctionalization, or vice versa. In an embodiment of the present invention using said sequential process, the solvents used for the cross-linking and for the biofunctionalization may be different. Said solvents may be aqueous or non-aqueous solvents, with the proviso that at least one of the solvents used in said sequential process is non-aqueous. Optionally, said solvents may be mixtures.

Optionally, cross-linking and functionalization with a biomolecule can be accomplished simultaneously, either by mixing at least one compound bearing at least two thiol moieties and at least one thiolated biomolecule prior to the cross-linking step, or by attaching a biomolecule to a thiol compound with the proviso that the resulting conjugate contains at least two thiol moieties suitable for cross-linking. Notably, the process of micellar encapsulation and subsequent thiol-ene chemistry cross-linking and/or thiol-ene chemistry functionalization with a biomolecule can be performed under completely anhydrous conditions, if desired.

Generally, functionalization of said micelle(s), generated according to the present invention with a biomolecule can be accomplished by methods well known in the art, relying on covalent and non-covalent binding mechanisms. Exemplarily, covalent linkers of a biomolecule to micelles may include, but are not restricted to carbon-carbon, carbon-nitrogen, carbon-sulfur, carbon-oxygen, carbon-phosphorus, carbon-selenium, nitrogen-nitrogen, nitrogen-phosphorus, sulfur-oxygen, sulfur-nitrogen, sulfur-sulfur, sulfur-phosphorus bonds, e.g. carboxamides, carbamates, ureas, thiocarbamates, dithiocarbamates, ethers, thioethers, carboxylic esters, thiocarboxylates, carbonate esters, amines, imines, hydrazines, hydrazones, hydrazides, phosphate esters, phosphonate esters, phosphoamidates and the like, as comprehensively described in Greg T. Hermanson "Bioconjugate Techniques (Third Edition)" ISBN: 978-0-12-382239-0. Optionally, said covalent bonds may generated by enzymatic activity, e.g. HaloTag® SnapTag® and the like. Optionally, said covalent bonds may be generated by "click chemistry", other than the above mentioned thiol-ene-click-chemistry, like Huisgen-Sharpless dipolar addition of azides to carbon carbon multiple bonds, Staudinger ligation, inverse electron demand Diels-Alder cycloadditions and the variations thereof (see: Ellen M. Sletten and Carolyn R. Bertozzi: Bioorthogonal Chemistry: Fishing for Selectivity in a Sea of Functionality, Angew. Chem. Int. Ed. 2009, 48, 6974-6998; Michael D. Best: Click Chemistry and Bioorthogonal Reactions: Unprecedented Selectivity in the Labeling of Biological Molecules, Biochemistry 2009, 48, 6571-6584; W. Russ Algar, Duane E. Prasuhn, Michael H. Stewart, Travis L. Jennings, Juan B. Blanco-Canosa, Philip E. Dawson, Igor L. Medintz: The Controlled Display of Biomolecules on Nanoparticles: A Challenge Suited to Bioorthogonal Chemistry; Bioconjugate Chem. 2011, 22, 825-858).

Exemplarily, non-covalent binding mechanisms, may include hydrophobic interactions, van-der-Waals interactions, electrostatic interactions, optionally leveraging on cooperative effects or lectin interactions, in particular, interactions, which rely on the binding of biotin to glycoproteins like avidin, streptavidin, neutravidin and the like.

As a result, colloidal compositions of perfectly dispersed nanoparticles in micelles in a non-aqueous environment are obtained. The generation of micelles, e.g. in methanol was evident from the fact that said nanoparticles without micelle forming additives were completely insoluble in methanol. Micelle formation was further proven via DLS measurements (see FIG. 1). FIG. 1 shows the DLS-Data of CdSeTe/CdS (core/shell) nanoparticles after the encapsulation in polymeric micelles in methanol and after the transfer into water. Said nanoparticles still display virtually identical properties like the native nanoparticles, e.g. fluorescent semiconductor nanoparticles still display virtually identical optical properties like the native nanoparticles (see e.g. FIG. 2 (absorption spectrum (left) and emission spectrum (right)) and FIG. 3 (absorption spectrum (left) and emission spectrum (right) of native CdSe/CdS/ZnS (core/shell/shell) nanoparticles in chloroform and of micellar encapsulated CdSe/CdS/ZnS (core/shell/shell) nanoparticles in methanol).

Figure 57:
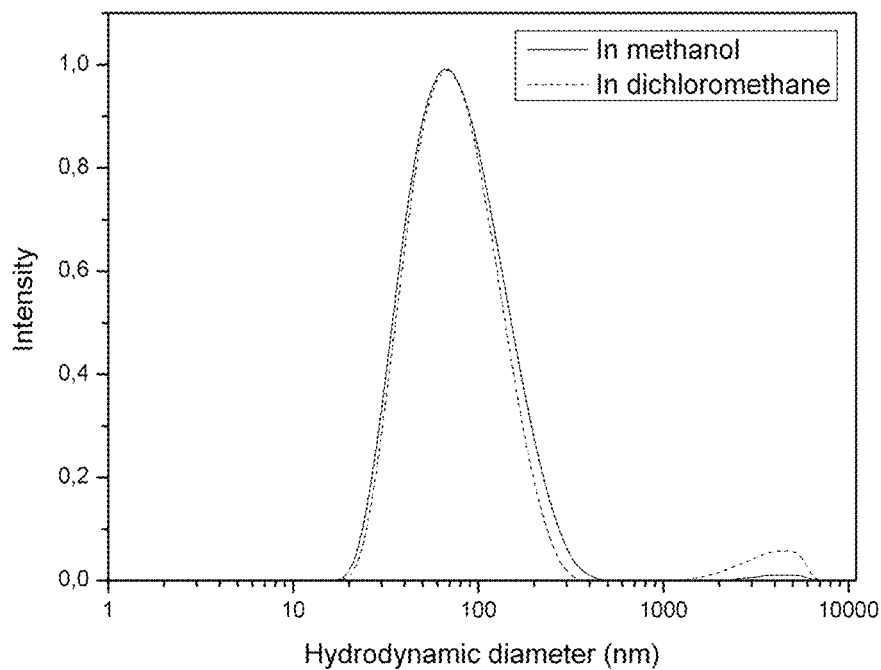
FIG. 57 shows the dynamic light scattering of cross-linked micelle encapsulated CdSe/CdS rod-shaped nanoparticles in methanol and dichloromethane.
Figure 58:
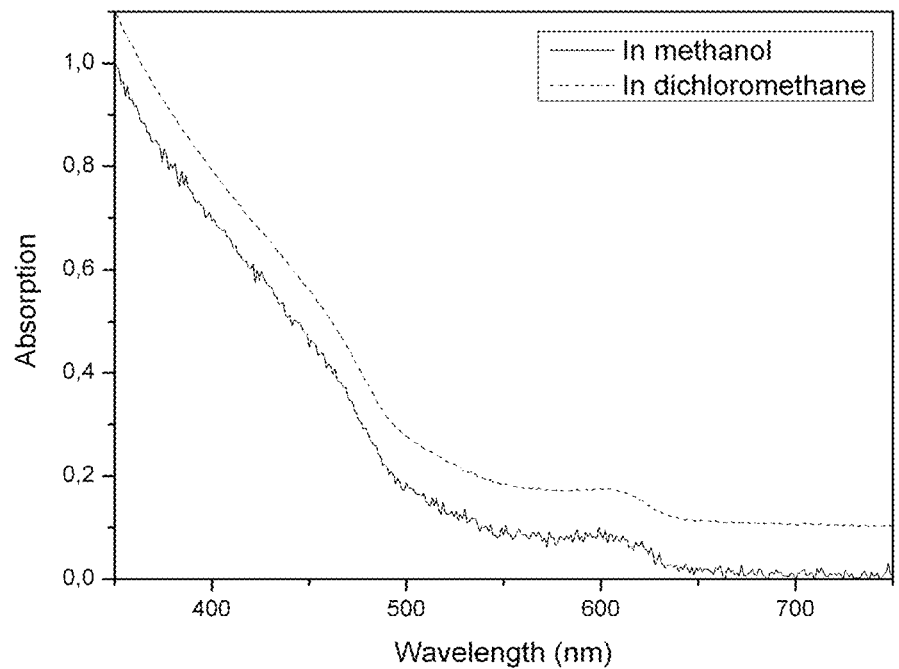
FIG. 58 shows the absorption spectra of cross-linked micelle encapsulated CdSe/CdS rod-shaped nanoparticles in methanol (solid line) and of cross-linked micelle encapsulated CdSe/CdS rod-shaped nanoparticles in dichloromethane (dashed line).
Figure 59:
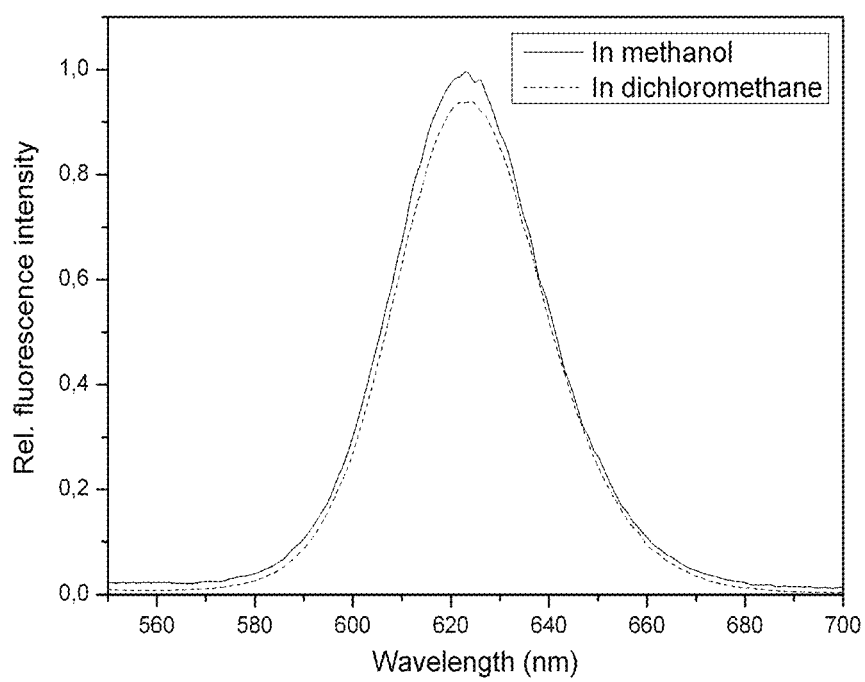
FIG. 59 shows the fluorescence spectra of cross-linked micelle encapsulated CdSe/CdS rod-shaped nanoparticles in methanol (solid line) and of cross-linked micelle encapsulated CdSe/CdS rod-shaped nanoparticles in dichloromethane (dashed line).

Successful cross-linking via thiol-ene click chemistry was evident from the fact that the micelles obtained after cross-linking with 1,9-dithiononane (Example 33) were completely stable in dichloromethane, without molecular solvation of the constituting unimers as proven by DLS and spectroscopy (FIGS. 57 to 59)

Suitable non-aqueous solvents may include, but are not restricted to unbranched, branched or cyclic alkanes, optionally bearing one or more halogen atoms, like pentane, hexane, iso-hexanes, cyclopentane, cyclohexane, dichloromethane, chloroform, 1,1-dichloroethane, or 1,2-dichloroethane; halogenated alkenes, like 1,1-dichloroethene or all isomers of 1,2-dichloroethene; optionally alkylated aromatic or heteroaromatic solvents, optionally bearing one or more halogen atoms, e.g., benzene, toluene, ethyl benzene, xylenes, chloro benzene, pyridine, collidines or lutidines; unbranched, branched or cyclic ethers, like diethyl ether, diisopropyl ether, methyl t-butyl ether, tetrahydrofuran or 1,4-dioxane; carbonyl compounds, in particular ketones like acetone, methyl ethyl ketone, cylopentanone or cyclohexanone; carboxylic acid esters, e.g. ethyl acetate and the like, unbranched or branched $C_1$-$C_5$ alkanols, like methanol, ethanol, n-propanol, i-propanol, or all isomers of butanol and pentanol; polyols, like ethylene glycol, 1,2-propanediol, 1,3-propanediol, glycerol, 1,2-butanediol, 1,3-butanediol, 1,4-butanediol, 1,2,4-butanetriol, diethylene glycol (DEG); ethers of polyols, e.g. 2-methoxyethanol, bis-(2-methoxyethyl) ether (diglyme); esters of polyols, e.g. diacetoxyethane; carboxylic acids, like formic acid, acetic acid, propanoic acid, lactic acid; dialkyl sulfoxides, e.g. dimethyl sulfoxide (DMSO); carboxylic acid amides, e.g. formamide, acetamide, N-methyl formamide, N-methyl acetamide, N,N-dimethyl formamide (DMF), N,N-dimethyl acetamide (DMA), or N-methylpyrrolidone (NMP); phosphoric acid amides e.g. hexamethyl phosphoric acid triamide (HMPA); urea based solvents like 1,3-dimethyl-3,4,5,6-tetrahydro-2 (1H)-pyrimidinone (DMPU), 1,3-dimethyl-2-imidazolidinone (DMI), or tetramethyl urea (TEMUR); lower alkylnitriles like acetonitrile, propionitrile or butyronitrile; ionic liquids, e.g. ammonium-based ionic liquids; imidazolium based ionic liquids like 1-allyl-3-methylimidazolium, 1-benzyl-3-methylimidazolium, 1-butyl-2,3-dimethylimidazolium, 1-butyl-3-methylimidazolium, 1-decyl-3-methylimidazolium, 1,3-didecyl-2-methylimidazolium, 1,3-dimethylimidazolium, 1,2-dimethyl-3-propylimidazolium, 1-dodecyl-3-methylimidazolium, 1-ethyl-2,3-dimethylimidazolium, 1-ethyl-3-methylimidazolium, 1-hexadecyl-3-methylimidazolium, 1-hexyl-3-methylimidazolium, 1-(2-hydroxyethyl)-3-methylimidazolium, 1-methyl-3-octadecylimidazolium, 1-methyl-3-octylimidazolium, 1-methyl-3-propylimidazolium salts, preferably with complex anions like e.g. tetrafluoroborate; piperidinium-based ionic liquids, like 1-butyl-1-methylpiperidinium, 1-methyl-1-propylpiperidinium; pyridinium-based ionic liquids, 1-alkyl-2-methylpyridinium, 1-alkyl-3-methylpyridinium, 1-alkyl-4-methylpyridinium, 1-butylpyridinium, 1-propylpyridinium, 1-ethylpyridinium, 1-hexylpyridinium salts, preferably with complex anions like e.g. tetrafluoroborate; pyrrolidinium-based ionic liquids, e.g. 1-butyl-1-methylpyrrolidinium, 1-ethyl-1-methylpyrrolidinium, 1-methyl-1-propylpyrrolidinium salts, preferably with complex anions, and combinations or combinations of mixtures thereof.

In particular, the non-aqueous solution may comprise at least partially a water miscible non-aqueous solvent and/or wherein the non-aqueous solution comprises a non-aqueous solvent, which does not form azeotropic phases with water.

Furthermore, the water miscible non-aqueous solvent may have a higher boiling point than water.

Second Aspect of the Present Invention

In a second aspect of the invention, nanoparticles may be enclosed in micelles in an aqueous preparation and the micelle surface is subsequently cross-linked by thiol-ene click chemistry as described above, or known chemical methods, e.g. condensation, radical induced polymerization and the like, as comprehensively described in patent applications WO 2012/001012 A2 and WO 2010/100108 A1. Said aqueous preparation of nanoparticles enclosed in preferably cross-linked micelles can be successively transferred in a non-aqueous solution, provided that the non-aqueous solvent is at least partially miscible with the aqueous solution, herefrom the water is removed.

In other words, a method is provided for providing a composition comprising at least one micelle in non-aqueous solution, wherein the micelle encapsulates one or more nanoparticle(s), wherein in a first step the micelle encapsulating the one or more nanoparticle(s) is formed in a first solution being different from the non-aqueous solution and wherein in a second step the first solution is replaced by the non-aqueous solution.

Then the aqueous preparation of said nanoparticles in cross-linked micelles may be mixed with at least one water miscible non-aqueous solvent with a higher boiling point than the aqueous preparation of said nanoparticles.

"Water miscible" within the scope of the invention means that a solvent forms a homogenous phase with water, containing at least 1% per volume of water.

Preferably said non-aqueous solvents may not form azeotropic phases with water.

The water may be subsequently removed, preferably by distillation at or below atmospheric pressure.

Suitable non-aqueous solvents may include, but are not restricted to dialkyl sulfoxides, e.g. dimethyl sulfoxide (DMSO); carboxylic acid amides, e.g. formamide, acetamide, N-methyl formamide, N-methyl acetamide, N,N-dimethyl formamide (DMF), N,N-dimethyl acetamide (DMA), or N-methylpyrrolidone (NMP); phosphoric acid amides e.g. hexamethyl phosphoric acid triamide (HMPA); urea based solvents like 1,3-dimethyl-3,4,5,6-tetrahydro-2 (1H)-pyrimidinone (DMPU), 1,3-dimethyl-2-imidazolidinone (DMI), or tetramethyl urea (TEMUR); 1,4-dioxane; higher alkanols, e.g. 1-butanol; polyols, like ethylene glycol, 1,2-propanediol, 1,3-propanediol, glycerol, 1,2-butanediol, 1,3-butanediol, 1,4-butanediol, 1,2,4-butanetriol, diethylene glycol (DEG); ethers of polyols, e.g. 2-methoxyethanol, bis-(2-methoxyethyl) ether (diglyme); esters of polyols, e.g. diacetoxyethane; carboxylic acids, like formic acid, acetic acid, propanoic acid, lactic acid; primary, secondary and tertiary amines, diamines or triamines bearing branched, unbranched or cyclic alky groups on the nitrogen atoms and being liquids at ambient temperature; cyclic or bicyclic amines, optionally bearing further heteroatoms, selected from N, O, or S in the ring, like piperidine, N-methyl piperidine, morpholine, N-methyl morpholine; annelated amidine bases, like 1,5-diazabicyclo(4.3.0)non-5-ene (DBN) or 1,8-diazabicyclo[5.4.0]undec-7-ene (DBU); optionally alkylated pyridines, e.g. pyridine, all isomers of picoline, lutidine and collidine; C1-2 nitro alkanes; ionic liquids, e.g. ammonium-based ionic liquids; imidazolium based ionic liquids like 1-allyl-3-methylimidazolium, 1-benzyl-3-methylimidazolium, 1-butyl-2,3-dimethylimidazolium, 1-butyl-3-methylimidazolium, 1-decyl-3-methylimidazolium, 1,3-didecyl-2-methylimidazolium, 1,3-dimethylimidazolium, 1,2-dimethyl-3-propylimidazolium, 1-dodecyl-3-methylimidazolium, 1-ethyl-2,3-dimethylimidazolium, 1-ethyl-3-methylimidazolium, 1-hexadecyl-3-methylimidazolium, 1-hexyl-3-methylimidazolium, 1-(2-hydroxyethyl)-3-methylimidazolium, 1-methyl-3-octadecylimidazolium, 1-methyl-3-octylimidazolium, 1-methyl-3-propylimidazolium salts, preferably with complex anions like e.g. tetrafluoroborate; piperidinium-based ionic liquids, like 1-butyl-1-methylpiperidinium, 1-methyl-1-propylpiperidinium; pyridinium-based ionic liquids, 1-alkyl-2-methylpyridinium, 1-alkyl-3-methylpyridinium, 1-alkyl-4-methylpyridinium, 1-butylpyridinium, 1-propylpyridinium, 1-ethylpyridinium, 1-hexylpyridinium salts, preferably with complex anions like e.g. tetrafluoroborate; pyrrolidinium-based ionic liquids, e.g. 1-butyl-1-methylpyrrolidinium, 1-ethyl-1-methylpyrrolidinium, 1-methyl-1-propylpyrrolidinium salts, preferably with complex anions, which in combination with the cation renders the ionic liquid water miscible, like e.g. tetrafluoroborate, or mixtures of said solvents.

Some of the mentioned solvents may exist as isomers, geometrical isomers, stereoisomers, e.g. diastereomers or enantiomers, meso compounds or racemates. It should be understood that all isomers of said non-aqueous solvents are in the scope of the invention.

Some of the above mentioned solvents may be toxic to cell organelles, living cells, living tissues, organs or organisms. In some cases, e.g. antimicrobial activity may be a desirable feature of a composition of micelle encapsulated nanoparticles.

However, in general, said compositions of micelle encapsulated nanoparticles in solvents with minimal or no toxic side effects for the desired application are preferred.

Third Aspect of the Present Invention

In a third aspect of the invention, residual water may be removed from the micelle encapsulated nanoparticle preparation in non-aqueous solutions solely or supportingly by chemical or physical processes (see e.g. the second aspect of the present invention above), well known in the art. These processes include, but are not limited to, azeotropic removal of water, e.g. using solvents like toluene; diffusion or permeation across porous or non-porous membranes, including dialysis and pervaporation; or chemical drying using water-absorbing materials, including but not limited to, inorganic salts, like $Na_2SO_4$, $MgSO_4$, or $CaCl_2$, or minerals like e.g. bentonite; or polymers, in particular superabsorbent polymers (SAPs), e.g. polyacrylate- or cellulose based polymers and the like.

Fourth Aspect of the Present Invention

In a fourth aspect of the invention, a non-aqueous preparation of nanoparticles enclosed in preferably cross-linked micelles may be prepared from said aqueous preparation of nanoparticles enclosed in preferably cross-linked micelles by evaporating said aqueous preparation to dryness and dissolution of the residue in a suitable solvent, including the solvents mentioned above.

In general, all above disclosed compositions may be used for a biological event or biological application.

The term biological event or biological application has to be understood in the broadest sense.

In particular, the term biological event inter alia also covers the wanted or unwanted transfection of cells or the wanted or unwanted introduction of micelles of the composition into cells. Also, the conjugation to cells, the labeling of cells, cell compartments or subcellular organelles, the targeted or non-targeted transfer of biomolecules into the cell, cell compartments or subcellular organelles, the triggered or non-triggered release of the transferred biomolecules and the detection of a response shall be covered.

The term biological application also covers the use of the composition or parts of the composition for marking of biological liquids, organic components and structures, cells or the like. Said biological applications include, but are not limited to, the analytic or diagnostic detection of biomolecules, biological targets or event factors, the detection of target molecules form analytes by e.g. nucleic acid NP compositions like e.g. single stranded DNA-NP conjugates, single stranded RNA-NP conjugates, single stranded siRNA-NP conjugates, single stranded LNA-NP conjugates, double-stranded or multi-stranded variations thereof and combined products to be used in nucleic acid assays, like e.g. polymerase chain reaction (PCR), quantitative PCR, reverse transcriptase PCR, quantitative reverse transcriptase PCR, digital PCR or Helicase-dependent DNA amplification (HAD), isothermal HAD and the like, the detection of target molecules form analytes by e.g. aminoacid NP compositions like e.g. protein-NP conjugates, peptide-NP conjugates, antibody-NP conjugates, antibodylike-NP conjugates, aptamer-NP conjugates, by molecular detection methods like e.g. Western Blot, ELISA, DOT-Blot, Slot-Blot, Northern Blot, Southern Blot techniques and variations thereof. An example of blot variation is the NP composition optimized fast version, which only requires the incubation of immobilized target DNA with NP DNA molecular probes generated e.g. as described in example 10 (DNA Conjugation FIG. 4), and the analysis or detection of analytes in competition assays (FIG. 5).

EXAMPLES

Example 1

General Procedure for the Preparation of Micelle Encapsulated Nanoparticles in Methanol In the typical procedure, 5 nmol of nanoparticles in chloroform are mixed with 2.5 µmol of the diblock copolymer poly(isoprene-block-ethylene oxide) (PI-b-PEO; $M_N$=13700 g/mol) and diluted to a total volume of 500 µL with chloroform. Subsequently the homogeneous nanoparticle/polymer solution is quickly injected into a stirred solution of 5000 µL methanol. The resulting solution is stirred for a minute. The encapsulation of the nanoparticles within the micellular core region can be concluded from the fact, that all used nanoparticles bear hydrophobic surface ligands, which makes the native particles insoluble in methanol. However, after the micelle encapsulation process a homogenous solution of the nanoparticles is obtained, showing comparative characteristics as the native solutions.

Example 2

Figure 2:
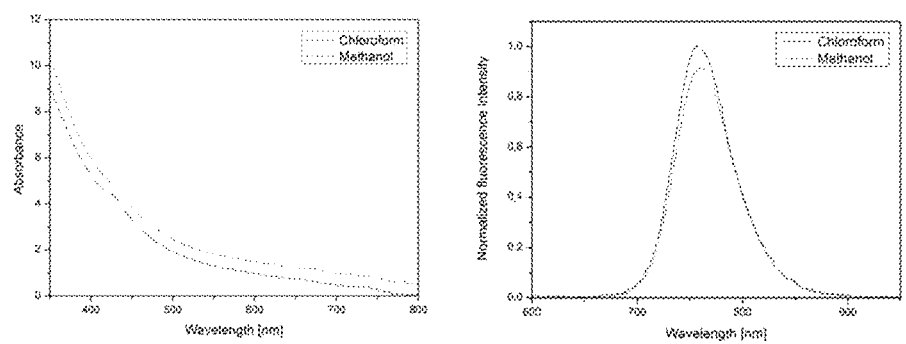
FIG. 2 shows the absorption spectrum (left) and emission spectrum (right) of native CdSeTe/CdS nanoparticles in chloroform and of micellar encpasulated CdSeTe/CdS nanoparticles in methanol.
Figure 3:
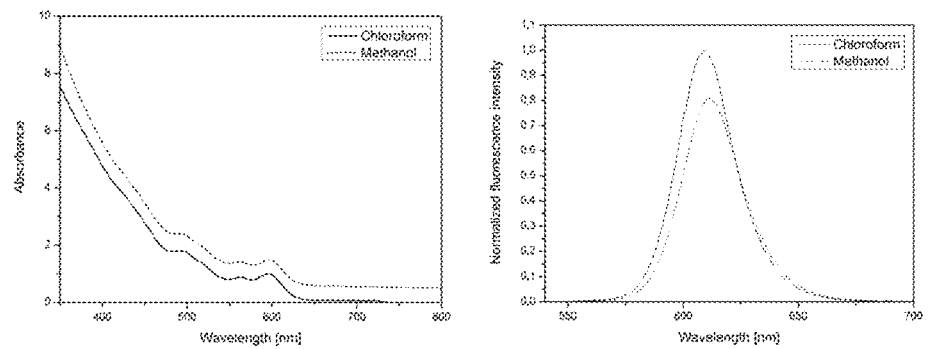
FIG. 3 shows the absorption spectrum (left) and emission spectrum (right) of native CdSe/CdS/ZnS nanoparticles in chloroform and of micellar encpasulated CdSe/CdS/ZnS nanoparticles in methanol.

Non-Aqueous Composition of Micelle Encapsulated Fluorescent Trioctylamine-Coated CdSeTe/CdS Nanoparticles in Methanol 2 nmol of trioctylamine-coated CdSeTe/CdS core/shell nanoparticles and 2.4 µmol (1200 fold excess) of poly (isoprene-b-ethylene oxide) diblock copolymer (PI-b-PEO) with an average mol weight of 13700 g/mol and a PI/PEO weight ratio of 1:2 were dissolved in 200 µL of chloroform and then quickly injected into 2 mL of methanol. A clear, slightly colored solution was obtained, indicating that the starting material, which is completely insoluble in methanol, was successfully encapsulated in PI-b-PEO micelles. Accordingly, dynamic light scattering (DLS) indicated micelles with diameters of about 20 to 30 nm. (FIG. 1 and FIG. 2)

Example 3

Non-Aqueous Composition of Micelle Encapsulated Fluorescent Octadecylamine-Coated CdSeTe/CdS Nanoparticles 2 nmol of octadecylamine-coated CdSeTe/CdS core/shell nanoparticles were incubated with 1.2 µmol (600 fold excess) of diethylene triamine functionalized polyisoprene (PI-DETA; 3000 g/mol) in chloroform and then precipitated by the addition of ethanol. Subsequently, the PI-DETA-coated nanoparticles and 2.4 µmol (1200 fold excess) of the PI-b-PEO diblock copolymer (13700 g/mol) were dissolved in 200 µL of chloroform and then quickly injected into 2 mL of methanol. The clear, slightly colored solution thus obtained indicated the colloidal dissolution of the nanoparticles in polymer micelles. Micelle formation was confirmed by dynamic light scattering (DLS), indicating micelles with diameters of about 20 to 30 nm.

Example 4

Non-Aqueous Composition of Micelle Encapsulated Fluorescent TOP/TOPO-Coated CdSe/CdS/ZnS Particles Similar to Example 3, 5 nmol of TOP/TOPO-coated CdSe/CdS/ZnS core/shell/shell nanoparticles were pre-coated with 3.0 µmol (600 fold excess) of PI-DETA (3000 g/mol) and then precipitated by the addition of ethanol. Subsequently, the particles and 1.5 µmol (300 fold excess) of the PI-b-PEO diblock copolymer (13700 g/mol) were dissolved in 200 µL chloroform and then quickly injected into 2 mL methanol. The clear, slightly colored solution thus obtained indicated the colloidal dissolution of the nanoparticles in polymer micelles. Micelle formation was confirmed by dynamic light scattering (DLS), indicating micelles with diameters of about 20 to 30 nm. (Spectral properties FIG. 3)

Example 5

Transfer of Micellar Encapsulated Nanoparticles from Methanol to Water

In a subsequent step the micellar encapsulated nanoparticles are transferred from methanol to water.

FIG. 1 shows DLS-Data for micellar encapsulated nanoparticles in methanol (dashed line) and water (solid line).

First, most of the solvents were removed by rotary evaporation. The concentrated solution was injected into 10 mL of water, resulting in a clear, slightly colored solution. Minor methanol impurities were removed by several washing steps with water using centrifugal concentrators (Sartorius VivaSpin 20). The DLS data show slightly increased hydrodynamic diameters for micelles in water compared to micelles in methanol, due to swelling of the PEO block in water.

Example 6 a) Composition of Micelle Encapsulated Fluorescent Quantum Dots in Aqueous Solution An aqueous composition of fluorescent quantum dot-rods was prepared according to: Jan Niehaus, Sören Becker, Christian Schmidtke, Daniel Ness, Katja Werner, Horst Weller, "Water-soluble nanoparticles as an universal imaging tool", From Nanotech Conference & Expo 2012: An Interdisciplinary Integrative Forum on Nanotechnology, Microtechnology, Biotechnology and Cleantechnology, Santa Clara, Calif., United States, Jun. 18-21, 2012, 1, 413-416 (2012), starting from cadmium selenide/cadmium sulfide CANdots® quantum rods purchased from STREM Inc (CdSe/CdS elongated core/shell; CAS Number: 1306-24-7; MDL Number: MFCD00171259; 590 nm peak emission). Also, the methods as disclosed by WO 2012/001012 A2 and WO 2010/100108 A1 can be used and have been used for enabling this possible embodiment.

b) Non-Aqueous Composition of Micelle Encapsulated Fluorescent Quantum Dot-Rods in Rac-1,2-Propanediol 1 mL of a 5 µM aqueous micellar preparation of fluorescent quantum dot-rods, according to Example 6a were added to 1 mL of rac-1,2-propanediol (Sigma-Aldrich, 39, 803-9, Lot. 04430JJ-249) in a round bottom flask. Water was removed by rotary evaporation (70 hPa, 60° C. bath temperature) to a residual volume of 950 µL in the flask.

A sample of 50 µL of the preparation of fluorescent quantum dot-rods in rac-1,2-propanediol was diluted with distilled water to an overall volume of 3 mL. A clear solution was obtained without any precipitation, even after extended storage. From this solution an UV spectrum was recorded and the hydrodynamic diameter was estimated by dynamic light scattering (DLS). No differences compared to a corresponding dilution of the starting composition of Example 2 in water were detectable.

Example 7

Non-Aqueous Composition of Micelle Encapsulated Fluorescent Quantum Dot-Rods in Rac-1,3-Butanediol The experiment of Example 6 was repeated, replacing rac-1,2-propanediol with rac-1,3-butanediol. A dilution of this composition in water showed no differences compared to a dilution of the starting aqueous composition of Example 2.

Example 8

Conjugation of DNA to Micelle Encapsulated Fluorescent Quantum Dot-Rods in Rac-1,2-Propanediol An aliquot of 10 µL (50 pMol) of the composition obtained in Example 6 was mixed with 10.8 of a 92 µM stock solution of 5'-thiol terminated DNA (33mer) and adjusted to 50 µL by addition of rac-1,2-propanediol. The sample was heated to 50° C. for 2 h in a heating block. An aliquot of 5 µL was kept for analysis and the remaining volume was heated to 95° C. for 15 min. The samples were analyzed via gel electrophoresis on agarose. Aliquots of 2.5 µL of each sample were diluted with 22.5 µL distilled water and 5 µL gel loading buffer was added. Aliquots of 25 µL of this mixture were applied to a 0.8% agarose gel. After processing the electrophoresis by applying 90 V voltage for 1 h, samples were visualized by UV excitation of the quantum dot-rods. Successful conjugation was indicated by progression towards the anode due to the negative charge of the conjugated nanoparticles, whereas the unconjugated controls in 1,2-propanediol moved to the cathode. It was revealed that the conjugation of DNA is much more efficient in non-aqueous solution than in aqueous solution, most likely due to preservation of the stretched strand, whereas in aqueous solution a secondary structure will be taken to preserve hydrophobic bases from the environment. Heating to 95° C. was even more efficient than heating to 50° C. (FIG. 4).

For purification the nanoparticle-DNA conjugates were transferred into an ultrafiltration unit and diluted with 5 mL of 0.5×PBS. After centrifugation at 1200*g for 20 min the supernatant was discarded and centrifugation continued until a residual volume of 350 µL was achieved.

Example 9

Figure 4:
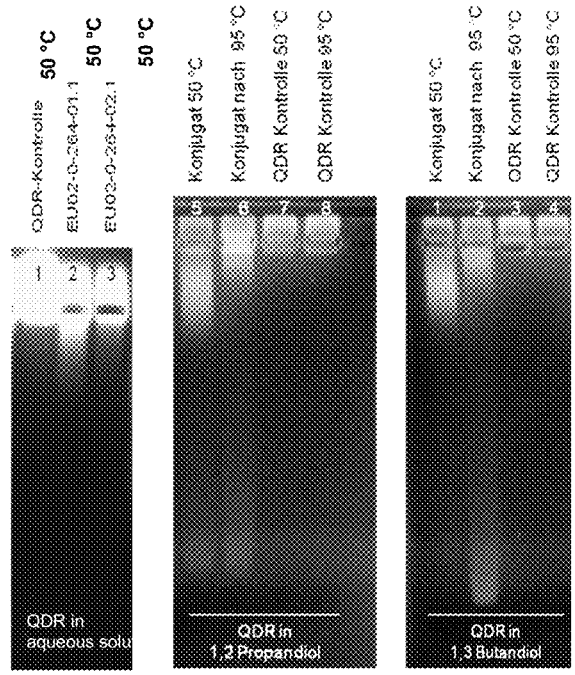
FIG. 4 shows agarose gel analysis of fluorescent quantum dot-rod nanoparticle-DNA conjugates. Conjugation was performed in aqueous solution (left), in 1,2-propanediol (middle) and 1,3-butanediol (right). Success of DNA binding is evident from increased movement from top (cathode) to the bottom (anode) of the gel.
Figure 5:
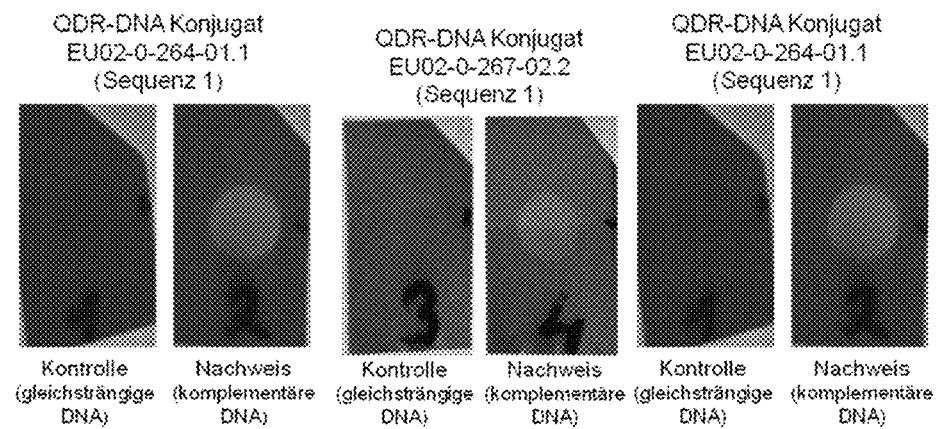
FIG. 5 shows spot tests from functional analysis of fluorescent quantum dot-rod nanoparticle-DNA conjugates. Conjugation was performed in aqueous solution (left), in 1,2-propanediol (middle) and 1,3-butanediol (right). Success of DNA binding is evident from accumulation of fluorescent quantum dot-rod nanoparticle-DNA conjugates on spotted complementary DNA.

Conjugation of DNA to Micelle Encapsulated Fluorescent Quantum Dot-Rods in Rac-1,3-Butanediol Performing the experiment of Example 8 with a composition of encapsulated fluorescent quantum dot-rods in rac-1,3-butanediol provided identical results (FIG. 4)

Example 10

Functional Proof of Fluorescent Quantum Dot-Rod—DNA Conjugates

Aliquots of 1 µL of a 45 µM NeutrAvidin stock solution (3.0 mg/mL) were spotted on stripes of nitrocellulose membrane and dried. Membranes were incubated with a solution of biotinylated complementary and biotinylated non-complementary DNA (cDNA). The membranes were incubated with fluorescent quantum dot-rod-DNA conjugates as described in example 8 and 9. An accumulation of the fluorescent quantum dot-rods-DNA conjugates was clearly detectable only on spots providing the complementary DNA but not on the control or on the blank membrane (FIG. 5).

Example 11 a) Composition of Micelle Encapsulated Fluorescent Quantum Dots in Aqueous Solution An aqueous composition of fluorescent quantum dots was prepared similarly to example 6a starting from cadmium selenide/zinc selenide/zinc sulfide CANdots® Series A org quantum dots commercially available from CAN GmbH, Germany (CdSe/ZnSe/ZnS core/shell/shell; 610 nm peak emission).

b) Conjugation of Biotin to Micelle Encapsulated Fluorescent Quantum Dots in 10% DMSO 29 mL of a 0.5 µM aqueous micellar preparation of fluorescent quantum dots, according to Example 6a were added to 3 mL DMSO Sigma-Aldrich, CAS 27,685-5) supplemented with 50 µM NHS-LC-LC-Biotin (N-Succinimidyl N-[6-(biotinylamino)caproyl]-6-aminocaproate, 6-(Biotinamidocaproylamido)caproic acid N-hydroxysuccinimide ester, AppliChem, Product: A7856,0050, MW 567.70 g/mol, CAS: 89889-52-1) in a 50 mL screw capped glass vial. The biotinylation reaction processed via NHS reaction on NH2-exposing micelle components upon incubation for 1.5 h at 40° C.

For purification the biotinylated nanoparticle micelles were transferred into two ultrafiltration units and concentrated by centrifugation in a Sorvall RC6+ high-speed centrifuge equipped with rotor 42, at 4.000 rpm at approx. 40° C. for 30 min. From each concentrator 5 mL sample was recovered and the pooled concentrate was diluted with 10 mL 1×PBS (1:10 dilution in ultrapure water from a 10×stock prepared from 100 g NaCl, 2.5 g KCl, 18 g $Na_2HPO_4.2H_2O$, 3 g $KH_2PO_4$ in 1 L of distilled water) supplemented with 0.0025 lithium-azide (CAS Number 19597-69-4). The final 10 mL sample was directly used for access NeutrAvidin binding a subsequent binding of biotinylated biomolecules to remaining free biotin binding sites on the thus NeutrAvidin functionalized micelle encapsulated fluorescent quantum dots.

Example 12

Figure 6:
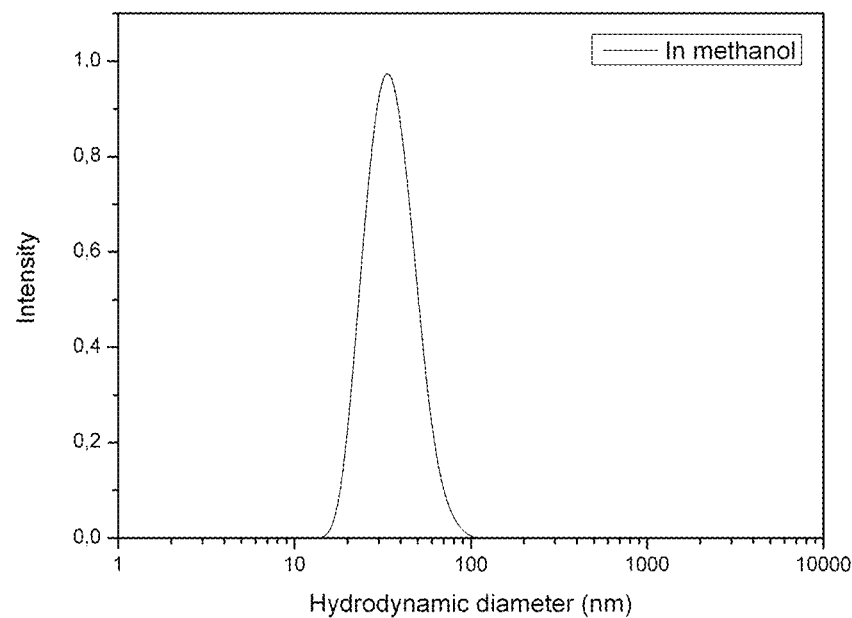
FIG. 6 shows the dynamic light scattering of micelle encapsulated trioctylamine coated CdSeTe/CdS nanoparticles in methanol.
Figure 7:
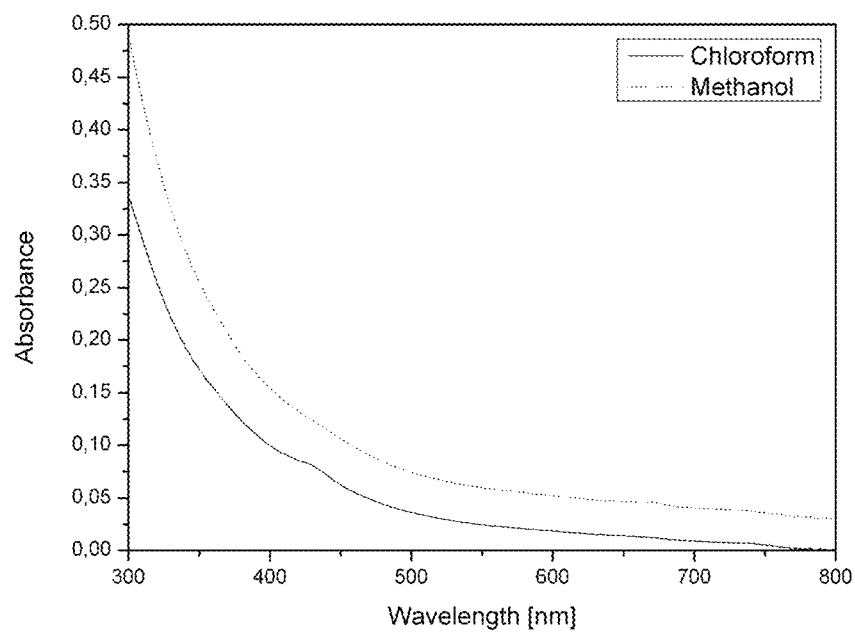
FIG. 7 shows the absorption spectra of TOA coated CdSeTe/CdS nanoparticles in chloroform (solid line) and the micelle encapsulated TOA coated CdSeTe/CdS nanoparticles in methanol (dotted line).
Figure 8:
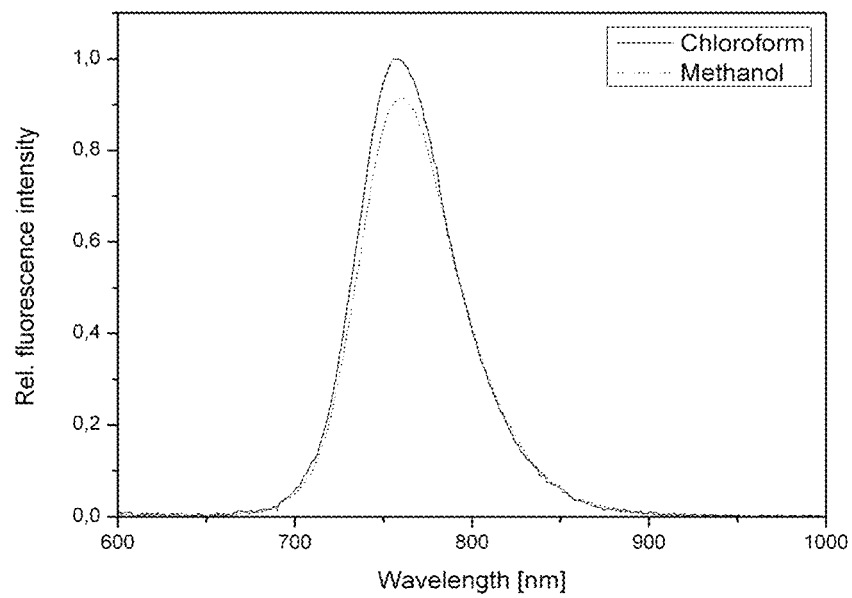
FIG. 8 shows the fluorescence spectra of TOA coated CdSeTe/CdS nanoparticles in chloroform (solid line) and the micelle encapsulated TOA coated CdSeTe/CdS nanoparticles in methanol (dotted line).

Composition of Micelle Encapsulated, Fluorescent, Trioctylamine Coated, 6 nm CdSeTe/CdS Nanoparticles in Methanol 2 nmol of trioctylamine-coated CdSeTe/CdS core/shell nanoparticles and 2.4 µmol (1200 fold excess) of poly (isoprene-b-ethylene oxide) diblock copolymer (PI-b-PEO) with an average mol weight of 13700 g/mol and a PI/PEO block weight ratio of 1:2 were dissolved in 200 µL of chloroform and then quickly injected into 2 mL of methanol. A clear, slightly colored solution was obtained, indicating that the starting material, which is completely insoluble in methanol, was successfully encapsulated in PI-b-PEO micelles. Micelle formation was confirmed by dynamic light scattering (DLS; FIG. 6). As can be seen from the spectroscopic measurements (FIG. 7 and FIG. 8), the absorption and emission properties of the nanoparticles are virtually maintained.

Example 13

Figure 9:
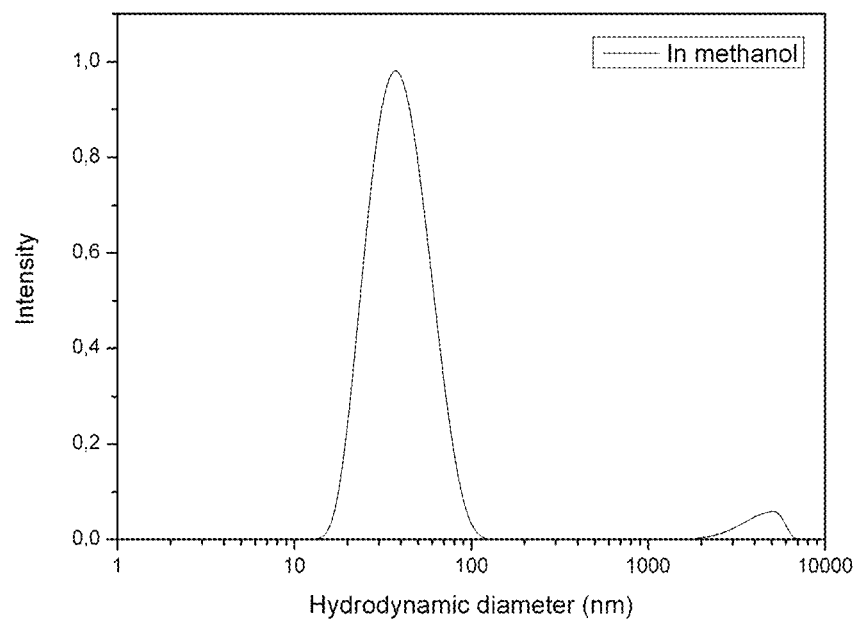
FIG. 9 shows the dynamic light scattering of micelle encapsulated PI-DETA coated CdSeTe/CdS nanoparticles in methanol
Figure 10:
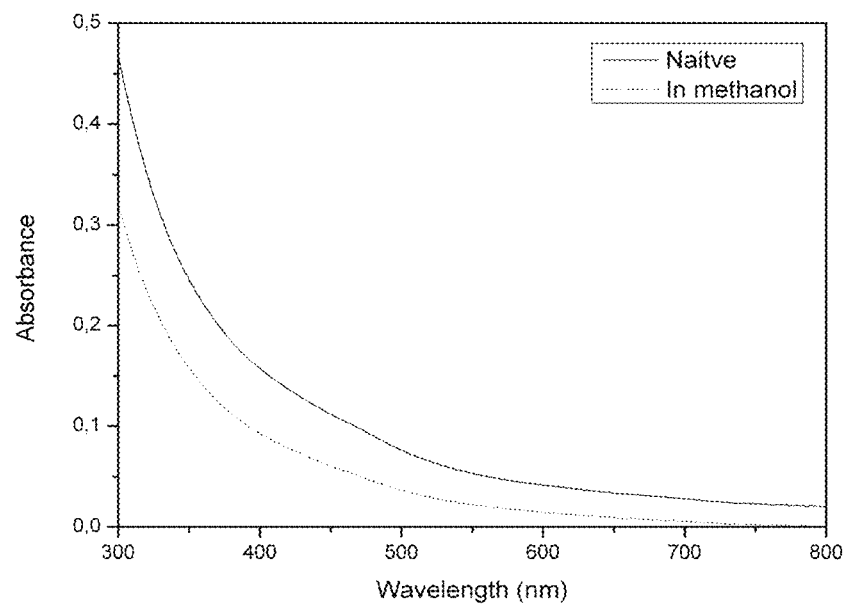
FIG. 10 shows the absorption spectra of PI-DETA coated CdSeTe/CdS nanoparticles in chloroform (solid line) and the micelle encapsulated PI-DETA coated CdSeTe/CdS nanoparticles in methanol (dotted line).
Figure 11:
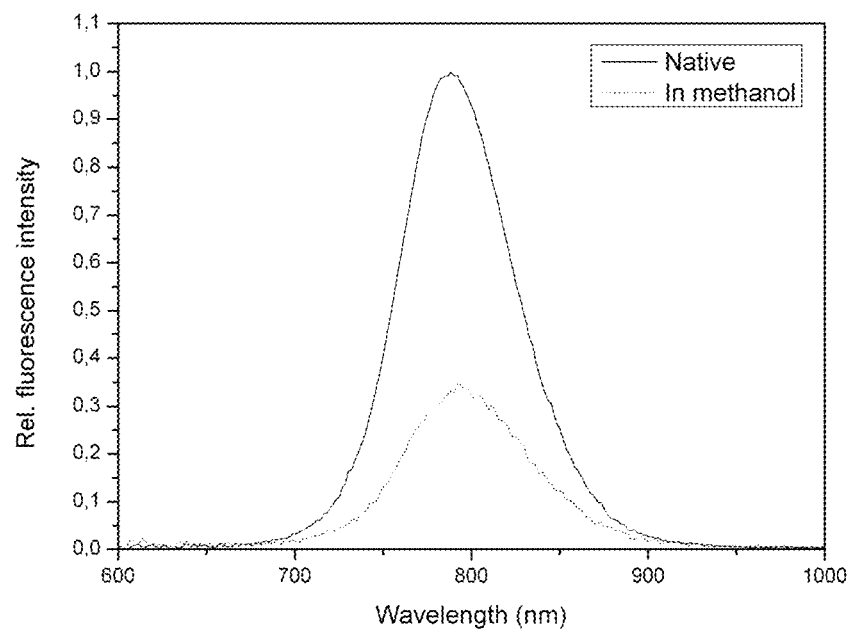
FIG. 11 shows the fluorescence spectra of PI-DETA coated CdSeTe/CdS nanoparticles in chloroform (solid line) and the micelle encapsulated PI-DETA coated CdSeTe/CdS nanoparticles in methanol (dotted line).

Composition of Micelle Encapsulated, Fluorescent, Octadecylamine Coated, 6 nm CdSeTe/CdS Nanoparticles in Methanol 2 nmol of octadecylamine-coated CdSeTe/CdS core/shell nanoparticles were incubated with 1.2 µmol (600 fold excess) of diethylene triamine functionalized polyisoprene (PI-DETA; 3000 g/mol) in chloroform and then precipitated by the addition of ethanol. Subsequently, the PI-DETA-coated nanoparticles and 2.4 µmol (1200 fold excess) of the PI-b-PEO diblock copolymer (13700 g/mol) were dissolved in 200 µL of chloroform and then quickly injected into 2 mL of methanol. The clear, slightly colored solution thus obtained indicated the colloidal dissolution of the nanoparticles in polymer micelles. Micelle formation was confirmed by dynamic light scattering (DLS; FIG. 9). The absorption and emission properties of the nanoparticles are displayed in FIG. 10 and FIG. 11.

Example 14

Figure 12:
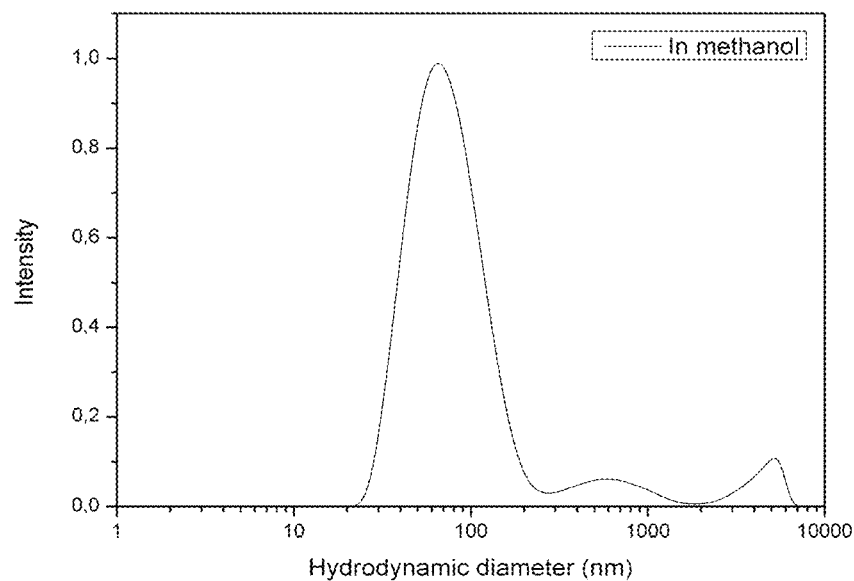
FIG. 12 shows the dynamic light scattering of micelle encapsulated PI-DETA coated CdSe/CdS/ZnS nanoparticles in methanol.
Figure 13:
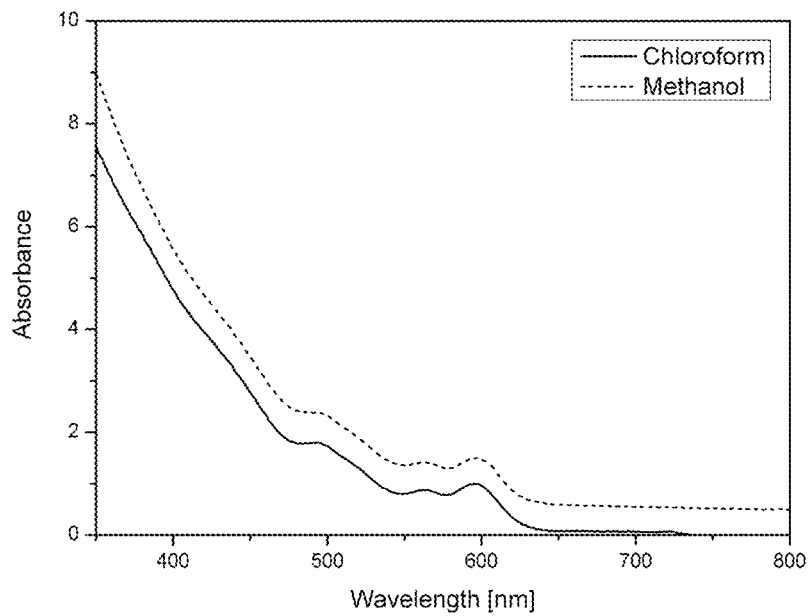
FIG. 13 shows the absorption spectra of PI-DETA coated CdSe/CdS/ZnS nanoparticles in chloroform (solid line) and the micelle encapsulated PI-DETA coated CdSe/CdS/ZnS nanoparticles in methanol (dotted line).
Figure 14:
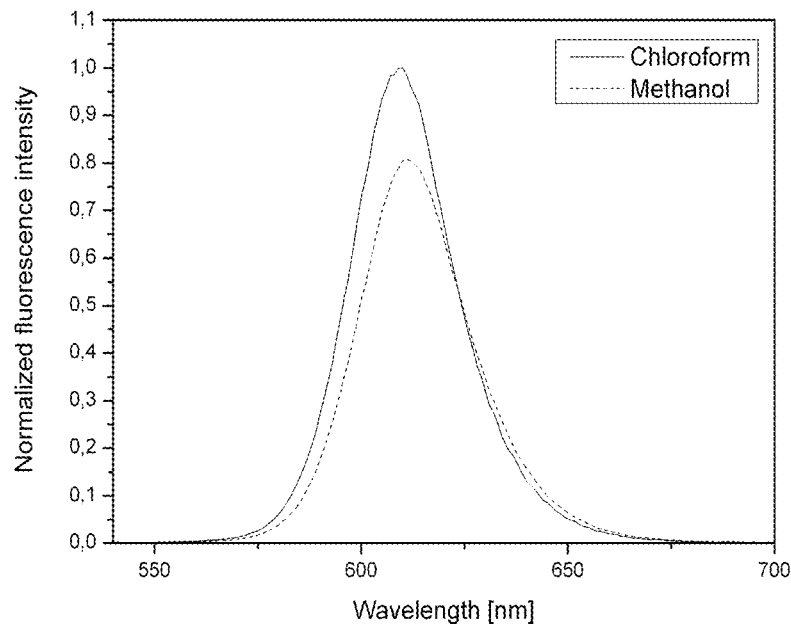
FIG. 14 shows the fluorescence spectra of PI-DETA coated CdSe/CdS/ZnS nanoparticles in chloroform (solid line) and the micelle encapsulated PI-DETA coated CdSe/CdS/ZnS nanoparticles in methanol (dotted line).

Composition of Micelle Encapsulated, Fluorescent, Trioctylphosphine/Trioctylphosphine Oxide Coated, 6 nm CdSe/CdS/ZnS Nanoparticles in Methanol 2.5 nmol of trioctylphosphine/trioctylphosphine oxide (TOP/TOPO) coated CdSe/CdS/ZnS core/shell/shell nanoparticles were precoated with 3.0 µmol (600 fold excess) of PI-DETA (3000 g/mol) and then precipitated by the addition of ethanol. Subsequently, the particles and 1.5 µmol (300 fold excess) of the PI-b-PEO diblock copolymer (13700 g/mol) were dissolved in 200 µL chloroform and then quickly injected into 2 mL methanol. The clear, slightly colored solution thus obtained indicated the colloidal dissolution of the nanoparticles in polymer micelles. Micelle formation was confirmed by dynamic light scattering (DLS; FIG. 12). As can be seen from the spectroscopic measurements (FIG. 13 and FIG. 14), the absorption and emission properties of the nanoparticles are virtually maintained.

Example 15

Figure 15:
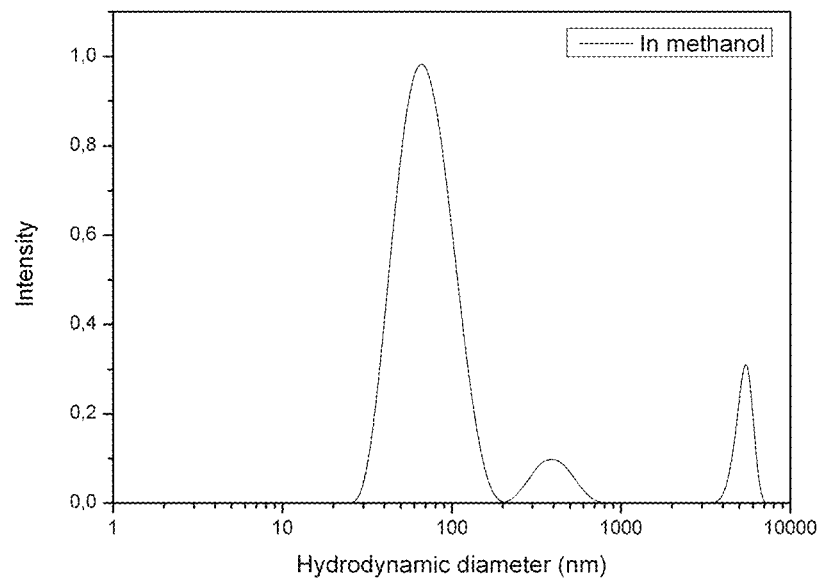
FIG. 15 shows the dynamic light scattering of micelle encapsulated CdSe/CdS nanoparticles in methanol.
Figure 16:
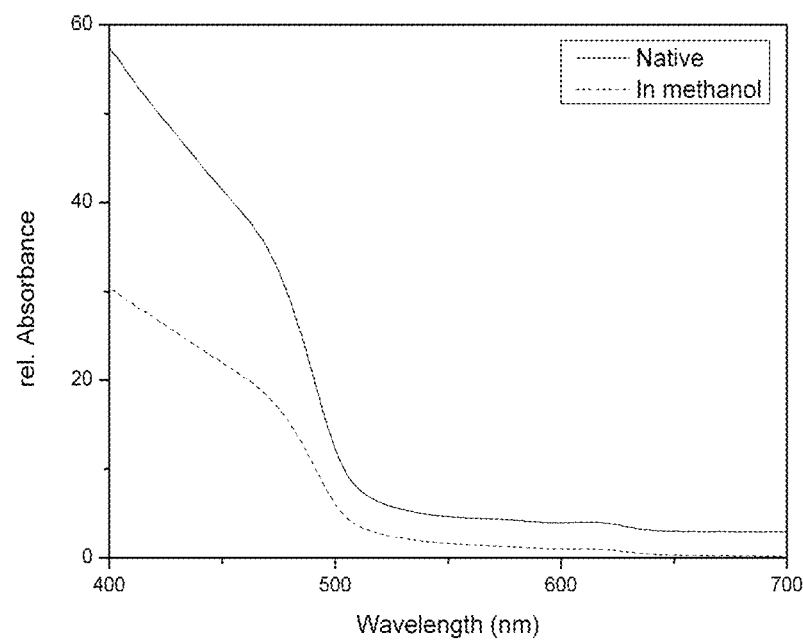
FIG. 16 shows the absorption spectra of CdSe/CdS nanoparticles in chloroform (solid line) and the micelle encapsulated CdSe/CdS nanoparticles in methanol (dotted line).
Figure 17:
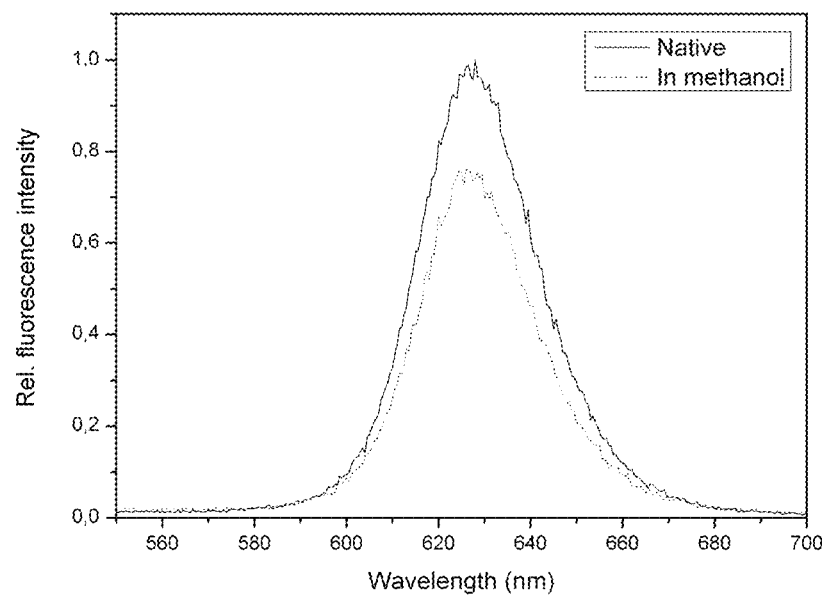
FIG. 17 shows the fluorescence spectra of native CdSe/CdS nanoparticles (solid line) and the micelle encapsulated CdSe/CdS nanoparticles in methanol (dotted line).

Composition of Micelle Encapsulated, Fluorescent, Oleic Acid/Oleylamine Coated, 8 nm CdSe/CdS Nanoparticles in Methanol 5 nmol of oleic acid/oleyalamine coated CdSe/CdS core/ shell nanoparticles in chloroform were mixed with 2.7 µmol (533 fold excess) of PI-b-PEO diblock copolymer (13700 g/mol) and adjusted to a total volume of 500 μL with chloroform. Subsequently the solution was quickly injected into 5000 μL of methanol and stirred for a minute. The clear, slightly colored solution thus obtained indicated the colloidal dissolution of the nanoparticles in polymer micelles. Micelle formation was confirmed by dynamic light scattering (DLS; FIG. 15). Absorption and emission properties of the nanoparticles are displayed in FIG. 16 and FIG. 17.

Example 16

Figure 18:
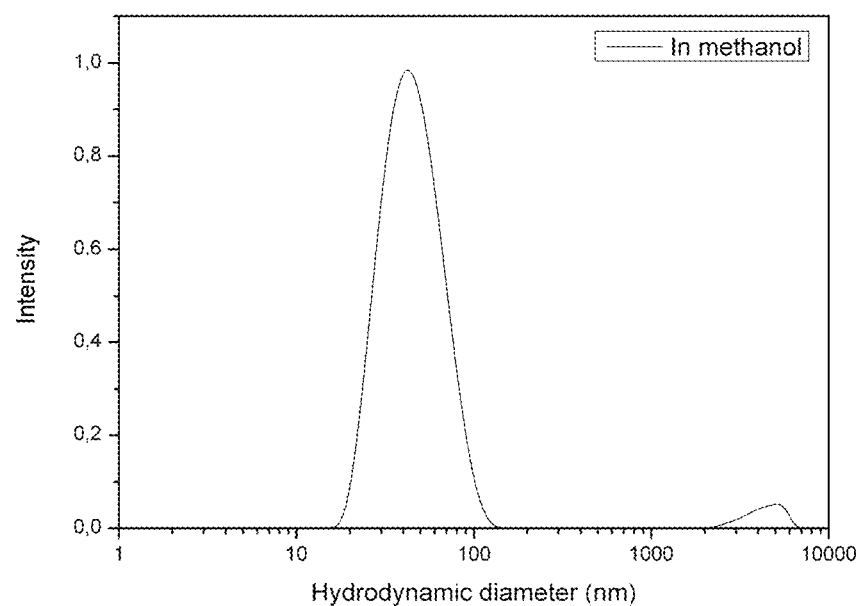
FIG. 18 shows the dynamic light scattering of micelle encapsulated CdSe/CdS rod-shaped nanoparticles in methanol.
Figure 19:
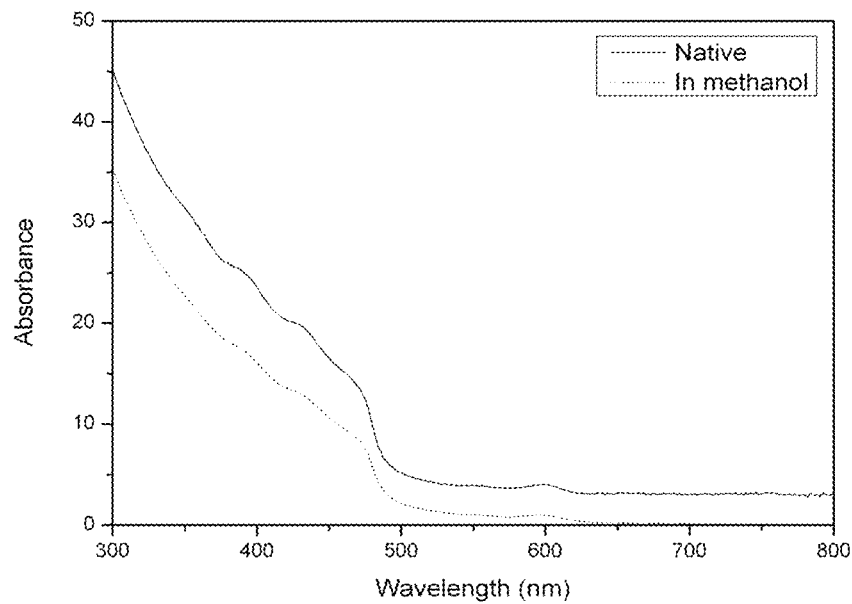
FIG. 19 shows the absorption spectra of CdSe/CdS rod-shaped nanoparticles in chloroform (solid line) and the micelle encapsulated CdSe/CdS rod-shaped nanoparticles in methanol (dotted line).
Figure 20:
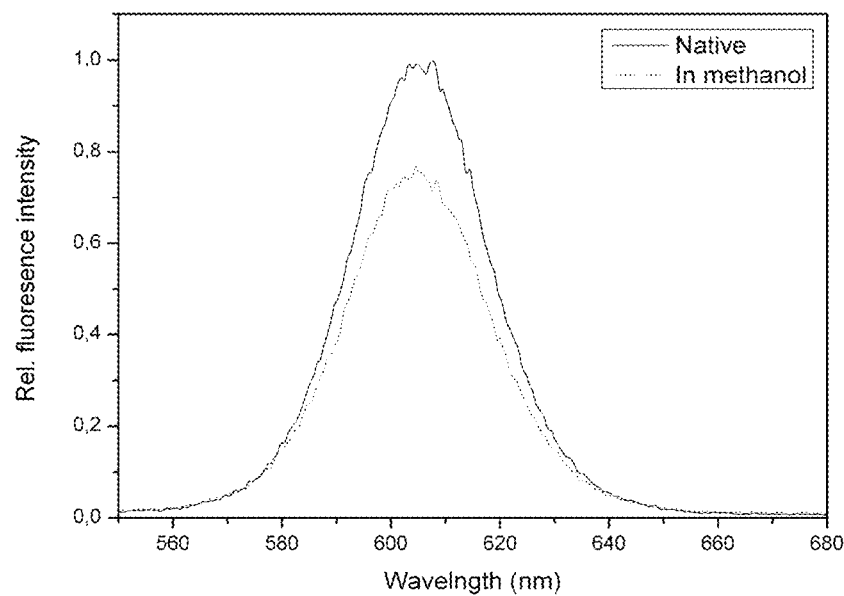
FIG. 20 shows the fluorescence spectra of native CdSe/CdS rod-shaped nanoparticles (solid line) and the micelle encapsulated CdSe/CdS rod-shaped nanoparticles in methanol (dotted line).

Composition of Micelle Encapsulated, Fluorescent, Octadecylphosphonic Acid Coated CdSe/CdS Rod-Shaped Nanoparticles in Methanol 5 nmol of octadecylphosphonic acid coated CdSe/CdS rod-shaped nanoparticles (4.8 nm in width; 22.2 nm in length) in chloroform were mixed with 8.8 μmol (1750 fold excess) of PI-b-PEO diblock copolymer (13700 g/mol) and adjusted to a total volume of 700 μL with chloroform. Subsequently the solution was quickly injected into 5000 μL of methanol and stirred for a minute. The clear, slightly colored solution thus obtained indicated the colloidal dissolution of the nanoparticles in polymer micelles. Micelle formation was confirmed by dynamic light scattering (DLS; FIG. 18). Again, the absorption and emission properties of the nanoparticles are only slightly influenced by the encapsulation process (FIG. 19 and FIG. 20).

Example 17

Figure 21:
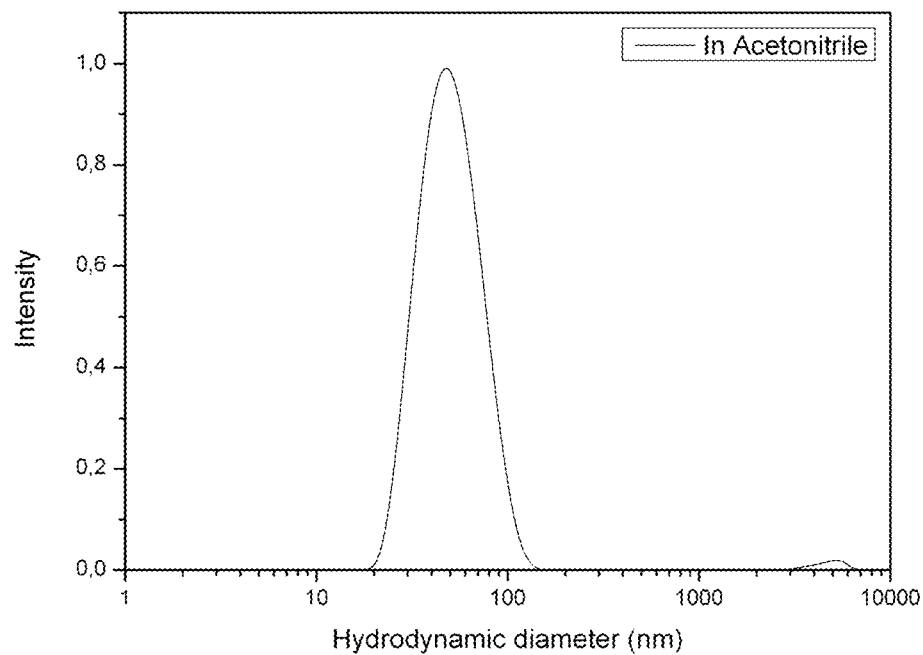
FIG. 21 shows the dynamic light scattering of micelle encapsulated CdSe/CdS rod-shaped nanoparticles in acetonitrile.
Figure 22:
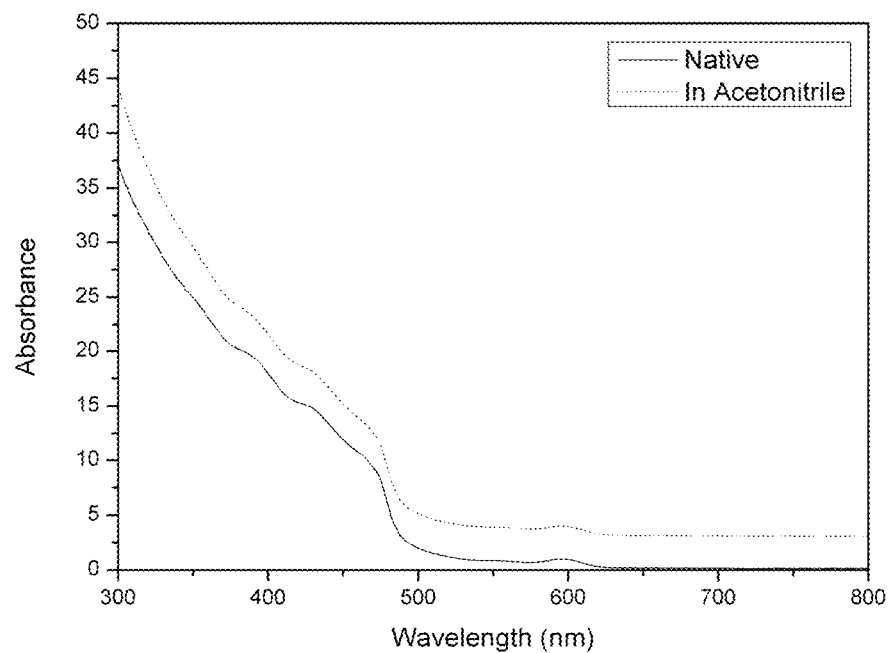
FIG. 22 shows the absorption spectra of CdSe/CdS rod-shaped nanoparticles in n-hexane (solid line) and the micelle encapsulated CdSe/CdS rod-shaped nanoparticles in acetonitrile (dotted line).
Figure 23:
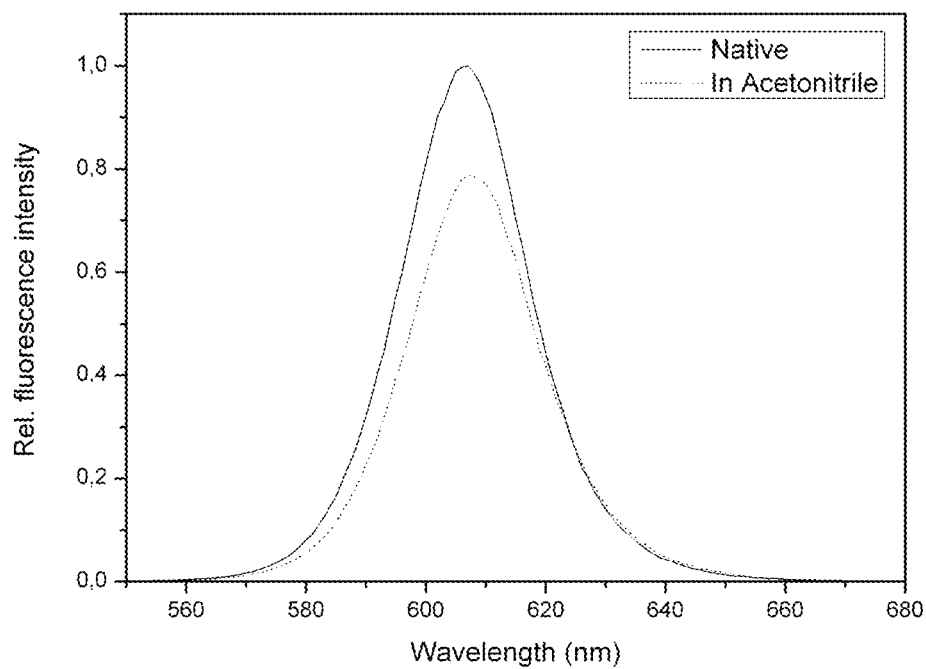
FIG. 23 shows the fluorescence spectra of native CdSe/CdS rod-shaped nanoparticles (solid line) and the micelle encapsulated CdSe/CdS rod-shaped nanoparticles in acetonitrile (dotted line).

Composition of Micelle Encapsulated, Fluorescent, Octadecylphosphonic Acid Coated CdSe/CdS Rod-Shaped Nanoparticles in Acetonitrile 5 nmol of octadecylphosphonic acid coated CdSe/CdS rod-shaped nanoparticles (4.8 nm in width; 22.2 nm in length) in chloroform were mixed with 8.8 μmol (1750 fold excess) of PI-b-PEO diblock copolymer (13700 g/mol) and adjusted to a total volume of 700 μL with chloroform. Subsequently the solution was quickly injected into 5000 μL of acetonitrile and stirred for a minute. The clear, slightly colored solution thus obtained indicated the colloidal dissolution of the nanoparticles in polymer micelles. Micelle formation was confirmed by dynamic light scattering (DLS; FIG. 21). Again, the absorption and emission properties of the nanoparticles are virtually maintained (FIG. 22 and FIG. 23).

Example 18

Figure 24:
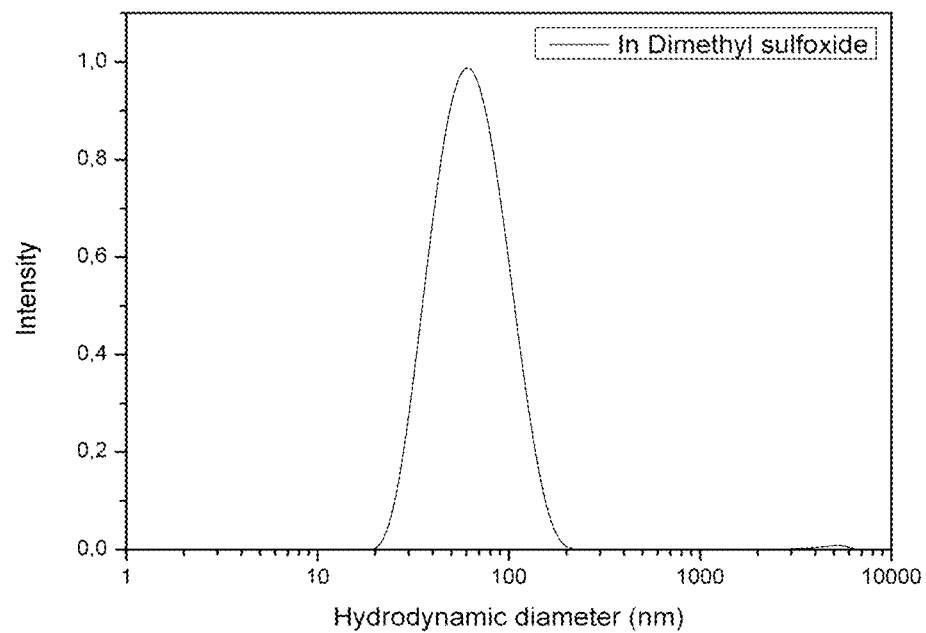
FIG. 24 shows the dynamic light scattering of micelle encapsulated CdSe/CdS rod-shaped nanoparticles in dimethyl sulfoxide.
Figure 25:
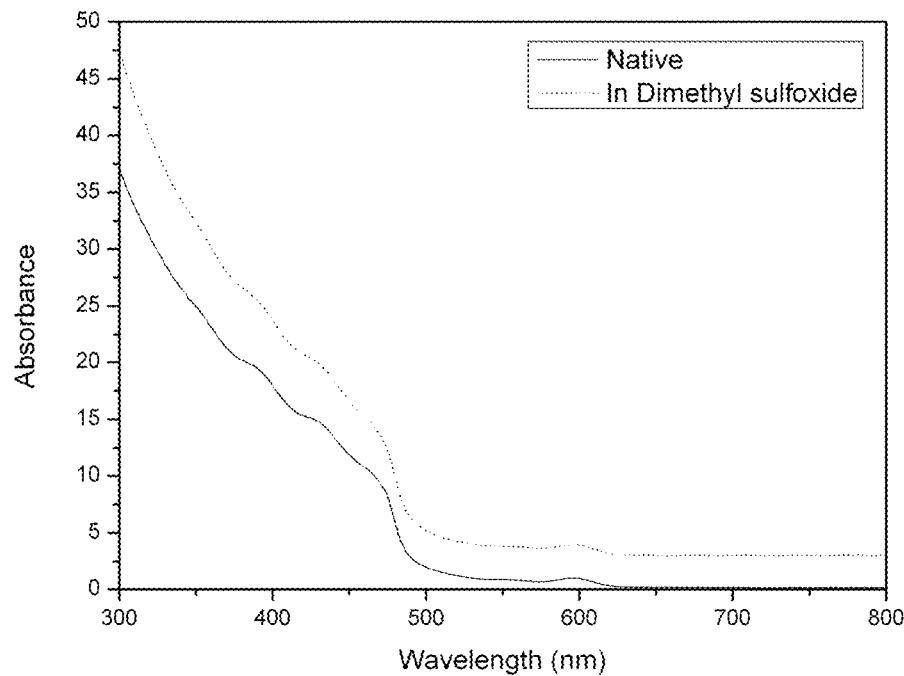
FIG. 25 shows the absoprtion spectra of CdSe/CdS rod-shaped nanoparticles in n-hexane (solid line) and the micelle encapsulated CdSe/CdS rod-shaped nanoparticles in dimethyl sulfoxide (dotted line).
Figure 26:
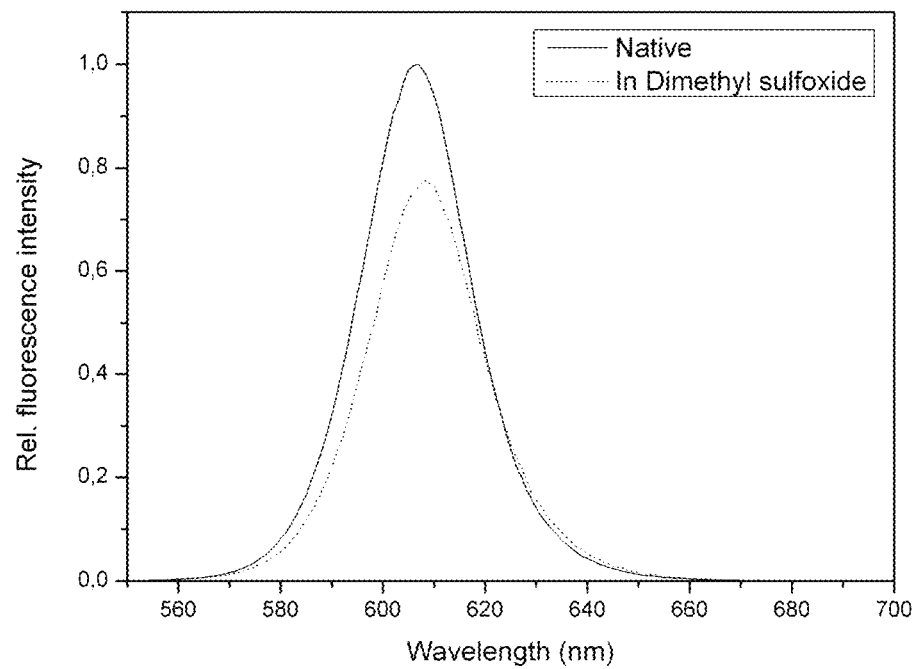
FIG. 26 shows the fluorescence spectra of native CdSe/CdS rod-shaped nanoparticles (solid line) and the micelle encapsulated CdSe/CdS rod-shaped nanoparticles in dimethyl sulfoxide (dotted line).

Composition of Micelle Encapsulated, Fluorescent, Octadecylphosphonic Acid Coated CdSe/CdS Rod-Shaped Nanoparticles in Dimethyl Sulfoxide 5 nmol of octadecylphosphonic acid coated CdSe/CdS rod-shaped nanoparticles (4.8 nm in width; 22.2 nm in length) in chloroform were mixed with 8.8 μmol (1750 fold excess) of PI-b-PEO diblock copolymer (13700 g/mol) and adjusted to a total volume of 700 μL with chloroform. Subsequently the solution was quickly injected into 5000 μL of Dimethyl sulfoxide and stirred for a minute. The clear, slightly colored solution thus obtained indicated the colloidal dissolution of the nanoparticles in polymer micelles. Micelle formation was confirmed by dynamic light scattering (DLS; FIG. 24). Again, the absorption and emission properties of the nanoparticles are virtually maintained (FIG. 25 and FIG. 26).

Example 19

Figure 27:
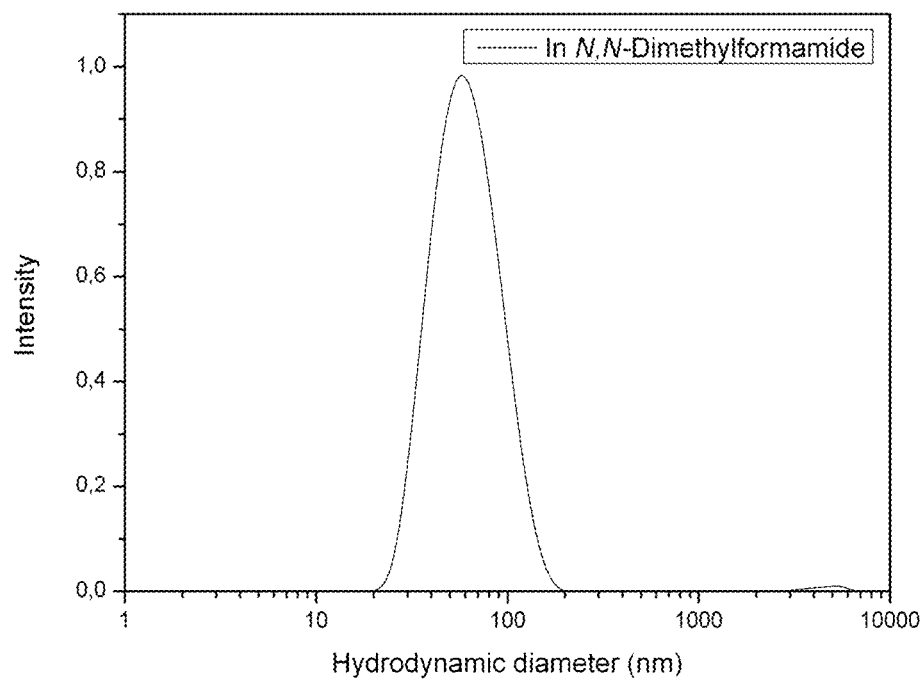
FIG. 27 shows the dynamic light scattering of micelle encapsulated CdSe/CdS rod-shaped nanoparticles in N,N-dimethylformamide.
Figure 28:
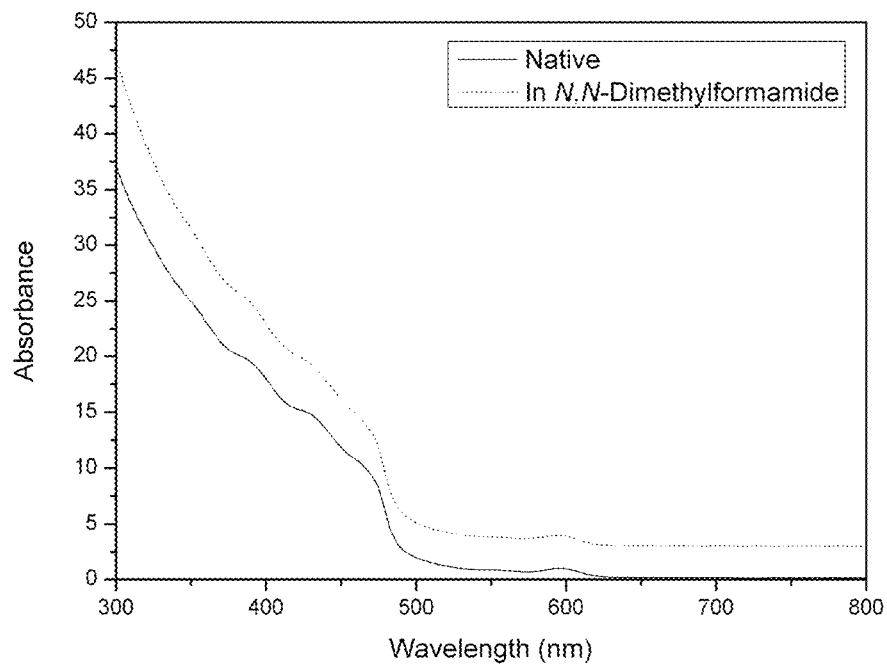
FIG. 28 shows the absoprtion spectra of CdSe/CdS rod-shaped nanoparticles in n-hexane (solid line) and the micelle encapsulated CdSe/CdS rod-shaped nanoparticles in N,N-dimethylformamide (dotted line).
Figure 29:
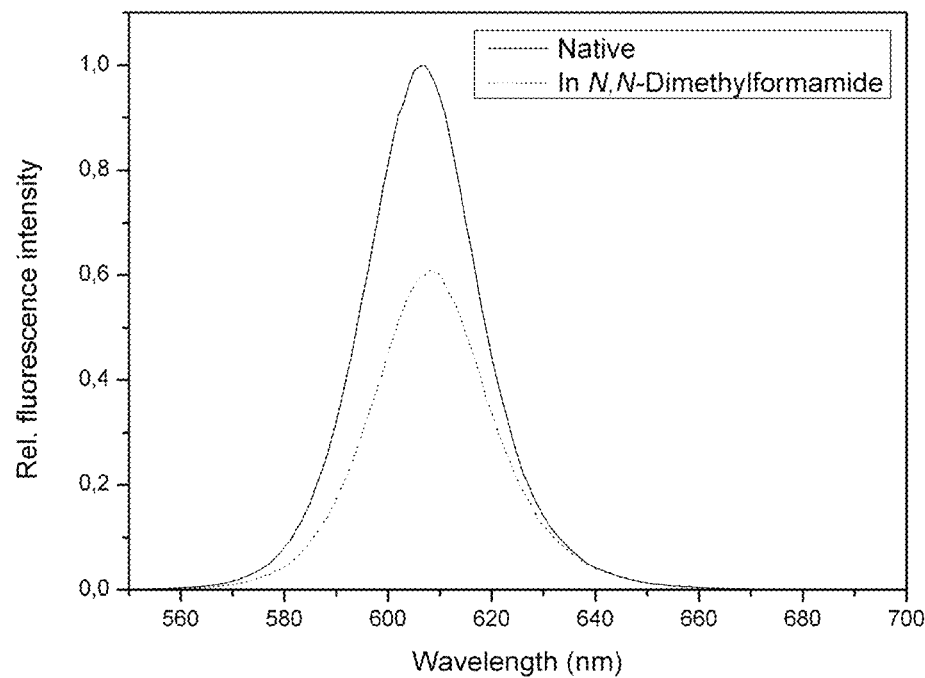
FIG. 29 shows the fluorescence spectra of native CdSe/CdS rod-shaped nanoparticles (solid line) and the micelle encapsulated CdSe/CdS rod-shaped nanoparticles in N,N-dimethylformamide (dotted line).

Composition of Micelle Encapsulated, Fluorescent, Octadecylphosphonic Acid Coated CdSe/CdS Rod-Shaped Nanoparticles in N,N-Dimethylformamide 5 nmol of octadecylphosphonic acid coated CdSe/CdS rod-shaped nanoparticles (4.8 nm in width; 22.2 nm in length) in chloroform were mixed with 8.8 μmol (1750 fold excess) of PI-b-PEO diblock copolymer (13700 g/mol) and adjusted to a total volume of 700 μL with chloroform. Subsequently the solution was quickly injected into 5000 μL of N,N-dimethylformamide and stirred for a minute. The clear, slightly colored solution thus obtained indicated the colloidal dissolution of the nanoparticles in polymer micelles. Micelle formation was confirmed by dynamic light scattering (DLS; FIG. 27). The absorption and emission properties are displayed in FIG. 28 and FIG. 29.

Example 20

Composition of Micelle Encapsulated, Fluorescent, Octadecylphosphonic Acid Coated CdSe/CdS Rod-Shaped Nanoparticles in [BMIM][BF$_4$]

Figure 30:
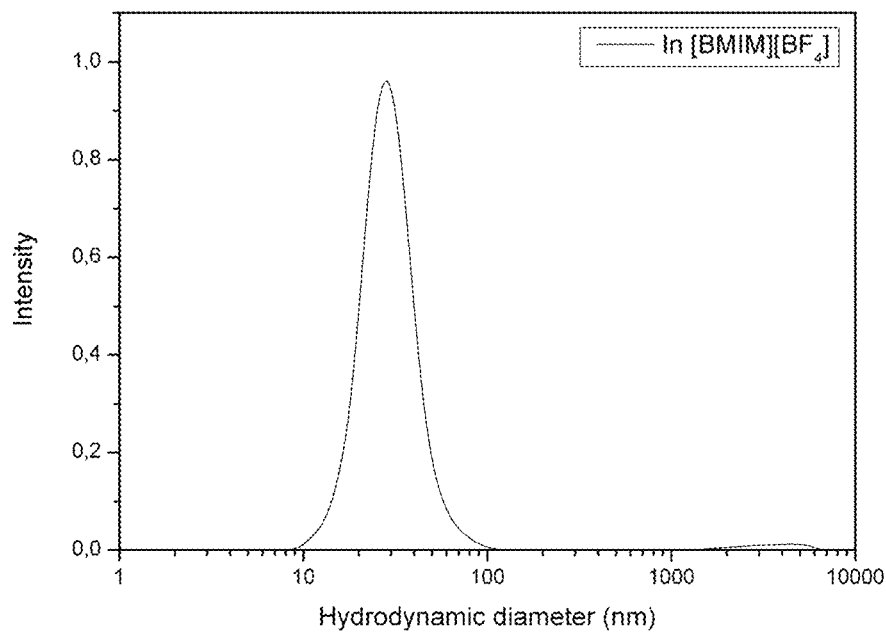
FIG. 30 shows the dynamic light scattering of micelle encapsulated CdSe/CdS rod-shaped nanoparticles in the ionic liquid [BMIM][BF$_4$].
Figure 31:
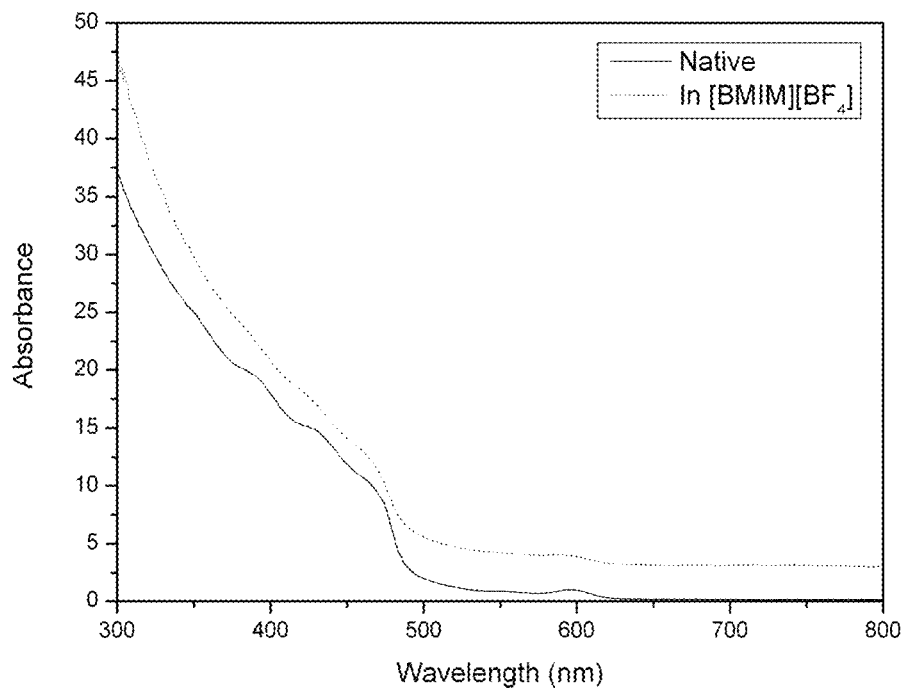
FIG. 31 shows the absoprtion spectra of CdSe/CdS rod-shaped nanoparticles in n-hexane (solid line) and the micelle encapsulated CdSe/CdS rod-shaped nanoparticles in [BMIM][BF$_4$] (dotted line).
Figure 32:
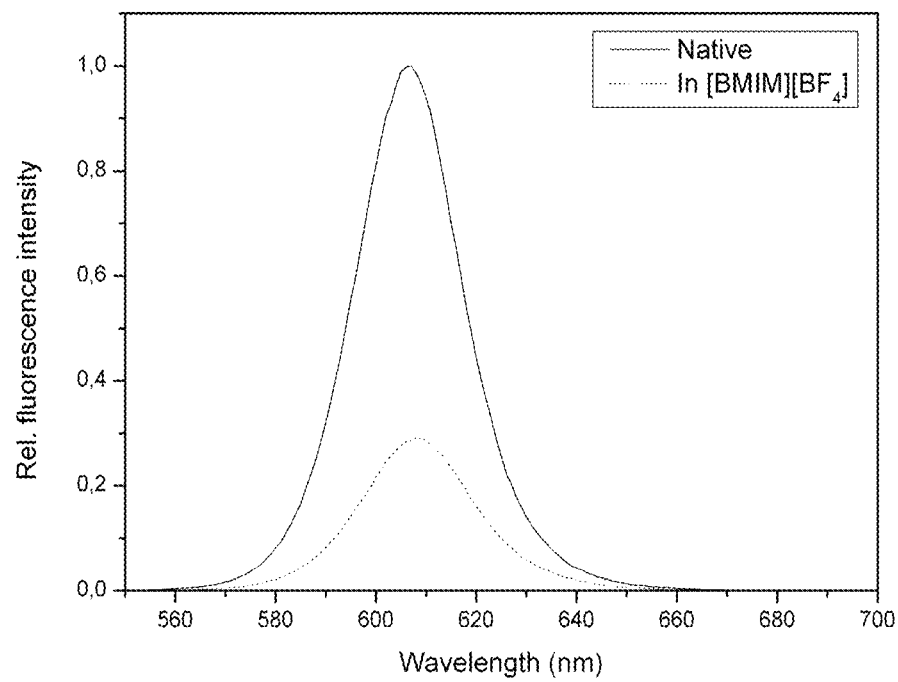
FIG. 32 shows the fluorescence spectra of native CdSe/CdS rod-shaped nanoparticles (solid line) and the micelle encapsulated CdSe/CdS rod-shaped nanoparticles in [BMIM][BF$_4$] (dotted line).

1 nmol of octadecylphosphonic acid coated CdSe/CdS rod-shaped nanoparticles (4.8 nm in width; 22.2 nm in length) in chloroform were mixed with 1.8 μmol (1750 fold excess) of PI-b-PEO diblock copolymer (13700 g/mol) and adjusted to a total volume of 140 μL with chloroform. Subsequently the solution was quickly injected into 1500 μL of ionic liquid [BMIM][BF$_4$] and stirred for a couple of minutes. The mixing process is very slow due to the high viscosity of the ionic liquid. To fasten this process, the mixture was gently heated (ca. 50° C.) while stirring. The clear, slightly colored solution thus obtained indicated the colloidal dissolution of the nanoparticles in polymer micelles. Micelle formation was confirmed by dynamic light scattering (DLS; FIG. 30). The absorption and emission properties of the nanoparticles are displayed in FIG. 31 and FIG. 32.

Example 21

Figure 33:
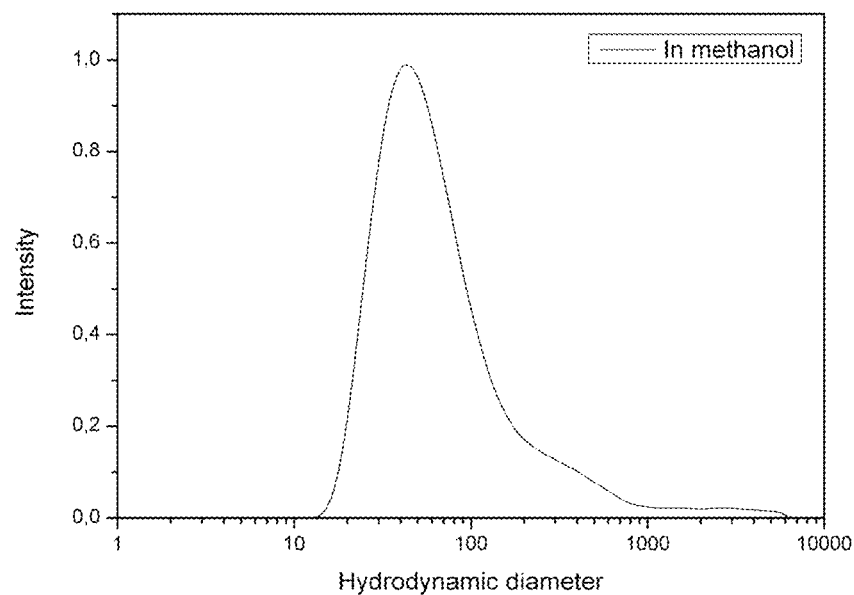
FIG. 33 shows the dynamic light scattering of micelle encapsulated InP/ZnS nanoparticles in methanol.
Figure 34:
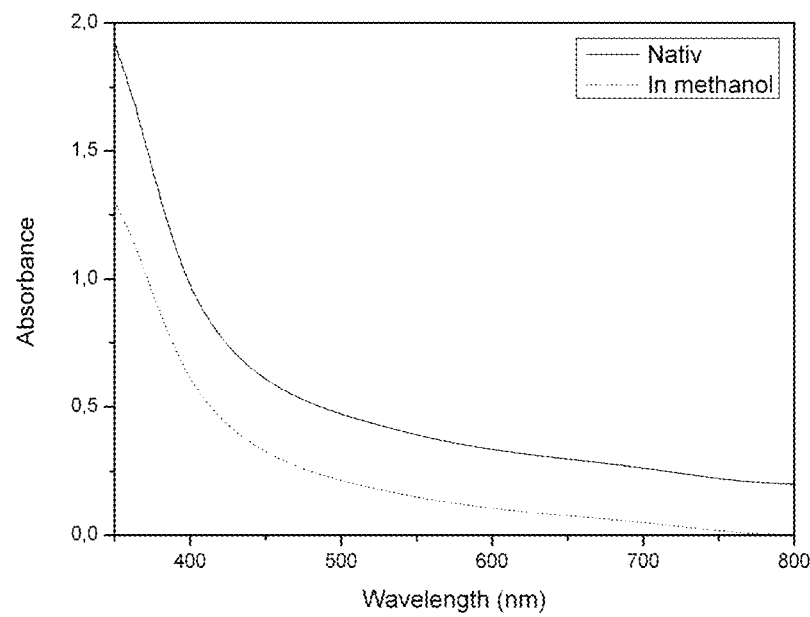
FIG. 34 shows the absorption spectra of InP/ZnS nanoparticles in toluene (solid line) and the micelle encapsulated InP/ZnS nanoparticles in methanol (dotted line).
Figure 35:
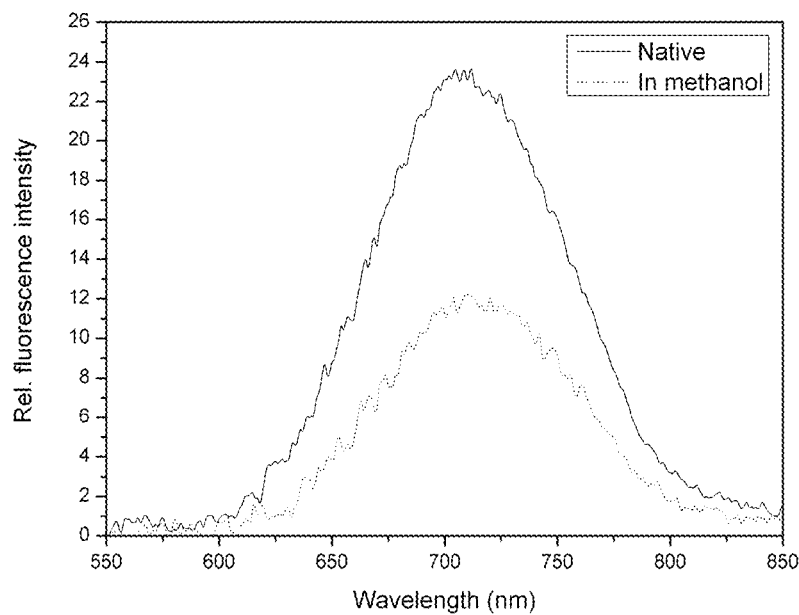
FIG. 35 shows the fluorescence spectra of native InP/ZnS nanoparticles (solid line) and the micelle encapsulated InP/ZnS nanoparticles in methanol (dotted line).

Composition of Micelle Encapsulated, Fluorescent, Trioctylphosphine Coated, 5 nm InP/ZnS Nanoparticles in Methanol 5 nmol of hexdecylamine coated InP/ZnS nanoparticles in toluene were completely dried under a gentle nitrogen flow. The solid residue was dissolved in 300 μL chloroform and mixed with 2.5 μmol (500 fold excess) of PI-b-PEO. The resulting solution was quickly injected into 2500 of methanol and stirred for a minute. The clear, slightly colored solution thus obtained indicated the colloidal dissolution of the nanoparticles in polymer micelles. Micelle formation was confirmed by dynamic light scattering (DLS; FIG. 33). The absorption and emission properties of the nanoparticles are displayed in FIG. 34 and FIG. 35).

Example 22

Composition of Micelle Encapsulated, Fluorescent, Hexadecanethiol Coated, 5 nm InP/ZnS Nanoparticles in Methanol 30 nmol of hexadecylamine coated InP/ZnS nanoparticles were incubated with 90 μmol (3000 fold excess) hexadecanethiol. After 24 h of incubation the nanoparticles were precipitated from the solution by the addition of the same volume of methanol. The supernatant was discarded and the pellet was dissolved in 300 µL chloroform.

Figure 36:
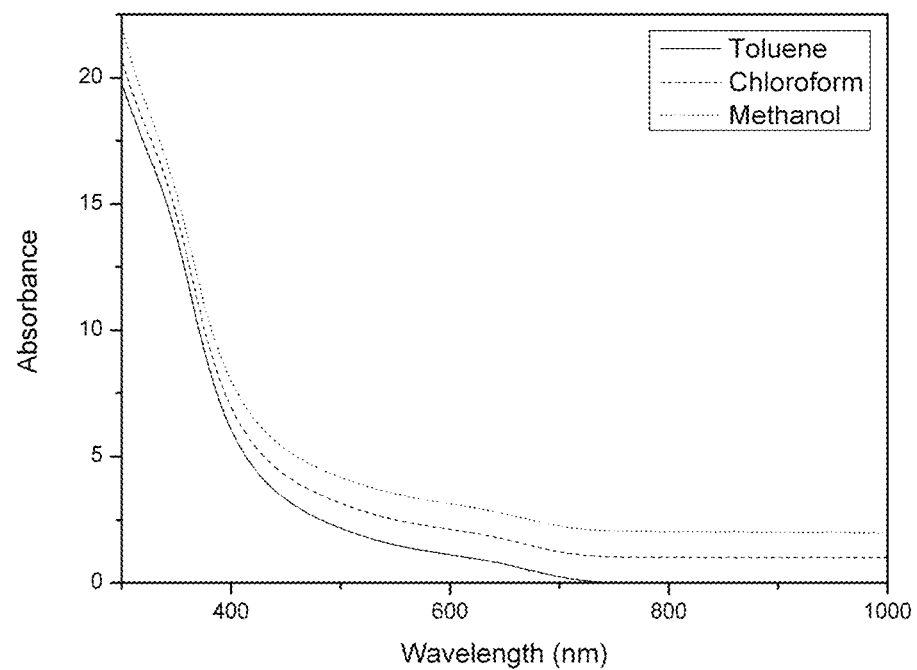
FIG. 36 shows the absorption spectra of native InP/ZnS nanoparticles (solid line), hexadecylamine coated InP/ZnS nanoparticles (dashed line) and the micelle encapsulated hexadecylamine coated InP/ZnS nanoparticles in methanol (dotted line).
Figure 37:
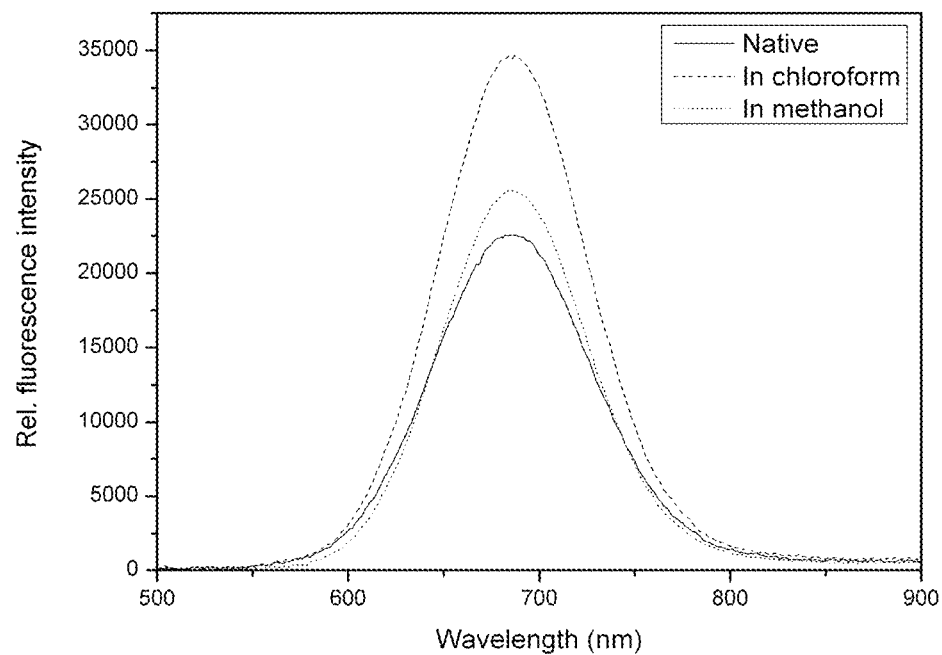
FIG. 37 shows the fluorescence spectra of native InP/ZnS nanoparticles (solid line), hexadecylamine coated InP/ZnS nanoparticles (dashed line) and the micelle encapsulated hexadecylamine coated InP/ZnS nanoparticles in methanol (dotted line).

100 µL (approx. 10 nmol) of the hexadecanethiol coated InP/ZnS nanoparticles were mixed with 5 µmol (500 fold excess) of PI-b-PEO diblock copolymer (13700 g/mol) and adjusted to a total volume of 500 µL with chloroform. Subsequently the solution was quickly injected into 5000 µL of methanol and stirred for a minute. The clear, slightly colored solution thus obtained indicated the colloidal dissolution of the nanoparticles in polymer micelles. Again, the absorption and emission properties of the nanoparticles are even improved by the encapsulation process (FIG. 36 and FIG. 37).

Example 23

Figure 38:
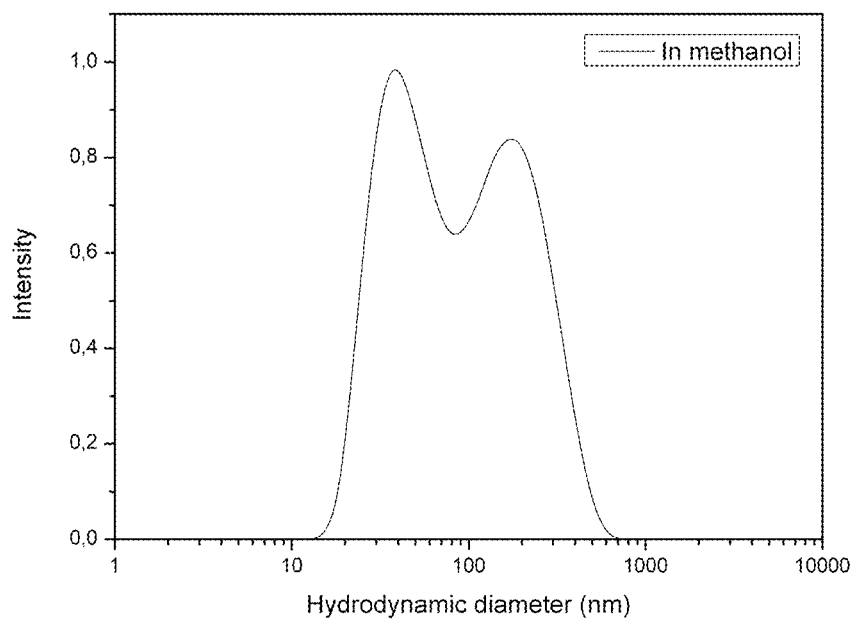
FIG. 38 shows the dynamic light scattering of micelle encapsulated CuInSe/ZnS nanoparticles in methanol.
Figure 39:
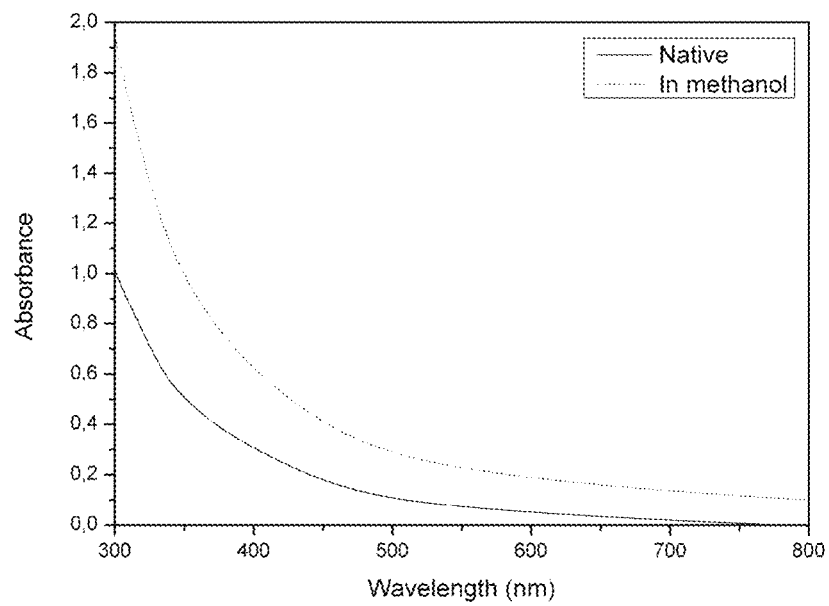
FIG. 39 shows the absorption spectra of CuInSe/ZnS nanoparticles in chloroform (solid line) and the micelle encapsulated CuInSe/ZnS nanoparticles in methanol (dotted line).
Figure 40:
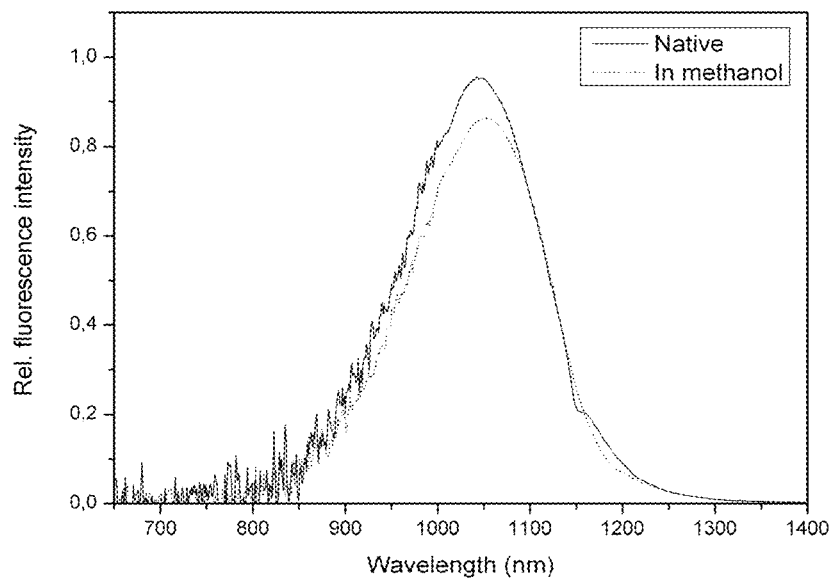
FIG. 40 shows the fluorescence spectra of native CuInSe/ZnS nanoparticles (solid line) and the micelle encapsulated CuInSe/ZnS nanoparticles in methanol (dotted line).

Composition of Micelle Encapsulated, Fluorescent, Trioctylphosphine/Trioctylphosphone Oxide Coated CuInSe/ZnS Nanoparticles in Methanol 50 µL of a stock solution of CuInSe/ZnS nanoparticles in chloroform were mixed with 0.060 g PI-b-PEO (13700 g/mol) and adjusted to a total volume of 250 µL with chloroform. Subsequently the solution was quickly injected into 2500 µL of methanol and stirred for a minute. The clear, slightly colored solution thus obtained indicated the colloidal dissolution of the nanoparticles in polymer micelles. Micelle formation was confirmed by dynamic light scattering (DLS; FIG. 38). Again, the absorption and emission properties of the nanoparticles are almost maintained (FIG. 39 and FIG. 40).

Example 24

Figure 41:
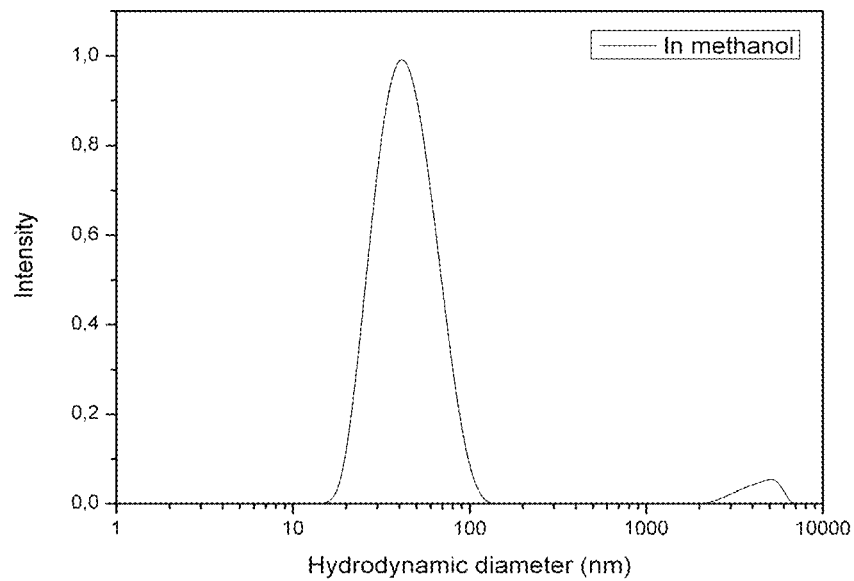
FIG. 41 shows the dynamic light scattering of micelle encapsulated Au nanoparticles in methanol.
Figure 42:
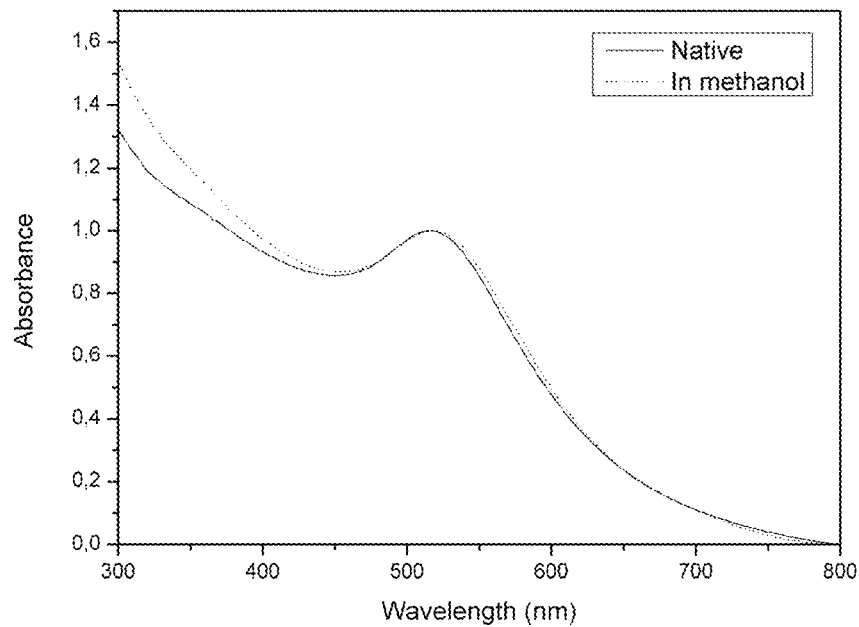
FIG. 42 shows the absorption spectra of Au nanoparticles in toluene (solid line) and the micelle encapsulated Au nanoparticles in methanol (dotted line).

Composition of Micelle Encapsulated, Plasmonic, Dodecanethiol Coated, 4 nm Au Nanoparticles in Methanol 3 nmol of dodecanethiol coated Au nanoparticles in toluene were dried in a gentle nitrogen flow. The resulting solid was dissolved in 300 µL of a solution containing 1.5 µmol (500 fold excess) PI-b-PEO in dichloromethane. The resulting solution was quickly injected into 2500 µL of methanol and stirred for a minute. The clear, slightly colored solution thus obtained indicated the colloidal dissolution of the nanoparticles in polymer micelles. Micelle formation was confirmed by dynamic light scattering (DLS; FIG. 41). The plasmon band of the gold nanoparticles is slightly shifted, possibly due to the change of the dielectric environment (FIG. 42).

Example 25

Figure 43:
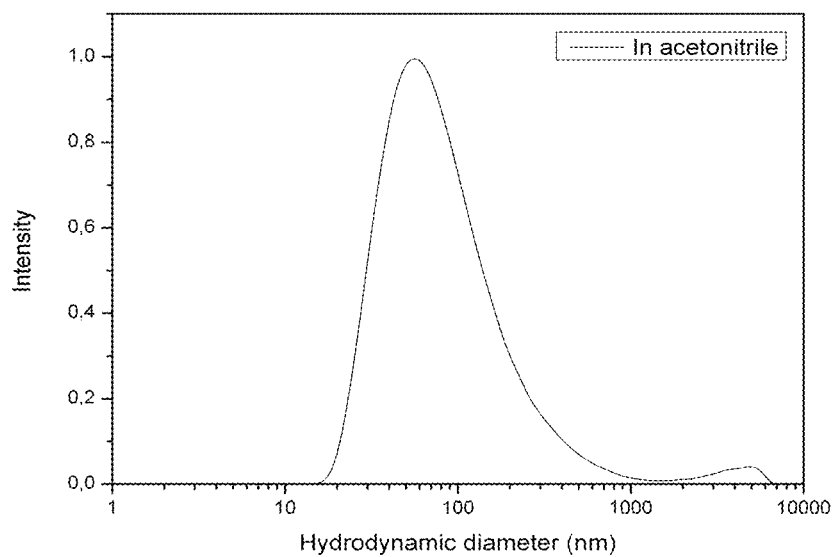
FIG. 43 shows the dynamic light scattering of micelle encapsulated Au nanoparticles in acetonitrile.
Figure 44:
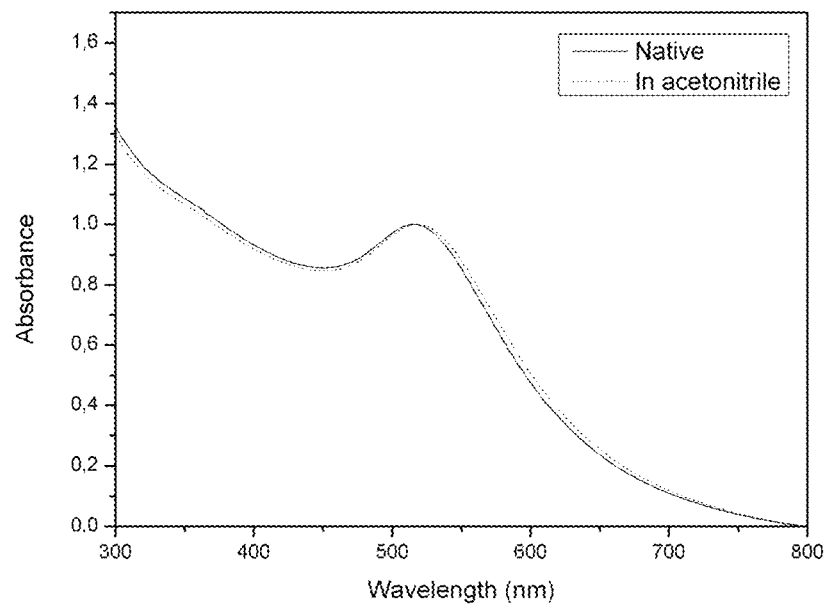
FIG. 44 shows the absorption spectra of Au nanoparticles in toluene (solid line) and the micelle encapsulated Au nanoparticles in acetonitrile (dotted line).

Composition of Micelle Encapsulated, Plasmonic, Dodecanethiol Coated, 4 nm Au Nanoparticles in Acetonitrile 3 nmol of freshly precipitated dodecanethiol coated Au nanoparticles in 300 µL CHCl$_3$ were mixed with 1.5 µmol (500 fold excess) PI-b-PEO. The resulting solution was quickly injected into 3000 µL of acetonitrile and stirred for a minute. The clear, slightly colored solution thus obtained indicated the colloidal dissolution of the nanoparticles in polymer micelles. Micelle formation was confirmed by dynamic light scattering (DLS; FIG. 43). The plasmon band of the gold nanoparticles is slightly shifted, possibly due to the change of the dielectric environment (FIG. 44).

Example 26

Figure 45:
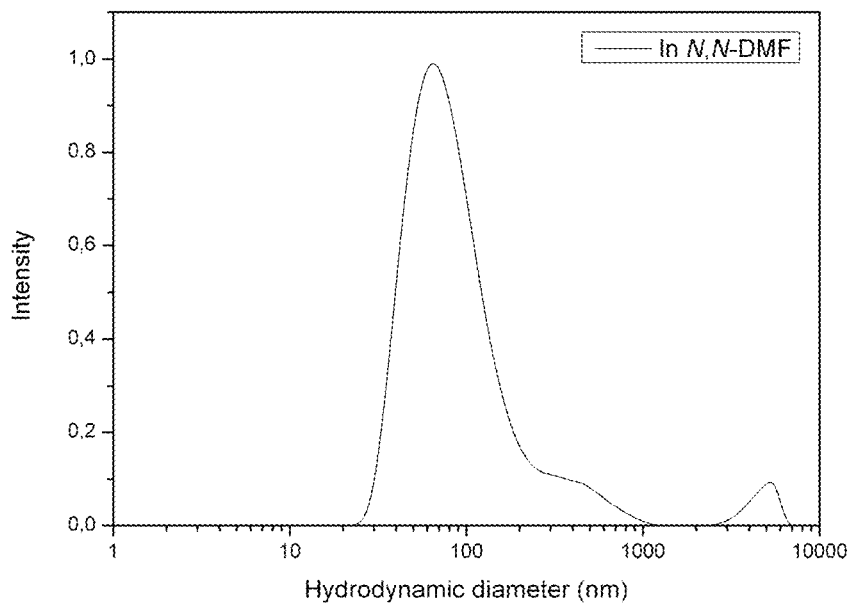
FIG. 45 shows the dynamic light scattering of micelle encapsulated Au nanoparticles in N,N-dimethylformamide.
Figure 46:
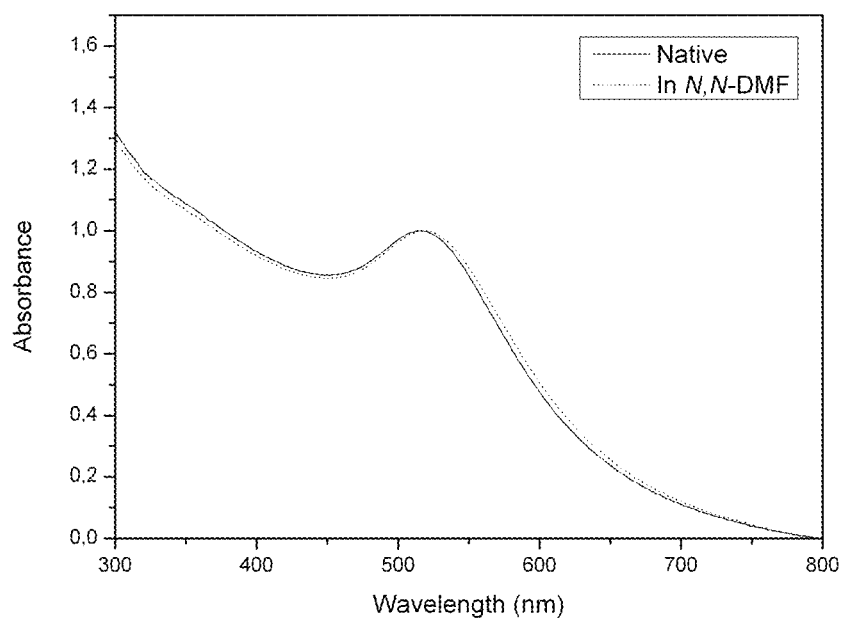
FIG. 46 shows the absorption spectra of Au nanoparticles in toluene (solid line) and the micelle encapsulated Au nanoparticles in N,N-dimethylformamide (dotted line).

Composition of Micelle Encapsulated, Plasmonic, Dodecanethiol Coated, 4 nm Au Nanoparticles in N,N-Dimethylformamide 3 nmol of freshly precipitated dodecanethiol coated Au nanoparticles in 300 µL CHCl$_3$ were mixed with 1.5 µmol (500 fold excess) PI-b-PEO. The resulting solution was quickly injected into 3000 µL of N,N-dimethylformamide (N,N-DMF) and stirred for a minute. The clear, slightly colored solution thus obtained indicated the colloidal dissolution of the nanoparticles in polymer micelles. Micelle formation was confirmed by dynamic light scattering (DLS; FIG. 45). The plasmon band of the gold nanoparticles is slightly shifted, possibly due to the change of the dielectric environment (FIG. 46).

Example 27

Figure 47:
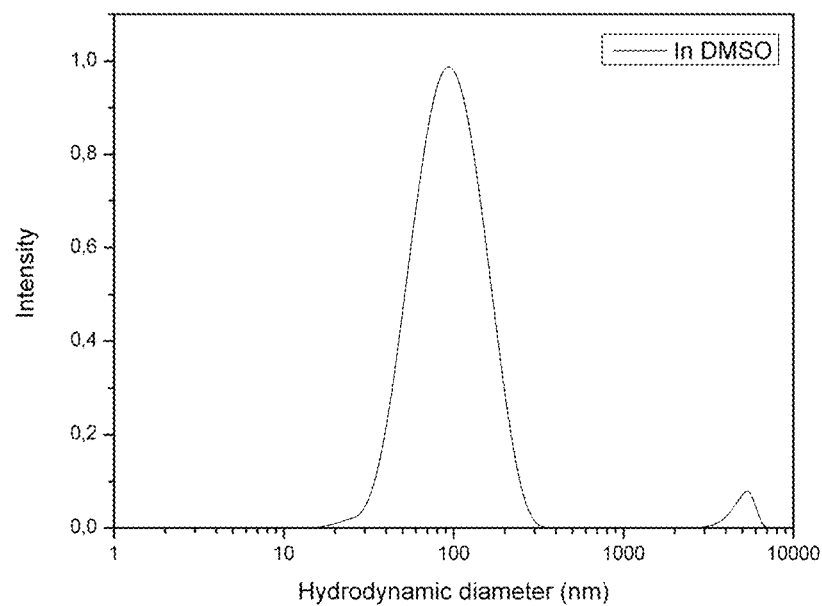
FIG. 47 shows the dynamic light scattering of micelle encapsulated Au nanoparticles in DMSO.
Figure 48:
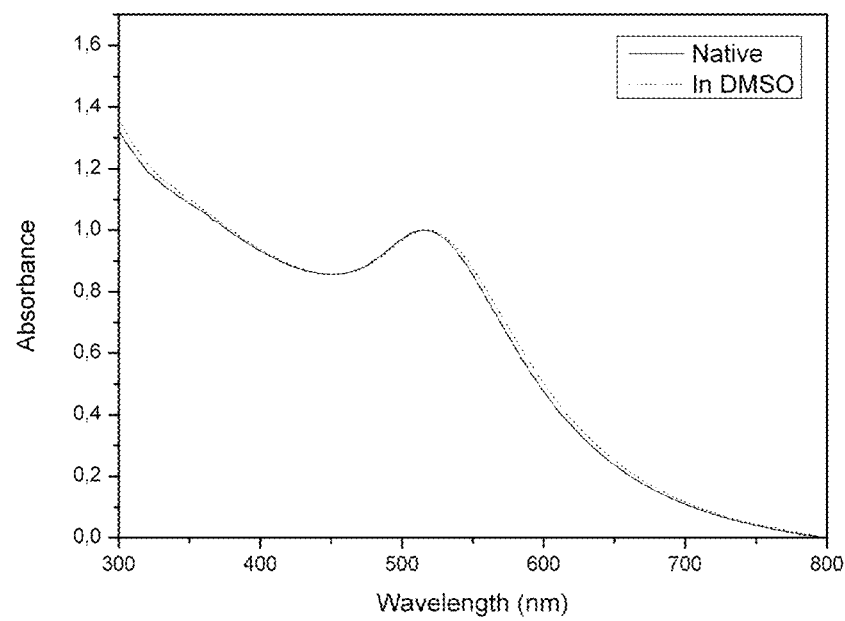
FIG. 48 shows the absorption spectra of Au nanoparticles in toluene (solid line) and the micelle encapsulated Au nanoparticles in DMSO (dotted line).

Composition of Micelle Encapsulated, Plasmonic, Dodecanethiol Coated, 4 nm Au Nanoparticles in Dimethylsulfoxide 3 nmol of freshly precipitated dodecanethiol coated Au nanoparticles in 300 µL CHCl$_3$ were mixed with 1.5 µmol (500 fold excess) PI-b-PEO. The resulting solution was quickly injected into 3000 µL of dimethylsulfoxide (DMSO) and stirred for a minute. The clear, slightly colored solution thus obtained indicated the colloidal dissolution of the nanoparticles in polymer micelles. Micelle formation was confirmed by dynamic light scattering (DLS; FIG. 47). The Plasmon band of the gold nanoparticles is slightly shifted, possibly due to the change of the dielectric environment (FIG. 48).

Example 28

Composition of Micelle Encapsulated, Plasmonic, Dodecanethiol Coated, 4 nm Au Nanoparticles in 1-Butyl-3-Methylimidazolium Tetrafluoroborate ([BMIM][BF$_4$])

Figure 49:
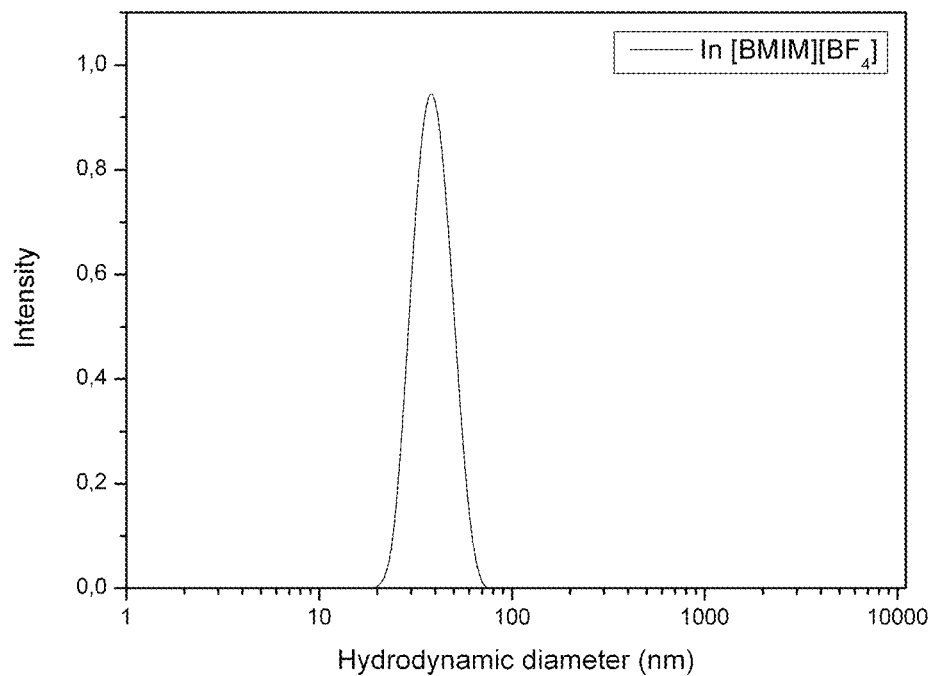
FIG. 49 shows the dynamic light scattering of micelle encapsulated Au nanoparticles in [BMIM][BF$_4$].
Figure 50:
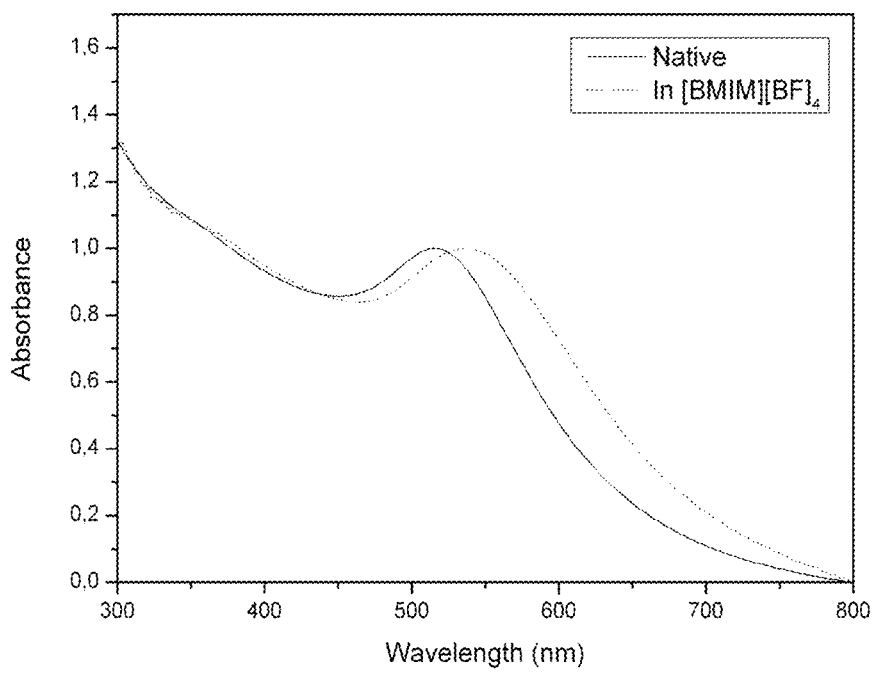
FIG. 50 shows the absorption spectra of Au nanoparticles in toluene (solid line) and the encapsulated Au nanoparticles in ionic liquid [BMIM][BF$_4$] (dotted line).

1 nmol of freshly precipitated dodecanethiol coated Au nanoparticles in 200 µL CHCl$_3$ was mixed with 1.5 µmol (1500 fold excess) PI-b-PEO. The resulting solution was quickly injected into 1000 µL of [BMIM][BF$_4$] and stirred for a minute. Subsequently the mixture was vigorously stirred and heated carefully to evaporate the remaining CHCl$_3$. After cooling to room temperature a clear, slightly colored solution was obtained indicating the colloidal dissolution of, the nanoparticles in polymer micelles. Micelle formation was confirmed by dynamic light scattering (DLS; FIG. 49). The plasmon band of the gold nanoparticles is shifted, possibly due to the change of the dielectric environment (FIG. 50).

Example 29

Figure 51:
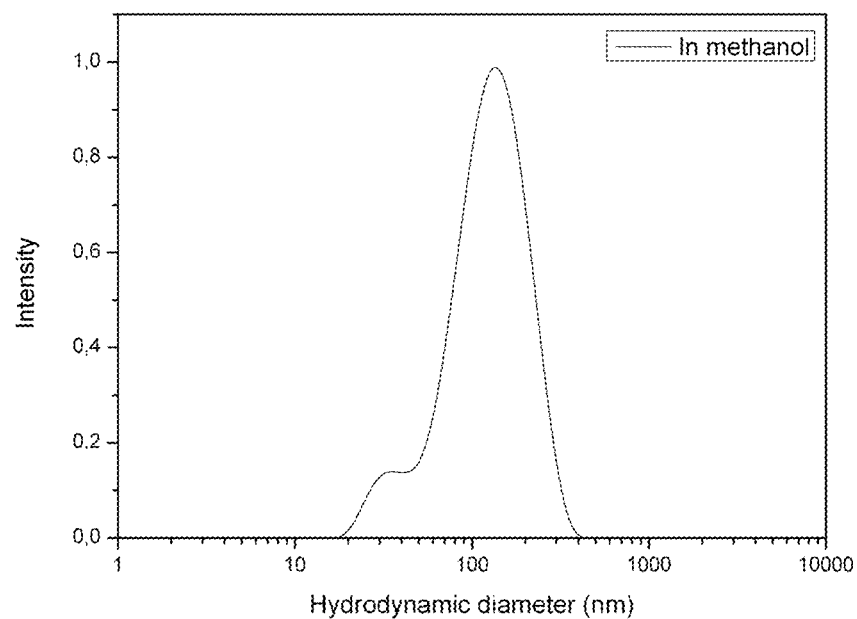
FIG. 51 shows the dynamic light scattering of micelle encapsulated Fe$_x$O$_y$ nanoparticles in methanol.

Composition of Micelle Encapsulated Magnetic, Oleic Acid, 10 nm Fe$_x$O$_y$ Nanoparticles in Methanol 5 nmol Fe$_x$O$_y$ nanoparticles in toluene were precipitated by the addition of an equal volume of methanol. The cloudy mixture was centrifuged (6000×g; 10 min) and the supernatant was discarded. The remaining pellet was dissolved in 500 µL chloroform and mixed with 6.9 µmol (1390 fold excess) PI-b-PEO. The resulting solution was quickly injected into 5000 µL methanol and stirred for a minute. The clear, brownish colored solution thus obtained indicated the colloidal dissolution of the nanoparticles in polymer micelles. Micelle formation was confirmed by dynamic light scattering (DLS; FIG. 51).

Example 30

Figure 52:
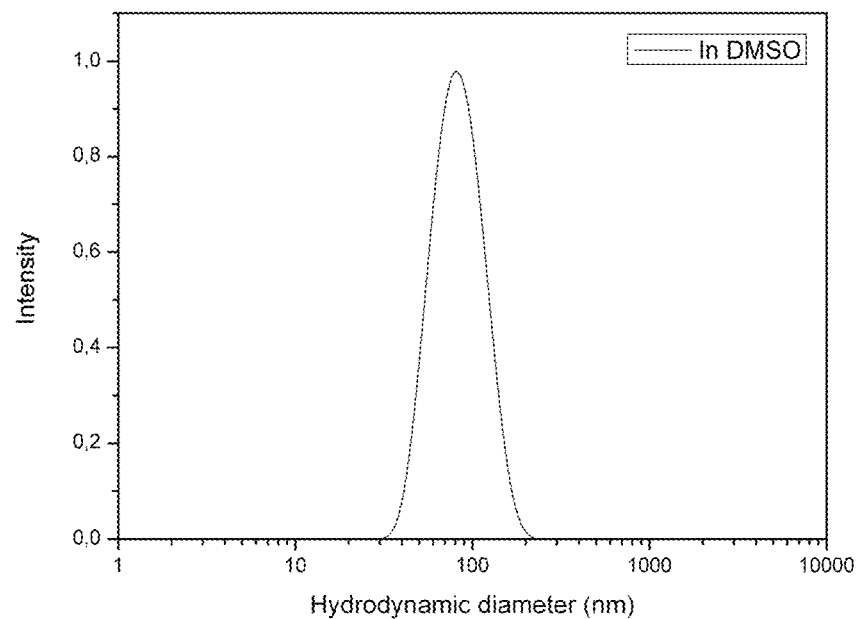
FIG. 52 shows the dynamic light scattering of micelle encapsulated Fe$_x$O$_y$ nanoparticles in DMSO.

Composition of Micelle Encapsulated Magnetic, Oleic Acid, 10 nm Fe$_x$O$_y$ Nanoparticles in Dimethyl Sulfoxide 5 nmol Fe$_x$O$_y$ nanoparticles in toluene were precipitated by the addition of an equal volume of methanol. The cloudy mixture was centrifuged (6000×g; 10 min) and the supernatant was discarded. The remaining pellet was dissolved in 1000 µL chloroform and mixed with 6.9 µmol (1390 fold excess) PI-b-PEO. The resulting solution was quickly injected into 9000 µL DMSO and stirred for a minute. The clear, brownish colored solution thus obtained indicated the colloidal dissolution of the nanoparticles in polymer micelles. Micelle formation was confirmed by dynamic light scattering (DLS; FIG. 52).

Example 31

Composition of Micelle Encapsulated Magnetic, Oleic Acid, 10 nm $Fe_xO_y$ Nanoparticles in N,N-Dimethylformamide (DMF)

Figure 53:
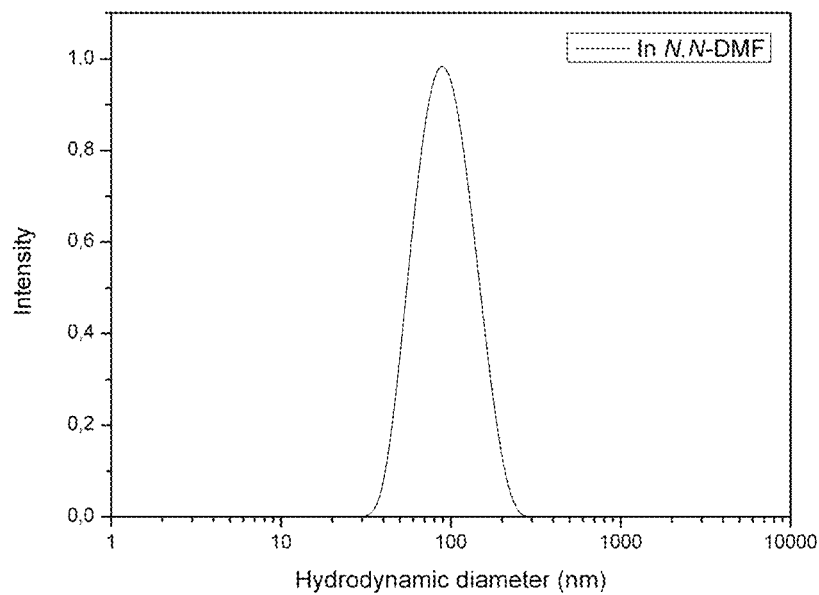
FIG. 53 shows the dynamic light scattering of micelle encapsulated Fe$_x$O$_y$ nanoparticles in N,N-dimethylformamide.

5 nmol $Fe_xO_y$ nanoparticles in toluene were precipitated by the addition of an equal volume of methanol. The cloudy mixture was centrifuged (6000×g; 10 min) and the supernatant was discarded. The remaining pellet was dissolved in 500 µL chloroform and mixed with 6.9 µmol (1390 fold excess) PI-b-PEO. The resulting solution was quickly injected into 9000 µL N,N-dimethylformamide and stirred for a minute. The clear, brownish colored solution thus obtained indicated the colloidal dissolution of the nanoparticles in polymer micelles. Micelle formation was confirmed by dynamic light scattering (DLS; FIG. 53).

Example 32

Composition of Micelle Encapsulated Magnetic, Oleic Acid, 10 nm $Fe_xO_y$ Nanoparticles in [BMIM][$BF_4$]

Figure 54:
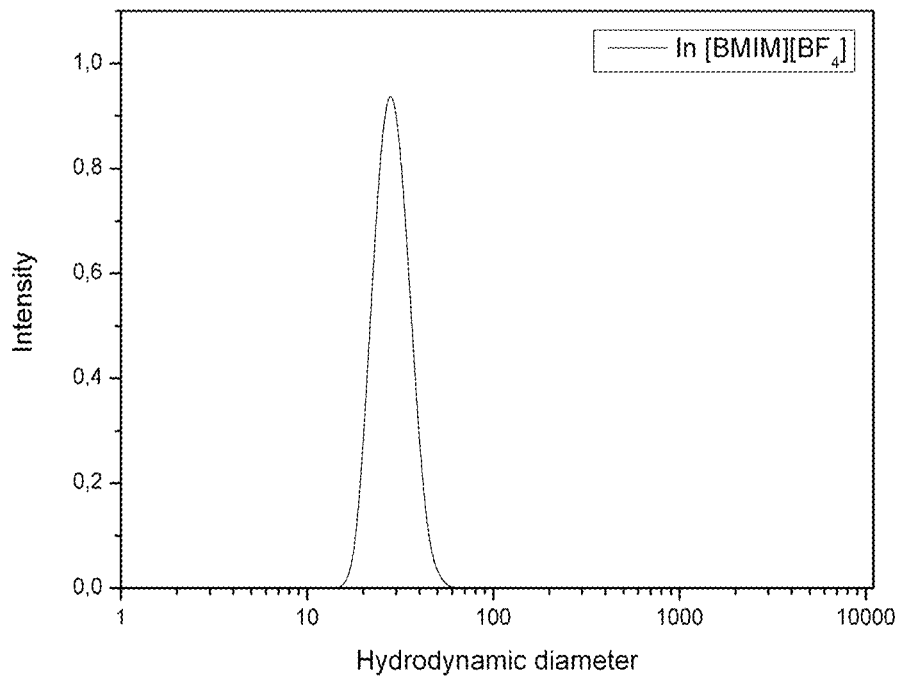
FIG. 54 shows the dynamic light scattering of micelle encapsulated Fe$_x$O$_y$ nanoparticles in [BMIM][BF$_4$].

5 nmol $Fe_xO_y$ nanoparticles in toluene were precipitated by the addition of an equal volume of methanol. The cloudy mixture was centrifuged (6000×g; 10 min) and the supernatant was discarded. The remaining pellet was dissolved in 500 µL chloroform and mixed with 6.9 µmol (1390 fold excess) PI-b-PEO. 100 µL of the resulting solution were quickly injected into 1500 µL [BMIM][$BF_4$], were vigorously stirred and heated carefully to evaporate the remaining $CHCl_3$. The clear, brownish colored solution thus obtained indicated the colloidal dissolution of the nanoparticles in polymer micelles. Micelle formation was confirmed by dynamic light scattering (DLS; FIG. 54).

Example 33

Composition of Micelle Encapsulated Fluorescent, Oleic Acid, 20 nm $NaYF_4$:Yb/$NaYF_4$ Nanoparticles in Methanol 9 nmol of NaYF4:Yb/NaYF4 nanoparticles in hexane were mixed with 30 µmol (3333 fold excess) PI-DETA (2000 g/mol) and the volume was adjusted to 1 mL. After 2 h of incubation the nanoparticles were precipitated by the addition of 1200 µL ethanol and centrifuged (10000×g; 10 min). The supernatant was discarded and the pellet was dissolved in 900 µL dichloromethane.

Figure 55:
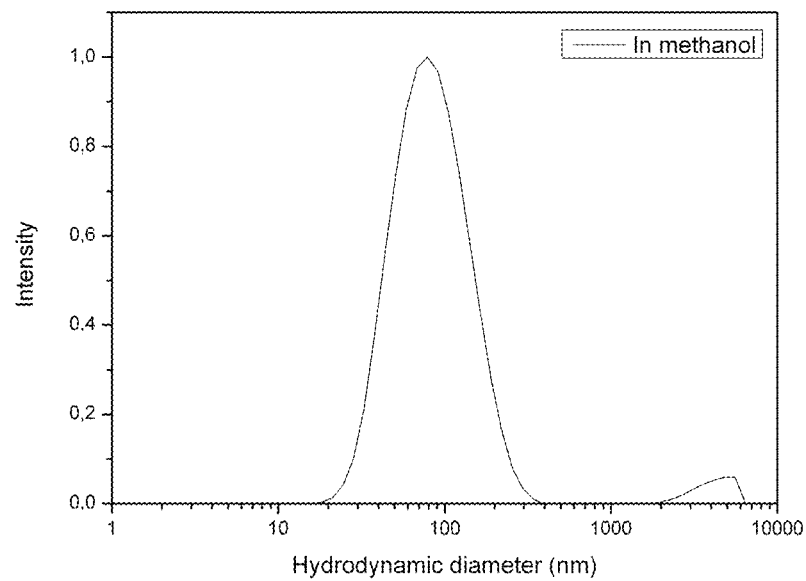
FIG. 55 shows the dynamic light scattering of micelle encapsulated NaYF$_4$:Yb/NaYF$_4$ nanoparticles in methanol.
Figure 56:
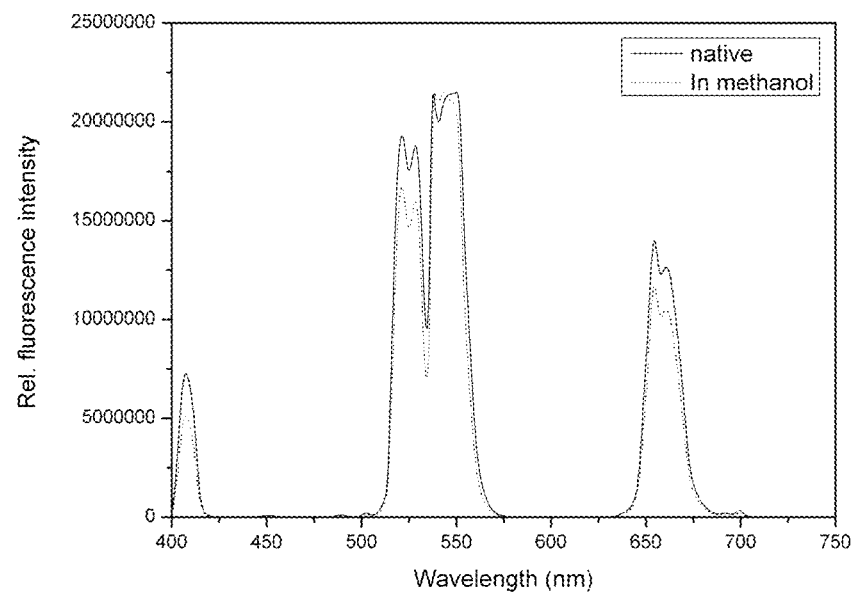
FIG. 56 shows the fluorescence spectra of native NaYF$_4$:Yb/NaYF$_4$ nanoparticles (solid line) and the micelle encapsulated NaYF$_4$:Yb/NaYF$_4$ nanoparticles in methanol (dotted line); Excitation at 978 nm.

700 µL (approx. 7 nmol) of this solution were mixed with 11.7 µmol (1666 fold excess) PI-b-PEO and the total volume was adjusted to 2000 µL. The resulting solution was quickly injected into 20 mL of methanol and stirred for a minute. The colorless solution was concentrated using a rotary evaporator (40° C.; 400 mbar) until a very concentrated solution (1-3 mL) was obtained. Subsequently, the volume was adjusted to 6 mL with methanol and divided into three equal parts. One of these parts was further diluted with 3 mL methanol (approx. 2.3 nmol $NaYF_4$:Yb/$NaYF_4$ nanoparticles) and characterized together with the native $NaYF_4$:Yb/$NaYF_4$ nanoparticles (2.3 nmol in 5 mL n-hexane). The encapsulation of the nanoparticles in polymeric micelles was concluded from the fact that no precipitation occurred after the injection into methanol, which is an excellent precipitant for the PI-DETA coated nanoparticles. Micelle formation was further confirmed by dynamic light scattering (DLS; FIG. 55). The emission properties of the nanoparticles are only slightly influenced by the encapsulation process (FIG. 56).

Example 34

Cross-Linking of Micelle Encapsulated, Fluorescent, Polyisoprene Coated CdSe/CdS Rod-Shaped Nanoparticles with 1,9-Nonanedithiol in Methanol
5a) Coating of Fluorescent, Octadecylphosphonic Acid Coated CdSe/CdS Rod-Shaped Nanoparticles with a Polyisoprene Ligand 56 nmol of octadecylphosphonic acid coated CdSe/CdS rod-shaped nanoparticles (~4.8 nm in width; ~12 nm in length) in hexane were mixed with 56 µmol (1000 fold excess) of diethylenetriamine functionalized polyisoprene (PI-DETA) and agitated for 30 minutes (total volume=4800 µL). Afterwards the polymer coated nanoparticles were precipitated by the addition of an 8 fold (volume) excess of ethanol and centrifuged for 30 minutes at 10° C. at 10.000× g. The supernatant was discarded while the residue was dissolved in 10 mL dichloromethane and filtered through a 0.2 µm PTFE filter.

15b) Cross-Linking of Micelle Encapsulated, Fluorescent, Polyisoprene Coated CdSe/CdS Rod-Shaped Nanoparticles in Methanol 0.045 g (3.6 µmol) of a poly(isoprene-block-ethylene oxide) (PI-b-PEO) diblockcopolymer were mixed with 96.3 µL (approx. 2 eq. per double-bond) 1,9-nonanedithiol and 2.0 mL of dichloromethane. Subsequently, the resulting solution was filtered through a 0.2 µm PTFE filter. 11.2 nmol of the polyisoprene coated nanoparticles were mixed with the PI-b-PEO-Solution and injected into 40 mL degassed methanol. The clear, slightly colored solution thus obtained indicated the colloidal dissolution of the nanoparticles in polymer micelles. Cross-linking of the hydrophobic polyisoprene moiety with the 1,9-nonanedithiol was achieved by illuminating the solution with UV-Light for 45 minutes, using a homemade illumination apparatus (4 PL-S 9W/2P BLB Philips 15752-9 lamps mounted in a radius of 7 cm around the samples in a closed box). The solution was concentrated to a volume of approximately 4 mL using a rotary evaporator. Micelle formation was confirmed by dynamic light scattering (DLS; FIG. 57). Cross-linking was confirmed by DLS measurements of a sample dissolved in a 10 fold volume of dichloromethane, showing virtually the same size distribution as in methanol. The absorption and emission properties of the nanoparticles are virtually unchanged by the encapsulation process (FIG. 58 and FIG. 59).
c) Transfer of Cross-Linked Micelle Encapsulated Nanoparticles to Propane-1,2-Diol The cross-linked micelle encapsulated nanoparticles were further purified by a density gradient centrifugation method. The gradient was prepared from dichloromethane and mixtures of dichloromethane and methanol in 4 stages. In the order of ascending density: dichloromethane, dichloromethane/methanol 80:20 (v/v), dichloromethane/methanol 60:40 (v/v), dichloromethane/methanol 55:45 (v/v). The cross-linked micelle encapsulated nanoparticles were placed on top of the gradient and subsequently centrifuged for 60 minutes at 50.000×g at 15° C. The colorless upper phase was discarded, while the rest of phases were mixed. The solvents were removed completely using a rotary evaporator. The residue was dissolved in 2 mL of dichloromethane. Subsequently 263 µL (approximately 1 nmol nanoparticles) of this solution were dried under a gentle nitrogen flow and the remaining solid was dissolved in 200 µL methanol. The solution was mixed with 200 µL propane-1,2-diol and the residual methanol was removed in vacuo.

Example 35

Conjugation of Antibody to Non-Aqueous Micelle Encapsulated Fluorescent Semiconductor Nanocrystals in Rac-1,2-Propanediol An aliquot of 50 µl (250 pmol) of the composition obtained in Example 34c was mixed with 10 µl (2.5 nmol) of a 0.25 mM non-aqueous stock solution of a PEGylated SMCC crosslinker. The sample was incubated at room temperature for 1 h. To avoid water contact upon purification of activated nanoparticles, crosslinker to NP ratio was limited to 10-fold, resulting in excess of NP—NH2 groups.

60 µl of activated fluorescent quantum dot-rods were mixed with 74 µl (0.5 nmol) of reduced Donkey Anti-Rabbit IgG (1 mg/mL) (Reduction was done with a 100 fold excess of Tris-(2-carboxyethyl)-phosphine-HCl (TCEP) for 1 h at room temperature). The sample was incubated for 2 h at room temperature.

Figure 60:
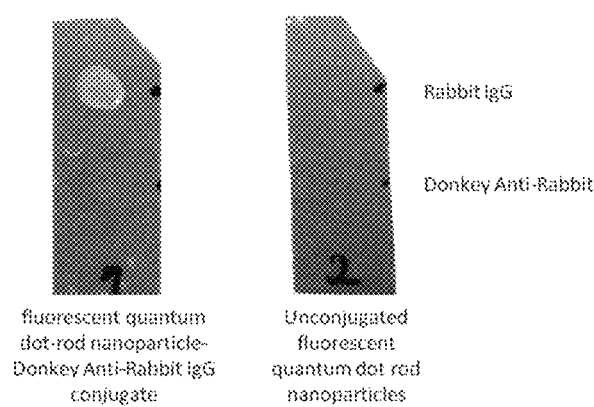
FIG. 60 shows the spot test analysis of fluorescent quantum dot-rod nanoparticle-donkey anti-rabbit IgG conjugates. Conjugation was performed in rac-1,2-propanediol. Success of antibody binding is evident from enrichment of the conjugate on the rabbit IgG Spot. No enrichment for the non conjugated control.

For the functional proof of the quantum dot-rod-antibody conjugate rabbit IgG and some other antibodies as negative controls were immobilized on stripes of nitrocellulose membrane and dried. Membranes were incubated with a solution of the fluorescent quantum dot-rod nanoparticle-Donkey Anti-Rabbit IgG conjugate and a solution of unconjugated control in rac-1,2-propanediol over night. The accumulation of the conjugate on the spots providing the rabbit IgG spot indicated a successful conjugation (FIG. 60). This test assembly was likewise applicable for analytic or diagnostic assessment of samples spotted on nitrocellulose or any other suitable target (e.g. membranes, plates, or slides).

Example 36

Toxicity Testing of Non-Aqueous Micelle Encapsulated Fluorescent Quantum Semiconductor Nanocrystals The toxicity of non-aqueous micelle encapsulated fluorescent quantum dot rods was tested on adenocarcinomic human alveolar basal epithelial cells (A549 cell line). The cells (80% confluent) were incuabted over night with 1:100 to 1:5 diluted samples of Example 34 cadmium containing semiconductor nanocrystals encapsulated in non-aqueous micelles. After 16 h the nanoparticle solution was removed from the cells and the cells were covered with 100 µl staining solution (2.5 µg/ml Hoechst 33342 and 75 nM MitoTracker Deep Red) for 30 min and fixed by covering with 100 µl 10% formalin solution for 20 min. After several washing steps the cells were analyzed with the Cellomics Array Scan Detector. The toxicity is estimated by combining the following values: intensity of Hoechst 33342 and MitoTracker DeepRed, cell count, nuclei size and cell morphology. It was discovered, that the non-aqueous encapsulation was sufficient to preserve the same minor toxicity effect observed for aqueous micelle encapsulated semiconductor nanocrystals and empty micelles without any nanoparticles. Thus the micelle preserved confirmation in non-aqueous solution. Additionally the micelle is sufficiently inert to preserve cellular uptake of nanocrystals.
Explicitly Disclosed is the Following

Example 37

Conjugation of PO$_4$-DNA to Aqueous Micelle Encapsulated Fluorescent Semiconductor Nanocrystals in Aqueous Solution An aliquot of 100 µl of a 100 µM stock solution of 5'-phosphate terminated DNA (33mer) was mixed with 2 mg of 1-ethyl-3-(3-dimethylaminopropyl)carbodiimide (EDC). Immediately 100 µl of aqueous micelle encapsulated fluorescent quantum dot-rods mixed with 100 µl 0.1 M imidazole (pH 6.0) was added and mixed properly. Subsequently a second portion of imidazole (40 µl 0.1 M) were added. The sample was heated to 50° C. for 1 h in a heating block with shaking (700 rpm).

For purification the nanoparticle-DNA conjugates were transferred into an ultrafiltration unit and diluted with 5 mL of 0.5×PBS. After centrifugation at 1200*g for 15 min the supernatant was discarded and centrifugation continued until a residual volume of 500 µL was achieved.

The samples were analyzed via gel electrophoresis on agarose. An aliquot of 5.2 µL of the sample was diluted with 19.8 µL 1×PBS and 5 µL gel loading buffer was added. Aliquots of 25 of this mixture were applied to a 1.5% agarose gel. After processing the electrophoresis by applying 90 V for 50 min, samples were visualized by UV excitation of the quantum dot-rods. Successful conjugation was indicated by a small progression towards the anode due to the negative charge of the conjugated nanoparticles.

Example 38

Conjugation of SH-DNA to Aqueous Micelle Encapsulated Fluorescent Semiconductor Nanocrystals in Aqueous Solution An aliquot of 33 µL of aqueous micelle encapsulated fluorescent quantum dot-rods was mixed with 10.8 µL of a 92 µM stock solution of 5'-thiol terminated DNA (33mer) and adjusted to 100 by addition of 1×phosphate buffered saline (PBS). The sample was heated to 50° C. for 2 h in a heating block.

For purification the nanoparticle-DNA conjugates were transferred into an ultrafiltration unit and diluted with 5 mL of 0.5×PBS. After centrifugation at 1200*g for 20 min the supernatant was discarded and centrifugation continued until a residual volume of 420 µL was achieved.

The purified samples were analyzed via gel electrophoresis on agarose. Aliquots of 5 µL of each sample were diluted with 20 µL 1×PBS and 5 µL gel loading buffer was added. Aliquots of 25 µL of this mixture were applied to a 0.8% agarose gel. After processing the electrophoresis by applying 90 V voltage for 1 h, samples were visualized by UV excitation of the quantum dot-rods. Successful conjugation was indicated by a small progression towards the anode due to the negative charge of the conjugated nanoparticles, whereas the unconjugated controls moved to the cathode.

Example 39

Figure 61:
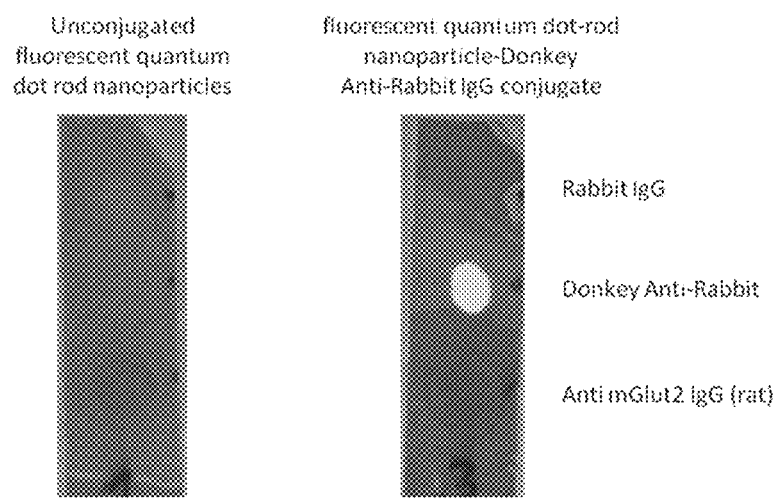
FIG. 61 shows a spot test analysis of fluorescent quantum dot-rod nanoparticle-donkey anti-rabbit IgG conjugates. Conjugation was performed in aqueous solution. Success of DNA binding is evident from the accumulation of the conjugate on the Rabbit IgG Spot. No accumulation was observed for the unconjugated control.

Conjugation of Antibody to Aqueous Micelle Encapsulated Fluorescent Semiconductor Nanocrystals in Aqueous Solution An aliquot of 400 µl of aqueous micelle encapsulated fluorescent quantum dot-rods was mixed with 80 µl of a 2.5 mM aqueous stock solution of a PEGylated succinimide-maleimide (SM-PEG) crosslinker. The sample was incubated at room temperature for 1.5 h. For purification from unbound crosslinker the sample was transferred to a PD10 desalting column and eluted with 1×PBS. The fluorescent samples were collected and pooled. Activated and purified fluorescent quantum dot-rods (1.1 mL) were mixed with 285 µl of reduced donkey anti-rabbit IgG. Reduction was done with a 100 fold excess of tris-(2-carboxyethyl)-phosphine-HCl (TCEP) for 1 h at room temperature. The sample was incubated for 2 h at room temperature. For the functional proof of the quantum dot-rod-antibody conjugate rabbit IgG and some other antibodies as negative controls were immobilized on stripes of nitrocellulose membrane and dried. Membranes were incubated with a solution of the fluorescent quantum dot-rod nanoparticle-donkey anti-rabbit IgG conjugate and a solution of unconjugated control for 2 h. The accumulation of the conjugate on the spots providing the rabbit IgG spot indicated a successful conjugation (FIG. 61).

Example 40

Avidin Coating of Aqueous Micelle Encapsulated Fluorescent Semiconductor Nanocrystals in Aqueous Solution NeutrAvidin (NAV) was dissolved in ultra pure water giving 100 mg/mL solution. In a 25 mL glass vial 1 mL of this NAV solution was mixed with 5 mL 5 µM biotinylated semiconductor nanocrystals mainly prepared as described in example 11. Incubation was executed at RT for 1 h and if convenient continued up to 2 days in a refrigerator. The clear solution of NAV coated QDs was than concentrated in a Centriprep Ultracel YM-50 50,000 MWCO to give appropriate volume for size exclusion chromatography (less than 4 but more than 1 mL). Excess NAV was removed on a High Load Superdex 200 16/60 column by isocratic elution in 1×PBS buffer. The fractions of purified NAV decorated QDs were pooled and kept in a fridge to be used for further biofunctionalization of QDs with biotinylated Molecules. The amount of biotin binding sites per QD were analysed by HABA quantification using free biotin to titrate the HABA molecules bound to NAV. All preparations performed so far revealed approx. 80 biotin binding sites per QD.

Example 41

Biomolecule Binding to Avidin Coated Aqueous Micelle Encapsulated Semiconductor Nanocrystals in Aqueous Solution Several biotinylated biomolecules (DNA, peptide, Fab Fragments and antibodies) were be bound to NAV coated semiconductor nanoparticles and proofed their performance in in-vitro and in-vivo assays. Exemplarily the binding of a 3'-biotinylated 33 base pair DNA oligonucleotide is described in detail. 12.5 µL 100 µM biotinylated DNA was diluted with 37.5 µL 1×PBS. 50 of this DNA solution was mixed with 50 µL 1 µM NAV-QD, thereby it was important to ad 5 times 10 µL aliquots each, to ensure appropriate distribution of DNA on the QDs. Binding of biotinylated biomolecule was straight forward and executed for all biomolecules in 1×PBS buffer using approximately a fourth of the available biotin binding sites. Incubation was done for 30 minutes up to 1 h at RT under moderate constant mixing on a rocking shaker, if convenient incubation was continued up to 2 days in a refrigerator. In a subsequent step remaining biotin binding sites were saturated by addition of free biotin. In explicit 5 µL 1 mM biotin was added to the bioconjugate and the mixture was incubated on a rocking shaker for 30 minutes at RT. Finally the bioconjugate was purified from excess biotin using the ultra concentrators. The sample was transferred into Centriprep Ultracel YM-50 50,000 MWCO and washed with 5 mL 0.5×PBS by centrifugation at 1200*g for 15 min to give approximately 350 µL DNA-QD molecular probe. Assessment of conjugation performance was undertaken by agarose gel band shift analysis and DNA hybridization assay as described above.

The invention claimed is:

1. A method, comprising: providing a composition comprising at least one micelle encapsulating one or more nanoparticle(s) in a non-aqueous solution, wherein the micelle comprises a cross-linked hydrophilic shell, wherein the cross-linking of the micelle is enabled using thiol-ene click chemistry, and wherein the encapsulation and cross-linking are performed under completely anhydrous conditions.

2. The method according to claim 1, wherein the one or more nanoparticle(s) is a luminescent nanoparticle.

3. The method according to claim 2, wherein the one or more nanoparticle(s) is a semi-conductor nanoparticle.

4. The method according to claim 3, wherein the one or more nanoparticle(s) is doped by heavy-metal ions including Ag, Cu, Co, or Mn.

5. The method according to claim 2, wherein the one or more nanoparticle(s) is chosen from a lattice lanthanide doped nanoparticle.

6. The method according to claim 1, wherein the one or more nanoparticle(s) is a metal nanoparticle or a metal oxide nanoparticle.

7. The method according to claim 1, wherein a material of the one or more nanoparticle(s) is defined by a formula $M_w N_x A_y B_z$, wherein M and N are independently selected from elements from group 8, 9, 10, 11, 12, 13, or 14 of the periodic table, including Fe, Co, Ni, Pt, Cu, Zn, Cd, Al, Ga, In, Ge, Sn, or Pb, and A and B are independently selected from elements from group 10, 11, 13, 15, or 16 from the periodic table, including Pd, Pt, N, P, As, Sb, Ga, O, S, Se, or Te, and wherein w, x, y, and z can be independently varied between 0 and 1 and their integral multiples under a proviso that positive charges of the cationic elements equal negative charges of the anionic elements.

8. The method according to claim 1, wherein the one or more nanoparticle(s) comprises at least one shell.

9. The method according to claim 8, wherein a material of the at least one shell is defined by the formula $O_s C_t D_u$, wherein O can be independently chosen from group 8, 9, 10, 11, 12, 13, or 14 from the periodic table, including Fe, Co, Ni, Pt, Cu, Zn, Cd, Al, Ga, In, Ge, Sn, or Pb, and C and D can be independently chosen from group 10, 11, 15, or 16 from the periodic table, including Pd, Pt, N, P, As, Sb, 0, S, Se, or Te, and wherein s, t, and u can be independently varied between 0 and 1 and their integral multiples under a proviso that positive charges of the cationic elements equal negative charges of the anionic elements and under a proviso that the compositions of $M_w N_x A_y B_z$ and $O_s C_t D_u$ are not identical.

10. The method according to claim 1, wherein the at least one micelle comprises micelle forming elements including amphiphilic block co-polymers.

11. The method according to claim 10, wherein the amphiphilic block co-polymers comprise at least two different polymer blocks of different compatibility towards solvents.

12. The method according to claim 11, wherein the amphiphilic block co-polymers are linear or branched or star-shaped or dendritic.

13. The method according to claim 1, wherein the at least one micelle is formed in the non-aqueous solution and the non-aqueous solution is chosen from at least one of:
  unbranched, branched, or cyclic alkanes, optionally bearing one or more halogen atoms, including pentane, hexane, iso-hexanes, cyclopentane, cyclohexane, dichloromethane, chloroform, 1,1-dichloroethane, or 1,2-dichloroethane;
  halogenated alkenes, like 1,1-dichloroethene or all isomers of 1,2-dichloroethene; optionally alkylated aromatic or heteroaromatic solvents, optionally bearing one or more halogen atoms, including benzene, toluene, ethyl benzene, xylenes, chloro benzene, pyridine, collidines, or lutidines;

unbranched, branched, or cyclic ethers, including diethyl ether, diisopropyl ether, methyl t-butyl ether, tetrahydrofuran, or 1,4-dioxane;

carbonyl compounds, including acetone, methyl ethyl ketone, cylopentanone, or cyclohexanone;

carboxylic acid esters, including ethyl acetate, unbranched or branched $C_1$-$C_5$ alkanols, including methanol, ethanol, n-propanol, i-propanol, or all isomers of butanol and pentanol;

polyols, including ethylene glycol, 1,2-propanediol, 1,3-propanediol, glycerol, 1,2-butanediol, 1,3-butanediol, 1,4-butanediol, 1,2,4-butanetriol, diethylene glycol (DEG);

ethers of polyols, including 2-methoxyethanol, bis-(2-methoxyethyl) ether (diglyme);

esters of polyols, including diacetoxyethane;

carboxylic acids, including formic acid, acetic acid, propanoic acid, lactic acid;

dialkyl sulfoxides, including dimethyl sulfoxide (DMSO);

carboxylic acid amides, including formamide, acetamide, N-methyl formamide, N-methyl acetamide, N,N-dimethyl formamide (DMF), N,N-dimethyl acetamide (DMA), or N-methyl pyrrolidone (NMP);

phosphoric acid amides including hexamethyl phosphoric acid triamide (HMPA);

urea based solvents including 1,3-dimethyl-3,4,5,6-tetrahydro-2(1H)-pyrimidinone (DMPU), 1,3-dimethyl-2-imidazolidinone (DMI), tetramethyl urea (TEMUR); or lower alkylnitriles including acetonitrile, propionitrile, or butyronitrile;

ionic liquids, including ammonium-based ionic liquids;

imidazolium based ionic liquids including 1-allyl-3-methylimidazolium, 1-benzyl-3-methylimidazolium, 1-butyl-2,3-dimethylimidazolium, 1-butyl-3-methylimidazolium, 1-decyl-3-methylimidazolium, 1,3-didecyl-2-methylimidazolium, 1,3-dimethylimidazolium, 1,2-dimethyl-3-propylimidazolium, 1-dodecyl-3-methylimidazolium, 1-ethyl-2,3-dimethylimidazolium, 1-ethyl-3-methylimidazolium, 1-hexadecyl-3-methylimidazolium, 1-hexyl-3-methylimidazolium, 1-(2-hydroxyethyl)-3-methylimidazolium, 1-methyl-3-octadecylimidazolium, 1-methyl-3-octylimidazolium, salts of 1-methyl-3-propylimidazolium with complex anions including tetrafluoroborate; piperidinium-based ionic liquids, including 1-butyl-1-methylpiperidinium, or 1-methyl-1-propylpiperidinium;

pyridinium-based ionic liquids including 1-alkyl-2-methylpyridinium, 1-alkyl-3-methylpyridinium, 1-alkyl-4-methylpyridinium, 1-butylpyridinium, 1-propylpyridinium, 1-ethylpyridinium, salts of 1-hexylpyridinium salts with complex anions including tetrafluoroborate;

pyrrolidinium-based ionic liquids, including 1-butyl-1-methylpyrrolidinium, 1-ethyl-1-methylpyrrolidinium, salts of 1-methyl-1-propylpyrrolidinium with complex anions, and combinations or combinations of mixtures thereof.

14. The method according to claim 1, wherein the non-aqueous solution comprises one or more of a water miscible non-aqueous solvent and a non-aqueous solvent, which does not form azeotropic phases with water.

15. The method according to claim 14, wherein the water miscible non-aqueous solvent has a higher boiling point than water.

* * * * *